US005932590A

United States Patent [19]
Ciccarone et al.

[11] Patent Number: 5,932,590
[45] Date of Patent: Aug. 3, 1999

[54] INHIBITORS OF FARNESYL-PROTEIN TRANSFERASE

[75] Inventors: Terrence M. Ciccarone, Telford; S. Jane deSolms, Norristown, both of Pa.

[73] Assignee: Merck & Co., Inc., Rahway, N.J.

[21] Appl. No.: 08/985,337

[22] Filed: Dec. 4, 1997

Related U.S. Application Data

[60] Provisional application No. 60/032,578, Dec. 5, 1996.

[51] Int. Cl.$^6$ .......................... C07D 217/20; A61K 31/47
[52] U.S. Cl. .......................... 514/309; 514/307; 546/139; 546/141; 546/148
[58] Field of Search ...................................... 546/139, 141, 546/148; 514/307, 309

[56] References Cited

U.S. PATENT DOCUMENTS

| | | | |
|---|---|---|---|
| 5,141,851 | 8/1992 | Brown et al. | 435/15 |
| 5,238,922 | 8/1993 | Graham et al. | 514/357 |
| 5,340,828 | 8/1994 | Graham et al. | 435/15 |
| 5,352,705 | 10/1994 | Deana et al. | 514/630 |
| 5,439,918 | 8/1995 | De Solms et al. | 546/147 |
| 5,504,212 | 4/1996 | De Solms et al. | 564/162 |
| 5,534,537 | 7/1996 | Ciccarone et al. | 514/397 |
| 5,571,835 | 11/1996 | Anthony et al. | 514/397 |
| 5,578,629 | 11/1996 | Ciccarone et al. | 514/397 |

FOREIGN PATENT DOCUMENTS

| | | |
|---|---|---|
| 0 618 221 A2 | 10/1994 | European Pat. Off. . |
| 0 675 112 A1 | 10/1995 | European Pat. Off. . |
| 0 696 593 A2 | 2/1996 | European Pat. Off. . |
| WO 96/00736 | 1/1996 | WIPO . |
| WO 96/10034 | 4/1996 | WIPO . |
| WO 96/24612 | 8/1996 | WIPO . |
| WO 97/18813 | 5/1997 | WIPO . |
| WO 97/30053 | 8/1997 | WIPO . |

OTHER PUBLICATIONS

Gibbs, J.B. et al., "Selective Inhibition of Farnesyl–Protein Transferase Blocks Ras Processing in Vivo," The Journal of Biological Chemistry, vol. 268, No. 11, pp. 7617–7620 (1993).

Goldstein, J.L. et al., "Nonfarnesylated Tetrapeptide Inhibitors of Protein Farnesyltransferase," The Journal of Biological Chemistry, vol. 266, No. 24, pp. 15575–15578 (1991).

Graham, S.L., "Inhibitors of protein farnesylation: a new approach to cancer chemotherapy," Exp. Opin. Ther. Patents vol. 5 (12), pp. 1269–1285 (1995).

James, G.L. et al., "Benzodiazepine Peptidomimetics: Potent Inhibitors of Ras Farnesylation in Animal Cells," Science, vol. 260 pp. 1937–1942 (1993).

James, G.L. et al., "Benzodiazepine Peptidomimetic BZA–5B Interrupts the MAP Kinase Activation Pathway in H–Ras–transformed Rat–1 Cells, but Not in Untransformed Cells," The Journal of Biological Chemistry, vol. 269, No. 44, pp. 27705–27714 (1994).

James, G., et al., "Polylysine and CVIM Sequences of K–RasB Dictate Specificity of Prenylation and Confer Resistance to Benzodiazepine Peptidomimetic in Vitro," The Journal of Biological Chemistry, vol. 270, No. 11, pp. 6221–6226 (1995).

Kohl, N.E., et al., "Inhibition of farnesyltransferase induces regression of mammary and salivary carcinomas in ras transgenic mice," Nature Medicine, vol. 1, No. 8, pp. 792–797 (1995).

Kohl, N.E. et al., "Protein farnesyltransferase inhibitors block the growth of ras–dependent tumors in nude mice", Proc. Natl. Acad. Sci. USA, Med. Sciences, vol. 91, pp. 9141–9145 (1994).

Kohl, N.E. et al., "Selective Inhibition of ras–Dependent Transformation by a Farnesyltransferase Inhibitor", Science, vol. 260, pp. 1934–1937 (1993).

Pompliano, D.L., "Steady–State Kinetic Mechanism of Ras Farnesyl:Protein Transferase," Biochemistry, vol. 31, pp. 3800–3807 (1992).

Sepp–Lorenzino, L., et al., "A Peptidomimetic Inhibitor of Farnesyl:Protein Transferase Blocks the Anchorage–dependent and –independent Growth of Human Tumor Cells Lines," Cancer Research, vol. 55, pp. 5302–5309 (1995).

*Primary Examiner*—Zinna Northington Davis
*Attorney, Agent, or Firm*—Dianne Pecoraro; David A. Muthard; Mark R. Daniel

[57] ABSTRACT

The present invention is directed to compounds which inhibit farnesyl-protein transferase (FTase) and the farnesylation of the oncogene protein Ras. The invention is further directed to chemotherapeutic compositions containing the compounds of this invention and methods for inhibiting farnesyl-protein transferase and the farnesylation of the oncogene protein Ras.

38 Claims, No Drawings

INHIBITORS OF FARNESYL-PROTEIN TRANSFERASE

DOMESTIC PRIORITY CLAIM

This application claims priority from the U.S. Provisional application Ser. No. 60/032,578, filed on Dec. 5, 1996.

BACKGROUND OF THE INVENTION

The Ras protein is part of a signalling pathway that links cell surface growth factor receptors to nuclear signals initiating cellular proliferation. Biological and biochemical studies of Ras action indicate that Ras functions like a G-regulatory protein. In the inactive state, Ras is bound to GDP. Upon growth factor receptor activation Ras is induced to exchange GDP for GTP and undergoes a conformational change. The GTP-bound form of Ras propagates the growth stimulatory signal until the signal is terminated by the intrinsic GTPase activity of Ras, which returns the protein to its inactive GDP bound form (D. R. Lowy and D. M. Willumsen, Ann. Rev. Biochem. 62:851–891 (1993)). Mutated ras genes are found in many human cancers, including colorectal carcinoma, exocrine pancreatic carcinoma, and myeloid leukemias. The protein products of these genes are defective in their GTPase activity and constitutively transmit a growth stimulatory signal.

Ras must be localized to the plasma membrane for both normal and oncogenic functions. At least 3 post-translational modifications are involved with Ras membrane localization, and all 3 modifications occur at the C-terminus of Ras. The Ras C-terminus contains a sequence motif termed a "CAAX" or "Cys-Aaa$^1$-Aaa$^2$-Xaa" box (Cys is cysteine, Aaa is an aliphatic amino acid, the Xaa is any amino acid) (Willumsen et al., Nature 310:583–586 (1984)). Depending on the specific sequence, this motif serves as a signal sequence for the enzymes farnesyl-protein transferase or geranylgeranyl-protein transferase, which catalyze the alkylation of the cysteine residue of the CAAX motif with a $C_{15}$ or $C_{20}$ isoprenoid, respectively. (S. Clarke., Ann. Rev. Biochem. 61:355–386 (1992); W. R. Schafer and J. Rine, Ann. Rev. Genetics 30:209–237 (1992)). The Ras protein is one of several proteins that are known to undergo post-translational farnesylation. Other farnesylated proteins include the Ras-related GTP-binding proteins such as Rho, fungal mating factors, the nuclear lamins, and the gamma subunit of transducin. James, et al., J. Biol. Chem. 269, 14182 (1994) have identified a peroxisome associated protein Pxf which is also farnesylated. James, et al., have also suggested that there are farnesylated proteins of unknown structure and function in addition to those listed above.

Inhibition of farnesyl-protein transferase has been shown to block the growth of Ras-transformed cells in soft agar and to modify other aspects of their transformed phenotype. It has also been demonstrated that certain inhibitors of farnesyl-protein transferase selectively block the processing of the Ras oncoprotein intracellularly (N. E. Kohl et al., Science, 260:1934–1937 (1993) and G. L. James et al., Science, 260:1937–1942 (1993). Recently, it has been shown that an inhibitor of farnesyl-protein transferase blocks the growth of ras-dependent tumors in nude mice (N. E. Kohl et al., Proc. Natl. Acad. Sci U.S.A., 91:9141–9145 (1994) and induces regression of mammary and salivary carcinomas in ras transgenic mice (N. E. Kohl et al., Nature Medicine, 1:792–797 (1995).

Indirect inhibition of farnesyl-protein transferase in vivo has been demonstrated with lovastatin (Merck & Co., Rahway, N.J.) and compactin (Hancock et al., ibid; Casey et al., ibid; Schafer et al., Science 245:379 (1989)). These drugs inhibit HMG-CoA reductase, the rate limiting enzyme for the production of polyisoprenoids including farnesyl pyrophosphate. Farnesyl-protein transferase utilizes farnesyl pyrophosphate to covalently modify the Cys thiol group of the Ras CAAX box with a farnesyl group (Reiss et al., Cell, 62:81–88 (1990); Schaber et al., J. Biol. Chem., 265:14701–14704 (1990); Schafer et al., Science, 249:1133–1139 (1990); Manne et al., Proc. Natl. Acad. Sci USA, 87:7541–7545 (1990)). Inhibition of farnesyl pyrophosphate biosynthesis by inhibiting HMG-CoA reductase blocks Ras membrane localization in cultured cells. However, direct inhibition of farnesyl-protein transferase would be more specific and attended by fewer side effects than would occur with the required dose of a general inhibitor of isoprene biosynthesis.

Inhibitors of farnesyl-protein transferase (FPTase) have been described in two general classes. The first are analogs of farnesyl diphosphate (FPP), while the second class of inhibitors is related to the protein substrates (e.g., Ras) for the enzyme. The peptide derived inhibitors that have been described are generally cysteine containing molecules that are related to the CAAX motif that is the signal for protein prenylation. (Schaber et al., ibid; Reiss et. al., ibid; Reiss et al., PNAS, 88:732–736 (1991)). Such inhibitors may inhibit protein prenylation while serving as alternate substrates for the farnesyl-protein transferase enzyme, or may be purely competitive inhibitors (U.S. Pat. No. 5,141,851, University of Texas; N. E. Kohl et al., Science, 260:1934–1937 (1993); Graham, et al., J. Med. Chem., 37, 725 (1994)). In general, deletion of the thiol from a CAAX derivative has been shown to dramatically reduce the inhibitory potency of the compound. However, the thiol group potentially places limitations on the therapeutic application of FPTase inhibitors with respect to pharmacokinetics, pharmacodynamics and toxicity. Therefore, a functional replacement for the thiol is desirable.

It has recently been shown that farnesyl-protein transferase inhibitors are inhibitors of proliferation of vascular smooth muscle cells and are therefore useful in the prevention and therapy of arteriosclerosis and diabetic disturbance of blood vessels (JP H7-112930). It has also recently been disclosed that certain tricyclic compounds which optionally incorporate a piperidine moiety are inhibitors of FPTase (WO 95/10514, WO 95/10515 and WO 95/10516). It has also been disclosed that certain 1,2,3,4-tetrahydroisoquinoline peptidomimetic compounds, some of which incorporate an imidazole moiety, are inhibitors of FPTase (U.S. Pat. No. 5,439,918, EP 0 618 221 A2 and EP 0 675 112 A1).

It is, therefore, an object of this invention to develop novel peptidomimetic compounds that do not have a thiol moiety, and that will inhibit farnesyl-protein transferase and thus, the post-translational farnesylation of proteins. It is a further object of this invention to develop chemotherapeutic compositions containing the compounds of this invention and methods for producing the compounds of this invention.

SUMMARY OF THE INVENTION

The present invention comprises peptidomimetic 1,2,3,4-tetrahydroisoquinolines and homologous compounds which inhibit the farnesyl-protein transferase. Furthermore, these compounds differ from such heterocyclic compounds previously described as inhibitors of farnesyl-protein transferase with respect to the position of substituents about the nitrogen containing ring. Further contained in this invention are chemotherapeutic compositions containing these farnesyl transferase inhibitors and methods for their production.

The compounds of this invention are illustrated by the formulae A:

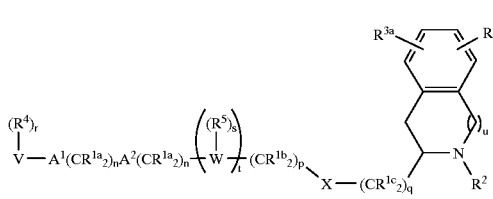

DETAILED DESCRIPTION OF THE INVENTION

The compounds of this invention are useful in the inhibition of farnesyl-protein transferase and the farnesylation of the oncogene protein Ras. In a first embodiment of this invention, the inhibitors of farnesyl-protein transferase are illustrated by the formula A:

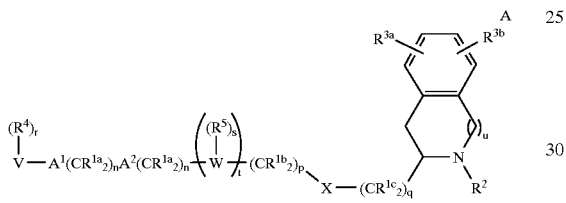

wherein:
$R^{1a}$, $R^{1b}$ and $R^{1c}$ are independently selected from:
a) hydrogen,
b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, $R^8O$—, $R^9S(O)_m$—, $R^8C(O)NR^8$—, CN, $NO_2$, $(R^8)_2N$—$C(NR^8)$—, $R^8C(O)$—, $R^8OC(O)$—, $N_3$, —$N(R^8)_2$, or $R^9OC(O)NR^8$—,
c) $C_1$–$C_6$ alkyl unsubstituted or substituted by unsubstituted or substituted aryl, heterocyclic, $C_3$–$C_{10}$ cycloalkyl, $C_2$–$C_6$ alkenyl, $C_2$–$C_6$ alkynyl, $R^8O$—, $R^9S(O)_m$—, $R^8C(O)NR^8$—, CN, $(R^8)_2N$—$C(NR^8)$—, $R^8C(O)$—, $R^8OC(O)$—, $N_3$, —$N(R^8)_2$, or $R^9OC(O)$—$NR^8$—;

$R^2$ is selected from: H; unsubstituted or substituted $C_{1-8}$ alkyl, unsubstituted or substituted $C_{2-8}$ alkenyl, unsubstituted or substituted aryl, unsubstituted or substituted heterocycle, $(CH_2)_pR11$,

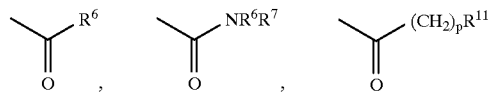

and —$S(O)_2R^6$,
wherein the substituted group is substituted with one or more of:
1) aryl or heterocycle, unsubstituted or substituted with one or two groups selected from:
a) $C_{1-4}$ alkyl,
b) $(CH_2)_pOR^6$,
c) $(CH_2)_pNR^6R^7$,
d) halogen,
e) $C_{1-4}$ perfluoroalkyl,
2) $C_{3-6}$ cycloalkyl,
3) $OR^6$,
4) $SR^6$, $S(O)R^6$, $SO_2R^6$,
5) —$NR^6R^7$ 6) 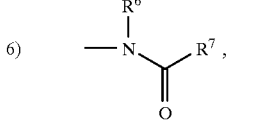

7) 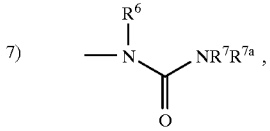

8) 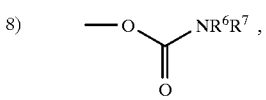

9) 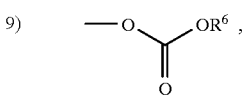

10) 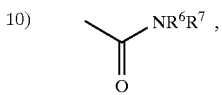

11) —$SO_2$—$NR^6R^7$,

12) 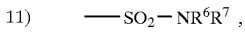

13) 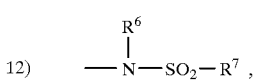

14) 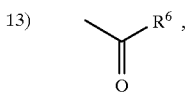

15) $C_{1-8}$ alkyl, or
16) $C_{1-8}$ perfluoroalkyl;
$R^{3a}$ and $R^{3b}$ are independently selected from:
a) hydrogen,
b) unsubstituted or substituted aryl, unsubstituted or substituted heterocycle, unsubstituted or substituted $C_3$–$C_{10}$ cycloalkyl, unsubstituted or substituted $C_2$–$C_6$ alkenyl, $C_2$–$C_6$ alkynyl, halogen, $C_1$–$C_6$ perfluoroalkyl, R⁸O—, R⁹S(O)ₘ—, R⁸C(O)NR⁸—, (R⁸)₂NC(O)—, R⁹C(O)O—, R⁸₂N—C(NR⁸)—, CN, NO₂, R⁸C(O)—, N₃, —N(R⁸)₂, or R⁹OC(O)NR⁸—, c) unsubstituted C₁–C₆ alkyl, d) substituted C₁–C₆ alkyl wherein the substituent on the substituted C₁–C₆ alkyl is selected from unsubstituted or substituted aryl, unsubstituted or substituted heterocyclic, C₃–C₁₀ cycloalkyl, C₂–C₆ alkenyl, C₂–C₆ alkynyl, R⁸O—, R⁹S(O)ₘ—, R⁸C(O)NR⁸—, (R⁸)₂NC(O)—, R⁸₂N—C(NR⁸)—, CN, R⁸C(O)—, N₃, —N(R⁸)₂, and R⁹OC(O)—NR⁸—;

R⁴ is independently selected from:

a) hydrogen, b) unsubstituted or substituted aryl, unsubstituted or substituted heterocycle, C₃–C₁₀ cycloalkyl, C₂–C₆ alkenyl, C₂–C₆ alkynyl, perfluoroalkyl, F, Cl, Br, R⁸O—, R⁹S(O)ₘ—, R⁸C(O)NR⁸—, CN, NO₂, R⁸₂N—C(NR⁸)—, R⁸C(O)—, R⁸OC(O)—, N₃, —N(R⁸)₂, or R⁹OC(O)NR⁸—, and c) C₁–C₆ alkyl unsubstituted or substituted by aryl, heterocycle, C₃–C₁₀ cycloalkyl, C₂–C₆ alkenyl, C₂–C₆ alkynyl, perfluoroalkyl, F, Cl, Br, R⁸O—, R⁹S(O)ₘ—, R⁸C(O)NH—, CN, H₂N—C(NH)—, R⁸C(O)—, R⁸OC(O)—, N₃, —N(R⁸)₂, or R⁸OC(O)NH—;

R⁵ is independently selected from:

a) hydrogen, b) C₂–C₆ alkenyl, C₂–C₆ alkynyl, C₃–C₆ cycloalkyl, perfluoroalkyl, F, Cl, Br, R⁸O—, R⁹S(O)ₘ—, R⁸C(O)NR⁸—, CN, NO₂, (R⁸)₂N—C—(NR⁸)—, R⁸C(O)—, R⁸OC(O)—, N₃, —N(R⁸)₂, or R⁹OC(O)NR⁸—, and c) C₁–C₆ alkyl, unsubstituted or substituted by perfluoroalkyl, F, Cl, Br, R⁸O—, R⁹S(O)ₘ—, R⁸C(O)NR⁸—, CN, (R⁸)₂N—C(NR⁸)—, R⁸C(O)—, R⁸OC(O)—, N₃, —N(R⁸)₂, or R⁹OC(O)NR⁸—;

R⁶, R⁷ and R⁷ᵃ are independently selected from: H; C₁₋₄ alkyl, C₃₋₆ cycloalkyl, heterocycle, aryl, C₁₋₄ perfluoroalkyl, unsubstituted or substituted with one or two substituents selected from:

a) C₁₋₄ alkoxy, b) substituted or unsubstituted aryl or substituted or unsubstituted heterocycle, c) halogen, d) HO, e) 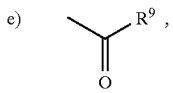

f) 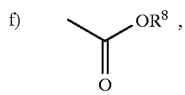

g) —S(O)ₘR⁹, or h) N(R⁸)₂; or

R⁶ and R⁷ may be joined in a ring;

R⁷ and R⁷ᵃ may be joined in a ring;

R⁸ is independently selected from hydrogen, C₁–C₆ alkyl, benzyl, 2,2,2-trifluoroethyl and aryl;

R⁹ is independently selected from C₁–C₆ alkyl and aryl;

R¹⁰ is selected from: H; R⁸C(O)—; R⁹S(O)ₘ—; unsubstituted or substituted C₁₋₄ alkyl, unsubstituted or substituted C₃₋₆ cycloalkyl, unsubstituted or substituted heterocycle, unsubstituted or substituted aryl, substituted aroyl, unsubstituted or substituted heteroaroyl, substituted arylsulfonyl, unsubstituted or substituted heteroarylsulfonyl, wherein the substituted group is substituted with one or two substituents selected from:

a) C₁₋₄ alkoxy, b) aryl or heterocycle, c) halogen, d) HO, e) 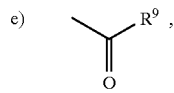

f) 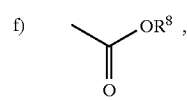

g) —S(O)ₘR⁹ h) N(R⁸)₂, and i) C₃₋₆ cycloalkyl;

R¹¹ is selected from: unsubstituted or substituted aryl, unsubstituted or substituted heterocycle, unsubstituted or substituted pyridinone;

A¹ and A² are independently selected from: a bond, —CH=CH—, —C≡C—, —C(O)—, —C(O)NR⁸—, —NR⁸C(O)—, O, —N(R⁸)—, —S(O)₂N(R⁸)—, —N(R⁸)S(O)₂—, or S(O)ₘ;

V is selected from:

a) hydrogen, b) heterocycle, c) aryl, d) C₁–C₂₀ alkyl wherein from 0 to 4 carbon atoms are replaced with a a heteroatom selected from O, S, and N, and e) C₂–C₂₀ alkenyl, provided that V is not hydrogen if A¹ is S(O)ₘ and V is not hydrogen if A¹ is a bond, n is 0 and A² is S(O)ₘ;

W is a heterocycle;

X is a bond, —C(=O)NR¹⁰—, —NR¹⁰C(=O)—, —S(O)ₘ—, —NR¹⁰—, O or —C(=O)—;

m is 0, 1 or 2;

n is 0, 1, 2, 3 or 4;

p is 0, 1, 2, 3 or 4;

q is 0, 1, 2, 3 or 4, provided that q is not 0 when X is —C(=O)NR¹⁰—, —S(O)ₘ—, —NR¹⁰— or O;

r is 0 to 5, provided that r is 0 when V is hydrogen;

s is 1 or 2;

t is 0 or 1; and u is 1 or 2;

or an optical isomer or a pharmaceutically acceptable salt thereof.

A preferred embodiment of the compounds of this invention is illustrated by the following formula:

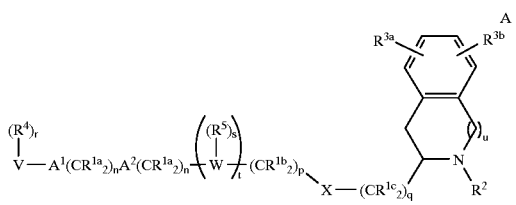

wherein:

$R^{1a}$ and $R^{1c}$ are independently selected from: hydrogen, $C_3$–$C_{10}$ cycloalkyl, $R^8O$—, —$N(R^8)_2$, F or $C_1$–$C_6$ alkyl;

$R^{1b}$ is independently selected from:
  a) hydrogen,
  b) unsubstituted or substituted aryl, unsubstituted or substituted heterocycle, $C_3$–$C_6$ cycloalkyl, $R^8O$—, —$N(R^8)_2$ or $C_2$–$C_6$ alkenyl,
  c) $C_1$–$C_6$ alkyl unsubstituted or substituted by unsubstituted or substituted aryl, heterocycle, $C_3$–$C_6$ cycloalkyl, $C_2$–$C_6$ alkenyl, $R^8O$—, or —$N(R^8)_2$;

$R^2$ is selected from:
  a) $C_{1-8}$ alkyl, unsubstituted or substituted with one or more of:
    1) aryl or heterocycle, unsubstituted or substituted with:
      i) $C_{1-4}$ alkyl,
      ii) $(CH_2)_pOR^6$,
      iii) $(CH_2)_pNR^6R^7$,
      iv) halogen,
      v) $C_{1-4}$ perfluoroalkyl,
    2) $OR^6$,
    3) $SR^6$, $SO_2R^6$, or
    4) 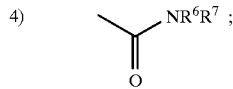
  c) aryl, unsubstituted or substituted with one or more of:
    1) $C_{1-8}$ alkyl,
    2) $C_{1-8}$ perfluoroalkyl,
    3) $OR^6$,
    4) $SR^6$, $SO_2R^6$, or
    5) 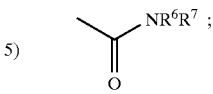
  d) 

-continued e) 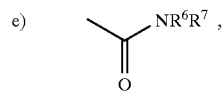

f) $(CH_2)_pR11$, and g) 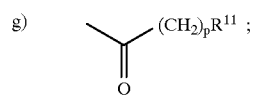

$R^{3a}$ and $R^{3b}$ are independently selected from:
  a) hydrogen,
  b) unsubstituted or substituted aryl, unsubstituted or substituted heterocycle, unsubstituted or substituted $C_3$–$C_{10}$ cycloalkyl, unsubstituted or substituted $C_2$–$C_6$ alkenyl, $C_2$–$C_6$ alkynyl, halogen, $C_1$–$C_6$ perfluoroalkyl, $R^8O$—, $R^9S(O)_m$—, $R^8C(O)NR^8$—, $(R^8)_2NC(O)$—, $R^9C(O)O$—, $R^8_2N$—$C(NR^8)$—, CN, $NO_2$, $R^8C(O)$—, $N_3$, —$N(R^8)_2$, or $R^9OC(O)NR^8$—,
  c) unsubstituted $C_1$–$C_6$ alkyl,
  d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^8O$—, $R^9S(O)_m$—, $R^8C(O)NR^8$—, $(R^8)_2NC(O)$—, $R^8_2N$—$C(NR^8)$—, CN, $R^8C(O)$—, $N_3$, —$N(R^8)_2$, and $R^9OC(O)$—$NR^8$—;

$R^4$ is independently selected from:
  a) hydrogen,
  b) $C_1$–$C_6$ alkyl, $C_2$–$C_6$ alkenyl, $C_2$–$C_6$ alkynyl, $C_1$–$C_6$ perfluoroalkyl, F, Cl, $R^8O$—, $R^8C(O)NR^8$—, CN, $NO_2$, $(R^8)_2N$—$C(NR^8)$—, $R^8C(O)$—, $R^8OC(O)$—, —$N(R^8)_2$, or $R^9OC(O)NR^8$—, and
  c) $C_1$–$C_6$ alkyl substituted by $C_1$–$C_6$ perfluoroalkyl, $R^8O$—, $R^8C(O)NR^8$—, $(R^8)_2N$—$C(NR^8)$—, $R^8C(O)$—, $R^8OC(O)$—, —$N(R^8)_2$, or $R^9OC(O)NR^8$—;

$R^5$ is selected from:
  a) hydrogen,
  b) $C_2$–$C_6$ alkenyl, $C_2$–$C_6$ alkynyl, $C_3$–$C_6$ cycloalkyl, $C_1$–$C_6$ perfluoroalkyl, F, Cl, $R^8O$—, $R^9S(O)_m$—, $R^8C(O)NR^8$—, CN, $NO_2$, $(R^8)_2N$—$C(NR^8)$—, $R^8C(O)$—, $R^8OC(O)$—, —$N(R^8)_2$, or $R^9OC(O)NR^8$—, and
  c) $C_1$–$C_6$ alkyl unsubstituted or substituted by $C_1$–$C_6$ perfluoroalkyl, F, Cl, $R^8O$—, $R^9S(O)_m$—, $R^8C(O)NR^8$—, CN, $(R^8)_2N$—$C(NR^8)$—, $R^8C(O)$—, $R^8OC(O)$—, —$N(R^8)_2$, or $R^9OC(O)NR^8$—;

$R^6$, $R^7$ and $R^{7a}$ are independently selected from:
  H; $C_{1-4}$ alkyl, $C_{3-6}$ cycloalkyl, aryl, heterocycle, unsubstituted or substituted with:
    a) $C_{1-4}$ alkoxy,
    b) halogen, or
    c) substituted or unsubstituted aryl or substituted or unsubstituted heterocycle, $R^8$ is independently selected from hydrogen, $C_1$–$C_6$ alkyl, benzyl, 2,2,2-trifluoroethyl and aryl;

$R^9$ is independently selected from $C_1$–$C_6$ alkyl and aryl;

$R^{10}$ is selected from: H; $R^8C(O)$—; $R^9S(O)_m$—; unsubstituted or substituted $C_{1-4}$ alkyl, unsubstituted or substituted $C_{3-6}$ cycloalkyl, unsubstituted or substituted heterocycle, unsubstituted or substituted aryl, substituted aroyl, unsubstituted or substituted heteroaroyl, substituted arylsulfonyl, unsubstituted or substituted heteroarylsulfonyl, wherein the substituted group is substituted with one or two substituents selected from:

a) $C_{1-4}$ alkoxy,
b) aryl or heterocycle,
c) halogen,
d) HO, e) 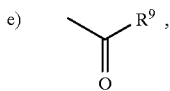

f) 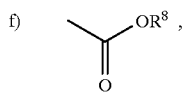

g) $-S(O)_mR^9$
h) $N(R^8)_2$, and
i) $C_{3-6}$ cycloalkyl;

$R^{11}$ is selected from: unsubstituted or substituted aryl, unsubstituted or substituted heterocycle, unsubstituted or substituted pyridinone;

$A^1$ and $A^2$ are independently selected from: a bond, $-CH=CH-$, $-C\equiv C-$, $-C(O)-$, $-C(O)NR^8-$, O, $-N(R^8)-$, or $S(O)_m$;

V is selected from:
a) heterocycle selected from pyrrolidinyl, imidazolyl, pyridinyl, thiazolyl, 2-oxopiperidinyl, indolyl, quinolinyl, isoquinolinyl, and thienyl, and
b) aryl;

W is a heterocycle selected from pyrrolidinyl, imidazolyl, pyridinyl, thiazolyl, pyridonyl, 2-oxopiperidinyl, indolyl, quinolinyl, or isoquinolinyl;

X is a bond, $-C(=O)NR^{10}-$, $-NR^{10}C(=O)-$, $-S(O)_m-$ or $-NR^{10}-$;

m is 0, 1 or 2;
n is 0, 1, 2, 3 or 4;
p is 1, 2 or 3;
q is 0, 1, 2, 3 or 4, provided that q is not 0 when X is $-C(=O)NR^{10}-$, $-S(O)_m-$ or $-NR^{10}-$;
r is 0 to 5, provided that r is 0 when V is hydrogen;
s is 1 or 2;
t is 1; and
u is 1 or 2;

or an optical isomer or a pharmaceutically acceptable salt thereof.

Another preferred embodiment of the compounds of this invention are illustrated by the formula B:

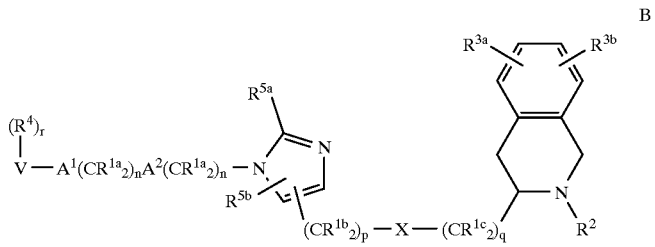

wherein:
$R^{1a}$ and $R^{1c}$ are independently selected from: hydrogen, $C_3-C_{10}$ cycloalkyl, $R^8O-$, $-N(R^8)_2$, F or $C_1-C_6$ alkyl;
$R^{1b}$ is independently selected from:
a) hydrogen,
b) aryl, heterocycle, $C_3-C_{10}$ cycloalkyl, $R^8O-$, $-N(R^8)_2$, F or $C_2-C_6$ alkenyl,
c) unsubstituted or substituted $C_1-C_6$ alkyl wherein the substituent on the substituted $C_1-C_6$ alkyl is selected from unsubstituted or substituted aryl, heterocycle, $C_3-C_{10}$ cycloalkyl, $C_2-C_6$ alkenyl, $R^8O-$ and $-N(R^8)_2$;

$R^2$ is selected from: H; unsubstituted or substituted $C_{1-8}$ alkyl, unsubstituted or substituted $C_{2-8}$ alkenyl, unsubstituted or substituted aryl, unsubstituted or substituted heterocycle, $(CH_2)_pR^{11}$,

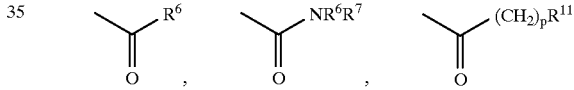

and $-S(O)_2R^6$, wherein the substituted group is substituted with one or more of:
1) aryl or heterocycle, unsubstituted or substituted with one or two groups selected from:
   a) $C_{1-4}$ alkyl,
   b) $(CH_2)_pOR^6$,
   c) $(CH_2)_pNR^6R^7$,
   d) halogen,
   e) $C_{1-4}$ perfluoroalkyl,
2) $C_{3-6}$ cycloalkyl,
3) $OR^6$,
4) $SR^6$, $S(O)R^6$, $SO_2R^6$,
5) $-NR^6R^7$ 6) 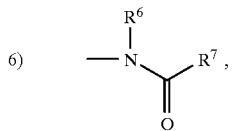

7) 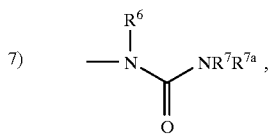

8) 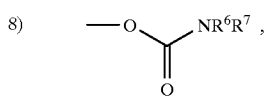

9) 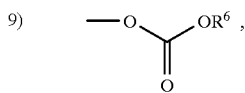

10) 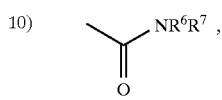

11) —SO$_2$—NR$^6$R$^7$,

12) 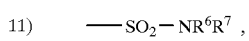

13) 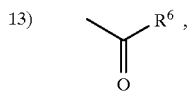

14) 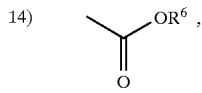

15) C$_{1-8}$ alkyl, or
16) C$_{1-8}$ perfluoroalkyl;

R$^{3a}$ and R$^{3b}$ are independently selected from:
a) hydrogen,
b) unsubstituted or substituted aryl, unsubstituted or substituted heterocycle, unsubstituted or substituted C$_3$–C$_{10}$ cycloalkyl, unsubstituted or substituted C$_2$–C$_6$ alkenyl, C$_2$–C$_6$ alkynyl, halogen, C$_1$–C$_6$ perfluoroalkyl, R$^8$O—, R$^9$S(O)$_m$—, R$^8$C(O)NR$^8$—, (R$^8$)$_2$NC(O)—, R$^9$C(O)O—, R$^8$$_2$N—C(NR$^8$)—, CN, NO$_2$, R$^8$C(O)—, N$_3$, —N(R$^8$)$_2$, or R$^9$OC(O)NR$^8$—,
c) unsubstituted C$_1$–C$_6$ alkyl,
d) substituted C$_1$–C$_6$ alkyl wherein the substituent on the substituted C$_1$–C$_6$ alkyl is selected from unsubstituted or substituted aryl, unsubstituted or substituted heterocyclic, C$_3$–C$_{10}$ cycloalkyl, C$_2$–C$_6$ alkenyl, C$_2$–C$_6$ alkynyl, R$^8$O—, R$^9$S(O)$_m$—, R$^8$C(O)NR$^8$—, (R$^8$)$_2$NC(O)—, R$^8$$_2$N—C(NR$^8$)—, CN, R$^8$C(O)—, N$_3$, —N(R$^8$)$_2$, and R$^9$OC(O)—NR$^8$—;

R$^4$ is independently selected from:
a) hydrogen,
b) aryl, substituted aryl, heterocycle, substituted heterocycle, C$_1$–C$_6$ alkyl, C$_2$–C$_6$ alkenyl, C$_2$–C$_6$ alkynyl, C$_1$–C$_6$ perfluoroalkyl, F, Cl, R$^8$O—, R$^8$C(O)NR$^8$—, CN, NO$_2$, (R$^8$)$_2$N—C(NR$^8$)—, R$^8$C(O)—, —N(R$^8$)$_2$, or R$^9$OC(O)NR$^8$—, and c) C$_1$–C$_6$ alkyl substituted by C$_1$–C$_6$ perfluoroalkyl, R$^8$O—, R$^8$C(O)NR$^8$—, (R$^8$)$_2$N—C(NR$^8$)—, R$^8$C(O)—, —N(R$^8$)$_2$, or R$^9$OC(O)NR$^8$—;

R$^{5a}$ and R$^{5b}$ are independently hydrogen, C$_1$–C$_6$ alkyl, cyclopropyl, trifluoromethyl and halogen;

R$^6$, R$^7$ and R$^{7a}$ are independently selected from:
H; C$_{1-4}$ alkyl, C$_{3-6}$ cycloalkyl, aryl, heterocycle, unsubstituted or substituted with:
a) C$_{1-4}$ alkoxy,
b) halogen, or
c) substituted or unsubstituted aryl or substituted or unsubstituted heterocycle, R$^8$ is independently selected from hydrogen, C$_1$–C$_6$ alkyl, 2,2,2-trifluoroethyl, benzyl and aryl;

R$^9$ is independently selected from C$_1$–C$_6$ alkyl and aryl;

R$^{10}$ is selected from: H; R$^8$C(O)—; R$^9$S(O)$_m$—; unsubstituted or substituted C$_{1-4}$ alkyl, unsubstituted or substituted C$_{3-6}$ cycloalkyl, unsubstituted or substituted heterocycle, unsubstituted or substituted aryl, substituted aroyl, unsubstituted or substituted heteroaroyl, substituted arylsulfonyl, unsubstituted or substituted heteroarylsulfonyl, wherein the substituted group is substituted with one or two substituents selected from:
a) C$_{1-4}$ alkoxy,
b) aryl or heterocycle,
c) halogen,
d) HO, e) 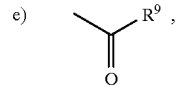

f) 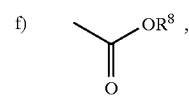

g) —S(O)$_m$R$^9$,
h) N(R$^8$)$_2$, and
i) C$_{3-6}$ cycloalkyl;

R$^{11}$ is selected from: unsubstituted or substituted aryl, unsubstituted or substituted heterocycle, unsubstituted or substituted pyridinone, wherein the substituents on the cyclic group are selected from: halogen, —OH, and —O(C$_1$–C$_6$ alkyl);

A$^1$ and A$^2$ are independently selected from: a bond, —CH=CH—, —C≡C—, —C(O)—, —C(O)NR$^8$—, O, —N(R$^8$)—, or S(O)$_m$;

V is selected from:
a) hydrogen,
b) heterocycle selected from pyrrolidinyl, imidazolyl, imidazolinyl, pyridinyl, thiazolyl, 2-oxopiperidinyl, oxazolyl, indolyl, quinolinyl, isoquinolinyl, triazolyl and thienyl,
c) aryl,
d) C$_1$–C20 alkyl wherein from 0 to 4 carbon atoms are replaced with a a heteroatom selected from O, S, and N, and
e) C$_2$–C$_{20}$ alkenyl, and
provided that V is not hydrogen if A$^1$ is S(O)$_m$ and V is not hydrogen if A$^1$ is a bond, n is 0 and A$^2$ is S(O)$_m$;

X is a bond, —C(=O)NR$^{10}$—, —NR$^{10}$C(=O)—, —S(O)$_m$— or —NR$^{10}$—;

m is 0, 1 or 2;

n is 0, 1, 2, 3 or 4;
p is 0, 1, 2, 3 or 4;
q is 0, 1, 2, 3 or 4, provided that q is not 0 when X is
—C(=O)NR$^{10}$—, —S(O)$_m$— or —NR$^{10}$—; and
r is 0 to 5, provided that r is 0 when V is hydrogen;
or an optical isomer or pharmaceutically acceptable salt thereof.

Another preferred embodiment of the compounds of this invention are illustrated by the formula C:

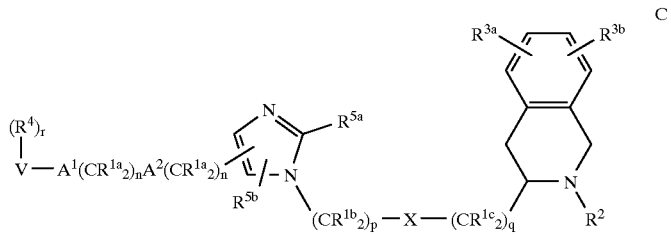

wherein:

R$^{1a}$ and R$^{1c}$ are independently selected from: hydrogen, C$_3$–C$_{10}$ cycloalkyl, R$^8$O—, —N(R$^8$)$_2$, F or C$_1$–C$_6$ alkyl;

R$^{1b}$ is independently selected from:

a) hydrogen, b) aryl, heterocycle, C$_3$–C$_{10}$ cycloalkyl, R$^8$O—, —N(R$^8$)$_2$, F or C$_2$–C$_6$ alkenyl, c) unsubstituted or substituted C$_1$–C$_6$ alkyl wherein the substituent on the substituted C$_1$–C$_6$ alkyl is selected from unsubstituted or substituted aryl, heterocycle, C$_3$–C$_{10}$ cycloalkyl, C$_2$–C$_6$ alkenyl, R$^8$O— and —N(R8)$_2$;

R$^2$ is selected from: H; unsubstituted or substituted C$_{1-8}$ alkyl, unsubstituted or substituted C$_{2-8}$ alkenyl, unsubstituted or substituted aryl, unsubstituted or substituted heterocycle, (CH$_2$)$_p$R$^{11}$,

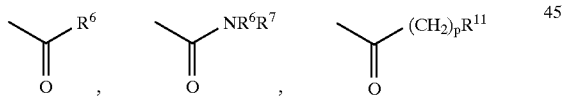

and —S(O)$_2$R$^6$, wherein the substituted group is substituted with one or more of:

1) aryl or heterocycle, unsubstituted or substituted with one or two groups selected from:
   a) C$_{1-4}$ alkyl,
   b) (CH$_2$)$_p$OR$^6$,
   c) (CH$_2$)$_p$NR$^6$R$^7$,
   d) halogen,
   e) C$_{1-4}$ perfluoroalkyl,
2) C$_{3-6}$ cycloalkyl,
3) OR$^6$,
4) SR$^6$, S(O)R$^6$, SO$_2$R$^6$,

5) —NR$^6$R$^7$

6) 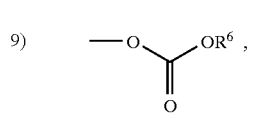

7) —N(R$^6$)—C(=O)—NR$^7$R$^{7a}$ ,

8) —O—C(=O)—NR$^6$R$^7$ ,

9) —O—C(=O)—OR$^6$ ,

10) 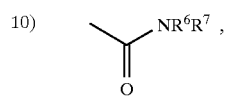

11) —SO$_2$—NR$^6$R$^7$ ,

12) 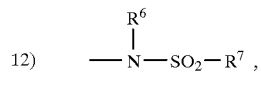

-continued

13) 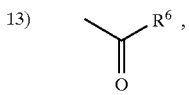

14) 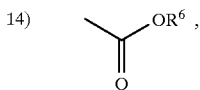

15) $C_{1-8}$ alkyl, or
16) $C_{1-8}$ perfluoroalkyl;

$R^{3a}$ and $R^{3b}$ are independently selected from:

a) hydrogen, b) unsubstituted or substituted aryl, unsubstituted or substituted heterocycle, unsubstituted or substituted $C_{3-C10}$ cycloalkyl, unsubstituted or substituted $C_2-C_6$ alkenyl, $C_2-C_6$ alkynyl, halogen, $C_1-C_6$ perfluoroalkyl, $R^8O-$, $R^9S(O)_m-$, $R^8C(O)NR^8-$, $(R^8)_2NC(O)-$, $R^9C(O)O-$, $R^8{}_2N-C(NR^8)-$, CN, NO$_2$, $R^8C(O)-$, N$_3$, $-N(R^8)_2$, or $R^9OC(O)NR^8-$, c) unsubstituted $C_1-C_6$ alkyl, d) substituted $C_1-C_6$ alkyl wherein the substituent on the substituted $C_1-C_6$ alkyl is selected from unsubstituted or substituted aryl, unsubstituted or substituted heterocyclic, $C_3-C_{10}$ cycloalkyl, $C_2-C_6$ alkenyl, $C_2-C_6$ alkynyl, $R^8O-$, $R^9S(O)_m-$, $R^8C(O)NR^8-$, $(R^8)_2NC(O)-$, $R^8{}_2N-C(NR^8)-$, CN, $R^8C(O)-$, N$_3$, $-N(R^8)_2$, and $R^9OC(O)-NR^8-$;

$R^4$ is independently selected from:

a) hydrogen, b) aryl, substituted aryl, heterocycle, substituted heterocycle, $C_1-C_6$ alkyl, $C_2-C_6$ alkenyl, $C_2-C_6$ alkynyl, $C_1-C_6$ perfluoroalkyl, F, Cl, $R^8O-$, $R^8C(O)NR^8-$, CN, NO$_2$, $(R^8)_2N-C(NR^8)-$, $R^8C(O)-$, $-N(R^8)_2$, or $R^9OC(O)NR^8-$, and c) $C_1-C_6$ alkyl substituted by $C_1-C_6$ perfluoroalkyl, $R^8O-$, $R^8C(O)NR^8-$, $(R^8)_2N-C(NR^8)-$, $R^8C(O)-$, $-N(R^8)_2$, or $R^9OC(O)NR^8-$;

$R^{5a}$ and $R^{5b}$ are independently hydrogen, $C_1-C_6$ alkyl, cyclopropyl, trifluoromethyl and halogen;

$R^6$, $R^7$ and $R^{7a}$ are independently selected from:

H; $C_{1-4}$ alkyl, $C_{3-6}$ cycloalkyl, aryl, heterocycle, unsubstituted or substituted with:

a) $C_{1-4}$ alkoxy,
b) halogen, or
c) substituted or unsubstituted aryl or substituted or unsubstituted heterocycle, $R^8$ is independently selected from hydrogen, $C_1-C_6$ alkyl, 2,2,2-trifluoroethyl, benzyl and aryl;

$R^9$ is independently selected from $C_1-C_6$ alkyl and aryl;

$R^{10}$ is selected from: H; $R^8C(O)-$; $R^9S(O)_m-$; unsubstituted or substituted $C_{1-4}$ alkyl, unsubstituted or substituted $C_{3-6}$ cycloalkyl, unsubstituted or substituted heterocycle, unsubstituted or substituted aryl, substituted aroyl, unsubstituted or substituted heteroaroyl, substituted arylsulfonyl, unsubstituted or substituted heteroarylsulfonyl, wherein the substituted group is substituted with one or two substituents selected from:

a) $C_{1-4}$ alkoxy,
b) aryl or heterocycle,
c) halogen,
d) HO, e) 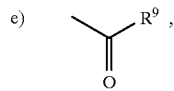

f) 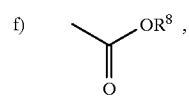

g) $-S(O)_mR^9$,
h) $N(R^8)_2$, and
i) $C_{3-6}$ cycloalkyl;

$R^{11}$ is selected from: unsubstituted or substituted aryl, unsubstituted or substituted heterocycle, unsubstituted or substituted pyridinone, wherein the substituents on the cyclic group are selected from: halogen, $-OH$ and $-O(C_{1-6}$ alkyl);

$A^1$ and $A^2$ are independently selected from: a bond, $-CH=CH-$, $-C\equiv C-$, $-C(O)-$, $-C(O)NR^8-$, O, $-N(R^8)-$, or $S(O)_m$;

V is selected from:

a) hydrogen, b) heterocycle selected from pyrrolidinyl, imidazolyl, imidazolinyl, pyridinyl, thiazolyl, 2-oxopiperidinyl, oxazolyl, indolyl, quinolinyl, isoquinolinyl, triazolyl and thienyl, c) aryl, d) $C_1-C_{20}$ alkyl wherein from 0 to 4 carbon atoms are replaced with a a heteroatom selected from O, S, and N, and e) $C_2-C_{20}$ alkenyl, and provided that V is not hydrogen if $A^1$ is $S(O)_m$ and V is not hydrogen if $A^1$ is a bond, n is 0 and $A^2$ is $S(O)_m$;

X is a bond, $-C(=O)NR^{10}-$, $-NR^{10}C(=O)-$, $-S(O)_m-$ or $-NR^{10}-$;

m is 0, 1 or 2;

n is 0, 1, 2, 3 or 4;

p is 0, 1, 2, 3 or 4, provided that p is not 0 if X is a bond, $-NR^8-$ or O;

q is 0, 1, 2, 3 or 4, provided that q is not 0 when X is $-C(=O)NR^{10}-$, $-S(O)_m-$ or $-NR^{10}-$; and r is 0 to 5, provided that r is 0 when V is hydrogen;

or an optical isomer or pharmaceutically acceptable salt thereof.

In a more preferred embodiment of this invention, the inhibitors of farnesyl-protein transferase are illustrated by the formula D:

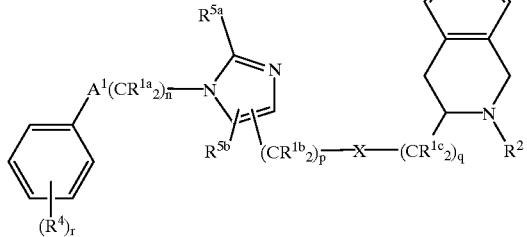

wherein:

$R^{1a}$ and $R^{1c}$ are independently selected from: hydrogen, $C_3$–$C_{10}$ cycloalkyl or $C_1$–$C_6$ alkyl;

$R^{1b}$ is independently selected from:
 a) hydrogen,
 b) aryl, heterocycle, $C_3$–$C_{10}$ cycloalkyl, $R^8O$—, —$N(R^8)_2$, F or $C_2$–$C_6$ alkenyl,
 c) $C_1$–$C_6$ alkyl unsubstituted or substituted by aryl, heterocycle, $C_3$–$C_{10}$ cycloalkyl, $C_2$–$C_6$ alkenyl, $R^8O$—, or —$N(R^8)_2$;

$R^2$ is selected from: H; unsubstituted or substituted $C_{1-8}$ alkyl, unsubstituted or substituted aryl, $(CH_2)_pR^{11}$,

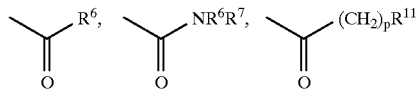

and —$S(O)_2R^6$, wherein the substituted group is substituted with one or more of:
 1) aryl or heterocycle, unsubstituted or substituted with one or two groups selected from:
  a) $C_{1-4}$ alkyl,
  b) $(CH_2)_pOR^6$,
  c) $(CH_2)_pNR^6R^7$,
  d) halogen,
  e) $C_{1-4}$ perfluoroalkyl,
 2) $C_{3-6}$ cycloalkyl,
 3) $OR^6$,
 4) $SR^6$, $S(O)R^6$, $SO_2R^6$,
 5) —$NR^6R^7$ 6) 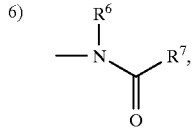

7) 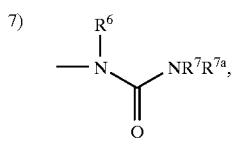

8) 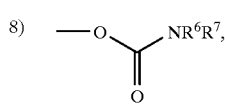

9) 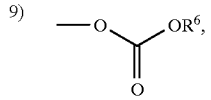

10) 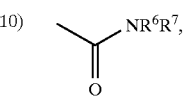

11) —$SO_2$—$NR^6R^7$,

12) 

13) 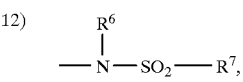

14) 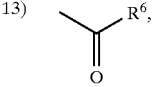

15) $C_{1-8}$ alkyl, or
 16) $C_{1-8}$ perfluoroalkyl;

$R^{3a}$ and $R^{3b}$ are independently selected from:
 a) hydrogen,
 b) unsubstituted or substituted aryl, unsubstituted or substituted heterocycle, unsubstituted or substituted $C_3$–$C_{10}$ cycloalkyl, unsubstituted or substituted $C_2$–$C_6$ alkenyl, $C_2$–$C_6$ alkynyl, halogen, $C_1$–$C_6$ perfluoroalkyl, $R^8O$—, $R^9S(O)_m$—, $R^8C(O)NR^8$—, $(R^8)_2NC(O)$—, $R^9C(O)O$—, $R^8_2N$—$C(NR^8)$—, CN, $NO_2$, $R^8C(O)$—, $N_3$, —$N(R^8)_2$, or $R^9OC(O)NR^8$—,
 c) unsubstituted $C_1$–$C_6$ alkyl,
 d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^8O$—, $R^9S(O)_m$—, $R^8C(O)NR^8$—, $(R^8)_2NC(O)$—, $R^8_2N$—$C(NR^8)$—, CN, $R^8C(O)$—, $N_3$, —$N(R^8)_2$, and $R^9OC(O)$—$NR^8$—;

$R^4$ is independently selected from:
 a) hydrogen,
 b) aryl, substituted aryl, heterocycle, substituted heterocycle, $C_1$–$C_6$ alkyl, $C_2$–$C_6$ alkenyl, $C_2$–$C_6$ alkynyl, $C_1$–$C_6$ perfluoroalkyl, F, Cl, $R^8O$—, $R^8C(O)NR^8$—, CN, $NO_2$, $(R^8)_2N$—$C(NR^8)$—, $R^8C(O)$—, —$N(R^8)_2$, or $R^9OC(O)NR^8$—, and
 c) $C_1$–$C_6$ alkyl substituted by $C_1$–$C_6$ perfluoroalkyl, $R^8O$—, $R^8C(O)NR^8$—, $(R^8)_2N$—$C(NR^8)$—, $R^8C(O)$—, —$N(R^8)_2$, or $R^9OC(O)NR^8$—;

$R^{5a}$ and $R^{5b}$ are independently hydrogen, ethyl, cyclopropyl or methyl;

$R^6$, $R^7$ and $R^{7a}$ are independently selected from:
 H; $C_{14}$ alkyl, $C_{3-6}$ cycloalkyl, aryl, heterocycle, unsubstituted or substituted with:
  a) $C_{1-4}$ alkoxy,
  b) halogen, or
  c) substituted or unsubstituted aryl or substituted or unsubstituted heterocycle, $R^8$ is independently selected from hydrogen, $C_1$–$C_6$ alkyl, 2,2,2-trifluoroethyl, benzyl and aryl;

$R^9$ is independently selected from $C_1$–$C_6$ alkyl and aryl;

$R^{10}$ is selected from: H; $R^8C(O)$—; $R^9S(O)_m$—; unsubstituted or substituted $C_{1-4}$ alkyl, wherein the substituted alkyl group is substituted with one or two substituents selected from:
 a) $C_{1-4}$ alkoxy,
 b) aryl or heterocycle,
 c) halogen,
 d) HO,
 e) 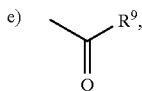
 f) 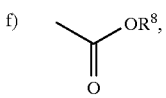
 g) —S(O)$_m$R$^9$,
 h) N(R$^8$)$_2$, and
 i) $C_{3-6}$ cycloalkyl;

$R^{11}$ is selected from: unsubstituted or substituted aryl, unsubstituted or substituted heterocycle, unsubstituted or substituted pyridinone, wherein the substituents on the cyclic group are selected from: halogen, —OH and —O($C_{1-6}$ alkyl);

$A^1$ is selected from: a bond, —C(O)—, O, —N(R$^8$)—, or S(O)$_m$;

X is a bond, —C(=O)NR$^{10}$—, —NR$^{10}$C(=O)—, —S(O)$_m$— or —NR$^{10}$—;

n is 0 or 1; provided that n is not 0 if $A^1$ is a bond, O, —N(R$^8$)—, or S(O)$_m$;

m is 0, 1 or 2;

p is 0, 1, 2, 3 or 4;

q is 0, 1, 2, 3 or 4, provided that q is not 0 when X is —C(=O)NR$^{10}$—, —S(O)$_m$— or —NR$^{10}$—; and r is 0, 1 or 2;

or an optical isomer or pharmaceutically acceptable salt thereof.

In another more preferred embodiment of this invention, the inhibitors of farnesyl-protein transferase are illustrated by the formula E:

wherein:
$R^{1a}$ and $R^{1c}$ are independently selected from: hydrogen, $R^8O$—, —N(R$^8$)$_2$, F, $C_3$–$C_{10}$ cycloalkyl or $C_1$–$C_6$ alkyl;
$R^{1b}$ is independently selected from:
 a) hydrogen,
 b) aryl, heterocycle, $C_3$–$C_{10}$ cycloalkyl, R$^8$O—, —N(R$^8$)$_2$, F or $C_2$–$C_6$ alkenyl,
 c) $C_1$–$C_6$ alkyl unsubstituted or substituted by aryl, heterocycle, $C_3$–$C_{10}$ cycloalkyl, $C_2$–$C_6$ alkenyl, R$^8$O—, or —N(R$^8$)$_2$;

$R^2$ is selected from: H; unsubstituted or substituted $C_{1-8}$ alkyl, unsubstituted or substituted aryl,

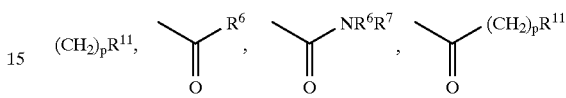

and —S(O)$_2$R$^6$, wherein the substituted group is substituted with one or more of:
 1) aryl or heterocycle, unsubstituted or substituted with one or two groups selected from:
  a) $C_{1-4}$ alkyl,
  b) (CH$_2$)$_p$OR$^6$,
  c) (CH$_2$)$_p$NR$^6$R$^7$,
  d) halogen,
  e) $C_{14}$ perfluoroalkyl,
 2) $C_{3-6}$ cycloalkyl,
 3) OR$^6$,
 4) SR$^6$, S(O)R$^6$, SO$_2$R$^6$,
 5) —NR$^6$R$^7$,
 6) 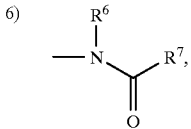
 7) 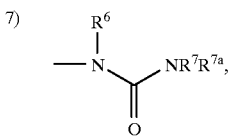

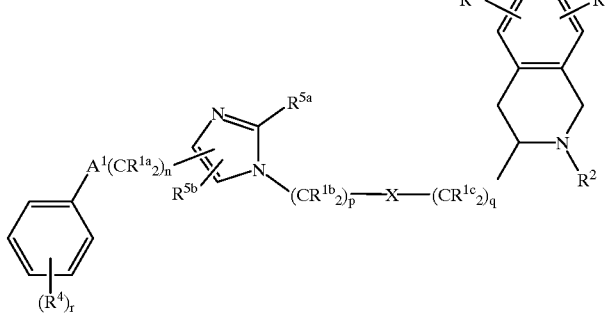

-continued

8) 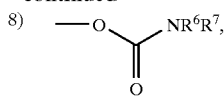

9) 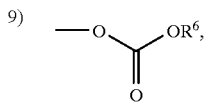

10) 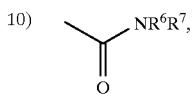

11) —SO$_2$—NR$^6$R$^7$, 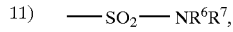

12) 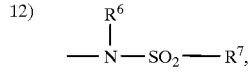

13) 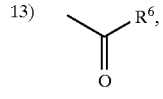

14) 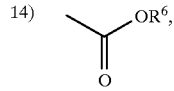

15) $C_{1-8}$ alkyl, or
16) $C_{1-8}$ perfluoroalkyl;

$R^{3a}$ and $R^{3b}$ are independently selected from:
a) hydrogen,
b) unsubstituted or substituted aryl, unsubstituted or substituted heterocycle, unsubstituted or substituted $C_3$–$C_{10}$ cycloalkyl, unsubstituted or substituted $C_2$–$C_6$ alkenyl, $C_2$–$C_6$ alkynyl, halogen, $C_1$–$C_6$ perfluoroalkyl, $R^8O$—, $R^9S(O)_m$—, $R^8C(O)NR^8$—, $(R^8)_2NC(O)$—, $R^9C(O)O$—, $R^8{}_2N$—$C(NR^8)$—, CN, NO$_2$, $R^8C(O)$—, N$_3$, —N($R^8)_2$, or $R^9OC(O)NR^8$—,
c) unsubstituted $C_1$–$C_6$ alkyl,
d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^8O$—, $R^9S(O)_m$—, $R^8C(O)NR^8$—, $(R^8)_2NC(O)$—, $R^8{}_2N$—$C(NR^8)$—, CN, $R^8C(O)$—, N$_3$, —N($R^8)_2$, and $R^9OC(O)$—$NR^8$—;

$R^4$ is independently selected from:
a) hydrogen,
b) aryl, substituted aryl, heterocycle, substituted heterocycle, $C_1$–$C_6$ alkyl, $C_2$–$C_6$ alkenyl, $C_2$–$C_6$ alkynyl, $C_1$–$C_6$ perfluoroalkyl, F, Cl, $R^8O$—, $R^8C(O)NR^8$—, CN, NO$_2$, $(R^8)_2N$—$C(NR^8)$—, $R^8C(O)$—, —N(R8)$_2$, or $R^9OC(O)NR^8$—, and
c) $C_1$–$C_6$ alkyl substituted by $C_1$–$C_6$ perfluoroalkyl, $R^8O$—, $R^8C(O)NR^8$—, $(R^8)_2N$—$C(NR^8)$—, $R^8C(O)$—, —N($R^8)_2$, or $R^9OC(O)NR^8$—;

$R^{5a}$ and $R^{5b}$ are independently hydrogen, ethyl, cyclopropyl or methyl;

$R^6$, $R^7$ and $R^{7a}$ are independently selected from:
H; $C_{1-4}$ alkyl, $C_{3-6}$ cycloalkyl, aryl, heterocycle, unsubstituted or substituted with:
a) $C_{1-4}$ alkoxy,
b) halogen, or
c) substituted or unsubstituted aryl or substituted or unsubstituted heterocycle, $R^8$ is independently selected from hydrogen, $C_1$–$C_6$ alkyl, 2,2,2-trifluoroethyl, benzyl and aryl;
$R^9$ is independently selected from $C_1$–$C_6$ alkyl and aryl;
$R^{10}$ is selected from: H; $R^8C(O)$—; $R^9S(O)_m$—; unsubstituted or substituted $C_{1-4}$ alkyl, wherein the substituted alkyl group is substituted with one or two substituents selected from:
a) $C_{1-4}$ alkoxy,
b) aryl or heterocycle,
c) halogen,
d) HO, e) 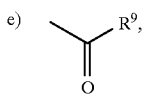

f) 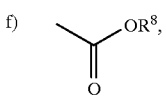

g) —S(O)$_m$R$^9$, 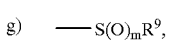

h) N($R^8)_2$, and
i) $C_{3-6}$ cycloalkyl;

$R^{11}$ is selected from: unsubstituted or substituted aryl, unsubstituted or substituted heterocycle, unsubstituted or substituted pyridinone, wherein the substituents on the cyclic group are selected from: halogen, —OH and —O($C_{1-6}$ alkyl);

X is a bond, —C(=O)NR$^{10}$—, —NR$^{10}$C(=O)—, —S(O)$_m$— or —NR$^{10}$—;

n is 0 or 1;

m is 0, 1 or 2;

p is 0, 1, 2, 3 or 4, provided that p is not 0 if X is a bond, —NR$^8$— or O;

q is 0, 1, 2, 3 or 4, provided that q is not 0 when X is —C(=O)NR$^{10}$—, —S(O)$_m$— or —NR$^{10}$—; and r is 0, 1 or 2;

or an optical isomer or pharmaceutically acceptable salt thereof.

In a further embodiment of this invention, the inhibitors of farnesyl-protein transferase are illustrated by the formula F:

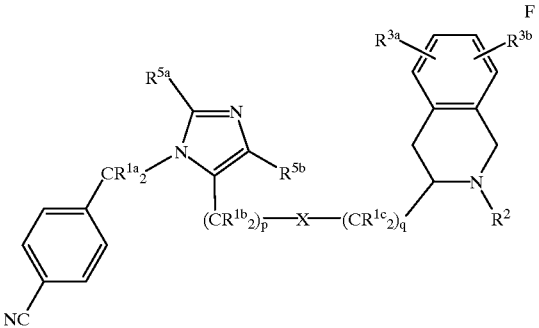

wherein:
$R^{1a}$ and $R^{1c}$ are independently selected from: hydrogen, $C_3$–$C_{10}$ cycloalkyl or $C_1$–$C_6$ alkyl;
$R^{1b}$ is independently selected from:
a) hydrogen,
b) aryl, heterocycle, $C_3$–$C_{10}$ cycloalkyl, $R^8O$—, —N($R^8)_2$ or F, c) $C_1-C_6$ alkyl unsubstituted or substituted by aryl, heterocycle, $C_3-C_{10}$ cycloalkyl, $R^8O-$, or $-N(R^8)_2$;

$R^2$ is selected from: H; unsubstituted or substituted $C_{1-8}$ alkyl, unsubstituted or substituted aryl, $(CH_2)_pR^{11}$,

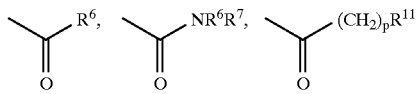

and $-S(O)_2R^6$, wherein the substituted group is substituted with one or more of:
1) aryl or heterocycle, unsubstituted or substituted with one or two groups selected from:
   a) $C_{1-4}$ alkyl,
   b) $(CH_2)_pOR^6$,
   c) $(CH_2)_pNR^6R^7$,
   d) halogen,
   e) $C_{1-4}$ perfluoroalkyl,
2) $C_{3-6}$ cycloalkyl,
3) $OR^6$,
4) $SR^6$, $S(O)R^6$, $SO_2R^6$
5) $-NR^6R^7$, 6) 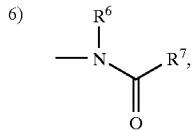

7) 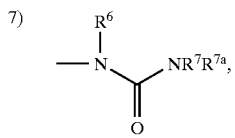

8) 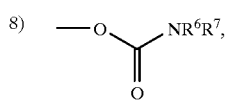

9) 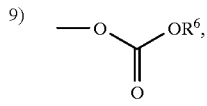

10) 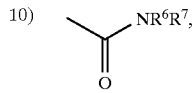

11) $-SO_2-NR^6R^7$,

12) 

13) 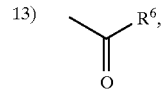

14) 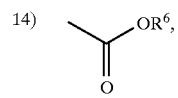

15) $C_{1-8}$ alkyl, or
16) $C_{1-8}$ perfluoroalkyl;

$R^{3a}$ and $R^{3b}$ are independently selected from:
a) hydrogen,
b) unsubstituted or substituted aryl, unsubstituted or substituted heterocycle, unsubstituted or substituted $C_3-C_{10}$ cycloalkyl, unsubstituted or substituted $C_2-C_6$ alkenyl, $C_2-C_6$ alkynyl, halogen, $C_1-C_6$ perfluoroalkyl, $R^8O-$, $R^9S(O)_m-$, $R^8C(O)NR^8-$, $(R^8)_2NC(O)-$, $R^9C(O)O-$, $R^8{}_2N-C(NR^8)-$, CN, $NO_2$, $R^8C(O)-$, $N_3$, $-N(R^8)_2$, or $R^9OC(O)NR^8-$,
c) unsubstituted $C_1-C_6$ alkyl,
d) substituted $C_1-C_6$ alkyl wherein the substituent on the substituted $C_1-C_6$ alkyl is selected from unsubstituted or substituted aryl, unsubstituted or substituted heterocyclic, $C_3-C_{10}$ cycloalkyl, $C_2-C_6$ alkenyl, $C_2-C_6$ alkynyl, $R^8O-$, $R^9S(O)_m-$, $R^8C(O)NR^8-$, $(R^8)_2NC(O)-$, $R^8{}_2N-C(NR^8)-$, CN, $R^8C(O)-$, $N_3$, $-N(R^8)_2$, and $R^9OC(O)-NR^8-$;

$R^{5a}$ and $R^{5b}$ are independently hydrogen, ethyl, cyclopropyl or methyl;

$R^6$, $R^7$ and $R^{7a}$ are independently selected from:
H; $C_{1-4}$ alkyl, $C_{3-6}$ cycloalkyl, aryl, heterocycle, unsubstituted or substituted with:
a) $C_{1-4}$ alkoxy,
b) halogen, or
c) substituted or unsubstituted aryl or substituted or unsubstituted heterocycle, $R^8$ is independently selected from hydrogen, $C_1-C_6$ alkyl, 2,2,2-trifluoroethyl, benzyl and aryl;

$R^9$ is independently selected from $C_1-C_6$ alkyl and aryl;

$R^{10}$ is selected from: H; $R^8C(O)-$; $R^9S(O)_m-$; unsubstituted or substituted $C_{1-4}$ alkyl, wherein the substituted alkyl group is substituted with one or two substituents selected from:
a) $C_{1-4}$ alkoxy,
b) aryl or heterocycle,
c) halogen,
d) HO, e) 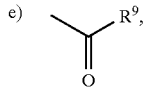

f) 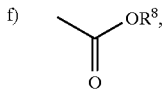

g) $-S(O)_mR^9$,
h) $N(R^8)_2$, and
i) $C_{3-6}$ cycloalkyl;

$R^{11}$ is selected from: unsubstituted or substituted aryl, unsubstituted or substituted heterocycle, unsubstituted or substituted pyridinone, wherein the substituents on the cyclic group are selected from: halogen, $-OH$ and $-O(C_{1-6}$ alkyl);

X is a bond, $-C(=O)NR^{10}-$, $-NR^{10}C(=O)-$, $-S(O)_m-$ or $-NR^{10}-$;

m is 0, 1 or 2;

p is 0, 1, 2, 3 or 4; and q is 0, 1, 2, 3 or 4, provided that q is not 0 when X is $-C(=O)NR^{10}-$, $-S(O)_m-$ or $-NR^{10}-$;

or an optical isomer or pharmaceutically acceptable salt thereof.

In a further embodiment of this invention, the inhibitors of farnesyl-protein transferase are illustrated by the formula G:

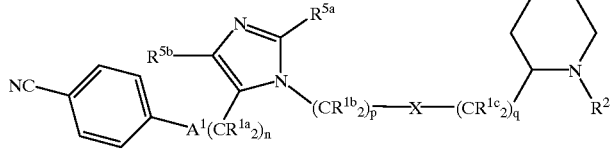

wherein:

$R^{1a}$ and $R^{1c}$ are independently selected from: hydrogen, $R^8O-$, $-N(R^8)_2$, F, $C_3-C_{10}$ cycloalkyl or $C_1-C_6$ alkyl;

$R^{1b}$ is independently selected from:

a) hydrogen, b) aryl, heterocycle or $C_3-C_{10}$ cycloalkyl, c) $C_1-C_6$ alkyl unsubstituted or substituted by aryl, heterocycle, $C_3-C_{10}$ cycloalkyl, $C_2-C_6$ alkenyl, $R^8O-$, or $-N(R^8)_2$;

$R^2$ is selected from: H; unsubstituted or substituted $C_{1-8}$ alkyl, unsubstituted or substituted aryl, $(CH_2)_pR^{11}$,

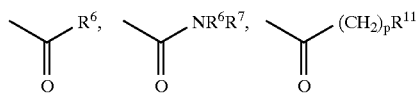

and $-S(O)_2R^6$, wherein the substituted group is substituted with one or more of:

1) aryl or heterocycle, unsubstituted or substituted with one or two groups selected from:
   a) $C_{1-4}$ alkyl,
   b) $(CH_2)_pOR^6$,
   c) $(CH_2)_pNR^6R^7$,
   d) halogen,
   e) $C_{1-4}$ perfluoroalkyl,
2) $C_{3-6}$ cycloalkyl,
3) $OR^6$,
4) $SR^6$, $S(O)R^6$, $SO_2R^6$,
5) $-NR^6R^7$, 6) 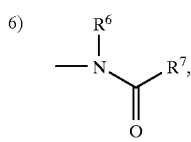

7) 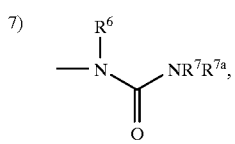

8) 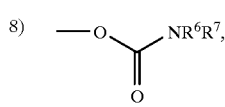

9) 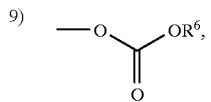

10) 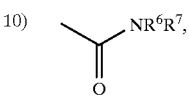

11) $-SO_2-NR^6R^7$,

12) 

13) 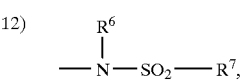

14) 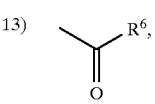

15) $C_{1-8}$ alkyl, or
16) $C_{1-8}$ perfluoroalkyl;

$R^{3a}$ and $R^{3b}$ are independently selected from:

a) hydrogen, b) unsubstituted or substituted aryl, unsubstituted or substituted heterocycle, unsubstituted or substituted $C_3-C_{10}$ cycloalkyl, unsubstituted or substituted $C_2-C_6$ alkenyl, $C_2-C_6$ alkynyl, halogen, $C_1-C_6$ perfluoroalkyl, $R^8O-$, $R^9S(O)_m-$, $R^8C(O)NR^8-$, $(R^8)_2NC(O)-$, $R^9C(O)O-$, $R^8_2N-C(NR^8)-$, CN, $NO_2$, $R^8C(O)-$, $N_3$, $-N(R^8)_2$, or $R^9OC(O)NR^8-$, c) unsubstituted $C_1-C_6$ alkyl, d) substituted $C_1-C_6$ alkyl wherein the substituent on the substituted $C_1-C_6$ alkyl is selected from unsubstituted or substituted aryl, unsubstituted or substituted heterocyclic, $C_3-C_{10}$ cycloalkyl, $C_2-C_6$ alkenyl, $C_2-C_6$ alkynyl, $R^8O-$, $R^9S(O)_m-$, $R^8C(O)NR^8-$, $(R^8)_2NC(O)-$, $R^8_2N-C(NR^8)-$, CN, $R^8C(O)-$, $N_3$, $-N(R^8)_2$, and $R^9OC(O)-NR^8-$;

$R^{5a}$ and $R^{5b}$ are independently hydrogen, ethyl, cyclopropyl or methyl;

$R^6$, $R^7$ and $R^{7a}$ are independently selected from:

H; $C_{1-4}$ alkyl, $C_{3-6}$ cycloalkyl, aryl, heterocycle, unsubstituted or substituted with:

a) $C_{1-4}$ alkoxy,
b) halogen, or
c) substituted or unsubstituted aryl or substituted or unsubstituted heterocycle, R⁸ is independently selected from hydrogen, $C_1$–$C_6$ alkyl, 2,2,2-trifluoroethyl, benzyl and aryl;

R⁹ is independently selected from $C_1$–$C_6$ alkyl and aryl;

R¹⁰ is selected from: H; R⁸C(O)—; R⁹S(O)$_m$—; unsubstituted or substituted $C_{1-4}$ alkyl, wherein the substituted alkyl group is substituted with one or two substituents selected from:
    a) $C_{1-4}$ alkoxy,
    b) aryl or heterocycle,
    c) halogen,
    d) HO, e)
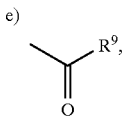

f)
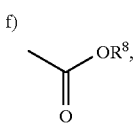

g) —S(O)$_m$R⁹,
    h) N(R⁸)$_2$, and
    i) $C_{3-6}$ cycloalkyl;

R¹¹ is selected from: unsubstituted or substituted aryl, unsubstituted or substituted heterocycle, unsubstituted or substituted pyridinone, wherein the substituents on the cyclic group are selected from: halogen, —OH and —O($C_{1-6}$ alkyl);

A¹ is selected from: a bond, —C(O)—, O, —N(R⁸)—, or S(O)$_m$;

X is a bond, —C(=O)NR¹⁰—, —NR¹⁰C(=O)—, —S(O)$_m$— or —NR¹⁰—;

m is 0, 1 or 2;
n is 0 or 1;
p is 1, 2 or 3; and
q is 0, 1, 2, 3 or 4, provided that q is not 0 when X is —C(=O)NR¹⁰—, —S(O)$_m$— or —NR¹⁰—;
or the pharmaceutically acceptable salts thereof.

The preferred compounds of this invention are as follows:

2—Benzyl-1,2,3,4-tetrahydro-isoquinoline-3(S)-carboxylic acid {2-[3-(4-cyanobenzyl)-3H-imidazol-4-yl]-ethyl}-amide 2-(2-Chlorobenzyl)-1,2,3,4-tetrahydro-isoquinoline-3(S)-carboxylic acid {2-[3-(4-cyanobenzyl)-3H-imidazol-4-yl]-ethyl}-amide 2-(3-Chlorobenzyl)-1,2,3,4-tetrahydro-isoquinoline-3(R)-carboxylic acid {2-[3-(4-cyanobenzyl)-3H-imidazol-4-yl]-ethyl}-amide 2-(3-Chlorobenzyl)-1,2,3,4-tetrahydro-isoquinoline-3(S)-carboxylic acid {2-[3-(4-cyanobenzyl)-3H-imidazol-4-yl]-ethyl}-amide 2-(4-Chlorobenzyl)-1,2,3,4-tetrahydro-isoquinoline-3(S)-carboxylic acid {2-[3-(4-cyanobenzyl)-3H-imidazol-4-yl]-ethyl}-amide 2-(2-Phenylethyl)-1,2,3,4-tetrahydro-isoquinoline-3(S)-carboxylic acid {2-[3-(4-cyanobenzyl)-3H-imidazol-4-yl]-ethyl}-amide 2-(2,2-Diphenylethyl)-1,2,3,4-tetrahydro-isoquinoline-3(S)-carboxylic acid {2-[3-(4-cyanobenzyl)-3H-imidazol-4-yl]-ethyl}-amide 2-(3-Trifluoromethoxybenzyl)-1,2,3,4-tetrahydro-isoquinoline-3(S)-carboxylic acid {2-[3-(4-cyanobenzyl)-3H-imidazol-4-yl]-ethyl}-amide 2-(n-Butyl)-1,2,3,4-tetrahydro-isoquinoline-3(S)-carboxylic acid {2-[3-(4-cyanobenzyl)-3H-imidazol-4-yl]-ethyl}-amide 2-(3-Pyridylmethyl)-1,2,3,4-tetrahydro-isoquinoline-3(S)-carboxylic acid {2-[3-(4-cyanobenzyl)-3H-imidazol-4-yl]-ethyl}-amide 2-(3-Trifluoromethoxybenzyl)-1,2,3,4-tetrahydro-isoquinoline-3(R)-carboxylic acid {2-[3-(4-cyanobenzyl)-3H-imidazol-4-yl]-ethyl}-amide 2-(3-Methoxybenzyl)-1,2,3,4-tetrahydro-isoquinoline-3(R)-carboxylic acid {2-[3-(4-cyanobenzyl)-3H-imidazol-4-yl]-ethyl}-amide 2-(3-Chlorobenzyl)-7-hydroxy-1,2,3,4-tetrahydro-isoquinoline-3(S)-carboxylic acid {2-[3-(4-cyanobenzyl)-3H-imidazol-4-yl]-ethyl}-amide 2-(3-Chlorobenzyl)-1,2,3,4-tetrahydro-isoquinoline-3(S)-carboxylic acid {2-[3-(4-cyanobenzyl)-2-methyl-3H-imidazol-4-yl]-ethyl}-amide 2-(3-Trifluoromethoxybenzyl)-1,2,3,4-tetrahydro-isoquinoline-3(S)-carboxylic acid {2-[3-(4-cyanobenzyl)-2-methyl-3H-imidazol-4-yl]-ethyl}-amide 2-(2,3-Dimethylbenzoyl)-1,2,3,4-tetrahydro-isoquinoline-3(S)-carboxylic acid {2-[3-(4-cyanobenzyl)-3H-imidazol-4-yl]-ethyl}-amide 2-(3-Chlorophenylsulfonyl)-1,2,3,4-tetrahydro-isoquinoline-3(S)-carboxylic acid {2-[3-(4-cyanobenzyl)-3H-imidazol-4-yl]-ethyl}-amide 2-(3-Chlorobenzyl)-7-methoxy-1,2,3,4-tetrahydro-isoquinoline-3(S)-carboxylic acid {2-[3-(4-cyanobenzyl)-3H-imidazol-4-yl]-ethyl}-amide 2-n-Butyl-7-methoxy-1,2,3,4-tetrahydro-isoquinoline-3(S)-carboxylic acid {2-[3-(4-cyanobenzyl)-3H-imidazol-4-yl]-ethyl}-amide 4-{3-[2-(3-chlorobenzyl)-(S)-1,2,3,4-tetrahydro-isoquinolin-3-yl-methyl]-3H-imidazol-4-yl-methyl}-benzonitrile 4-{3-[2-(1-(5-chloro-pyridin-2—one)ethyl)-(S)-1,2,3,4-tetrahydroisoquinolin-3-yl-methyl]-3H-imidazol-4-yl-methyl}-benzonitrile 4-{3-[2-(methylsulfonylethyl)-(S)-1,2,3,4-tetrahydro-isoquinolin-3-yl-methyl]-3H-imidazol-4-yl-methyl}-benzonitrile 4-{3-[2-(3-methoxybenzoyl)-(S)-1,2,3,4-tetrahydro-isoquinolin-3-yl-methyl]-3H-imidazol-4-yl-methyl}-benzonitrile 4-{3-[2-(3-methoxyphenylacetyl)-(S)-1,2,3,4-tetrahydro-isoquinolin-3-yl-methyl]-3H-imidazol-4-yl-methyl}-benzonitrile and 4-{3-[2-(1-(5-chloro-pyridin-2—one)acetyl)-(S)-1,2,3,4-tetrahydroisoquinolin-3-yl-methyl]-3H-imidazol-4-yl-methyl}-benzonitrile 2-[1-(5-Chloro-pyridin-2-one)ethyl]-7-methoxy-1,2,3,4-tetrahydroisoquinoline-3(S)-carboxylic acid {2-[3-(4-cyanobenzyl)-3H-imidazol-4-yl]-ethyl}-amide or an optical isomer or a pharmaceutically acceptable salt thereof.

Specific example compounds of the instant invention are:

2-(3-Chlorobenzyl)-1, 2, 3, 4-tetrahydro-isoquinoline-3(S)-carboxylic acid {2-[3-(4-cyanobenzyl)-3H-imidazol-4-yl]-ethyl]}-amide

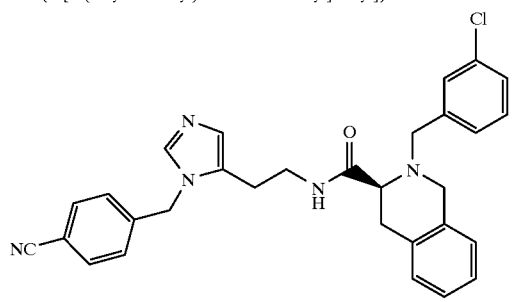

2-(3-Chlorophenylsulfonyl)-1, 2, 3, 4-tetrahydro-isoquinoline-3(S)-carboxylic acid {2-[3-(4-cyanobenzyl)-2-methyl-3H-imidazol-4-yl]-ethyl}-amide

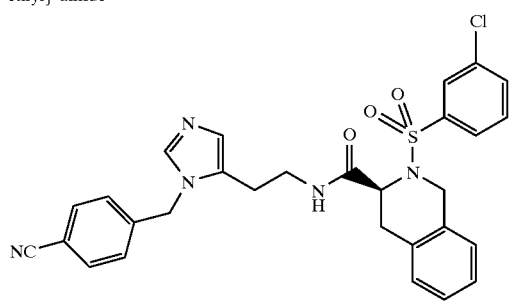

2-(n-Butyl)-1, 2, 3, 4-tetrahydro-isoquinoline-3(S)-carboxylic acid {2-[3-(4-cyanobenzyl)-3H-imidazol-4-yl]-ethyl}-amide

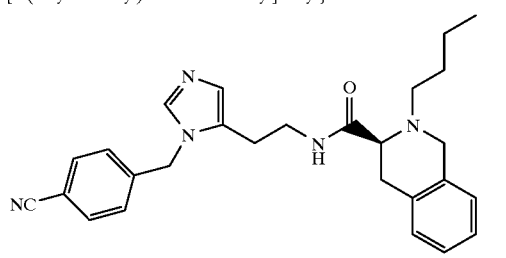

2-(3-Pyridylmethyl)-1, 2, 3, 4-tetrahydro-isoquinoline-3(S)-carboxylic acid {2- [3-(4-cyanobenzyl)-3H-imidazol-4-yl]-ethyl}-amide

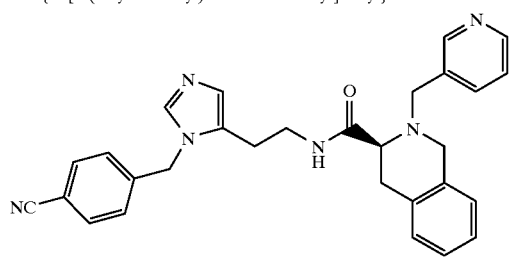

2-(3-Methoxybenzyl)-1, 2, 3, 4-tetrahydro-isoquinoline-3(R)-carboxylic acid {2- [3-(4-cyanobenzyl)-3H-imidazol-4-yl]-ethyl}-amide

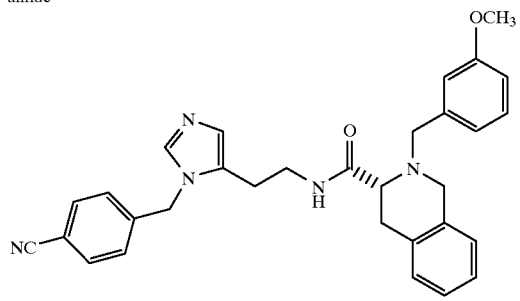

2-(3-Chlorobenzyl)- 7-methoxy-1, 2, 3, 4-tetrahydro-isoquinoline-3(S)-carboxylic acid {2- [3-(4-cyanobenzyl)-3H-imidazol-4-yl]-ethyl}-amide

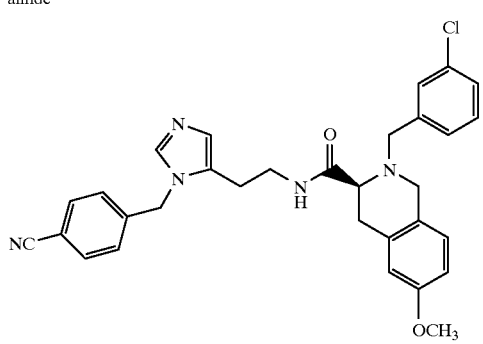

4-{3-[2-(1-(5-chloro-pyridin-2-one)acetyl)-(S)-1, 2, 3, 4-tetrahydro-isoquinolin-3-yl-methyl]-3H-imidazol-4-yl-methyl}-benzonitrile

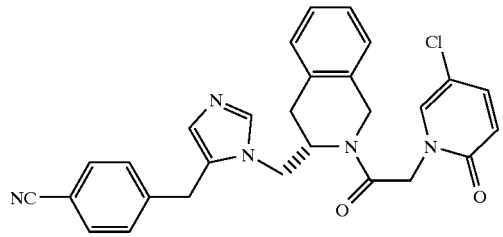

4-{3-[2-(1-(methylsulfonylethyl)-(S)-1, 2, 3, 4-tetrahydro-isoquinolin-3-yl-methyl]-3H-imidazol-4-yl-methyl}-benzonitrile

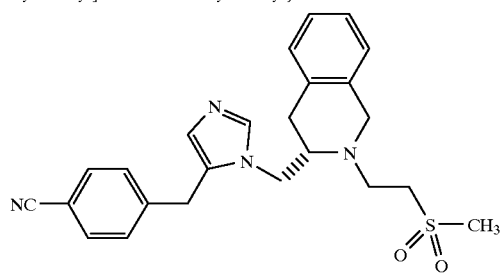

4-{3-[2-(3-methoxybenzoyl)-(S)-1, 2, 3, 4-tetrahydro-isoquinolin-3-yl-methyl]-3H-imidazol-4-yl-methyl}-benzonitrile

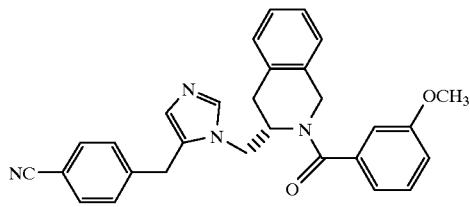

-continued

2-[1-(5-Chloro-pyridin-2-one)ethyl]-7-methoxy-1, 2, 3, 4-tetrahydro-isoquinolin-3(S)-carboxylic acid {2-[3-(4-cyanobenzyl)-3H-imidazol-4-yl]-ethyl}-amide

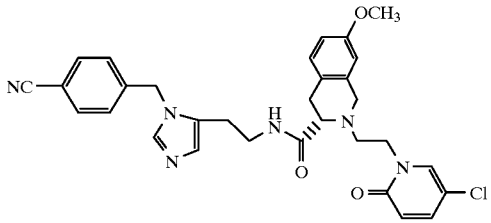

or an optical isomer or a pharmaceutically acceptable salt thereof.

The compounds of the present invention may have asymmetric centers and occur as racemates, racemic mixtures, and as individual diastereomers, with all possible isomers, including optical isomers, being included in the present invention. When any variable (e.g. aryl, heterocycle, $R^{1a}$, $R^4$ etc.) occurs more than one time in any constituent, its definition on each occurence is independent at every other occurence. Also, combinations of substituents/or variables are permissible only if such combinations result in stable compounds.

As used herein, "alkyl" is intended to include both branched and straight-chain saturated aliphatic hydrocarbon groups having the specified number of carbon atoms; "alkoxy" represents an alkyl group of indicated number of carbon atoms attached through an oxygen bridge. "Halogen" or "halo" as used herein means fluoro, chloro, bromo and iodo.

As used herein, "aryl" is intended to mean any stable monocyclic, bicyclic or tricyclic carbon ring of up to 7 members in each ring, wherein at least one ring is aromatic. Examples of monocyclic and bicyclic aryl elements include phenyl, naphthyl, tetrahydronaphthyl, indanyl, biphenyl, phenanthryl, anthryl or acenaphthyl. Examples of tricyclic aryl elements include 10,11 -dihydro-5H-dibenzo[a,d]cyclohepten-5-yl (which is also known as dibenzylsuberyl), 9-fluorenyl and 9,10-dihydroanthracen-9-yl. Preferably, "aryl" is a monocyclic or bicyclic carbon ring.

The term heterocycle or heterocyclic, as used herein, represents a stable 5- to 7-membered monocyclic or stable 8- to 11-membered bicyclic heterocyclic ring or stable 13- to 15-membered tricyclic heterocyclic ring, which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. Examples of monocyclic and bicyclic heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, 2-oxopyrrolidinyl, piperidyl, piperazinyl, pyridyl, pyrazinyl, pyrazolidinyl, pyrazolyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, and thienyl. Examples of tricyclic heterocyclic elements include, but are not limited to, 6,11-dihydro-5H-benzo[5,6]cyclohepta[1,2-b]pyridine, 9,10-dihydro-4H-3-thia-benzo[f]azulen-4-yl and 9-xanthenyl. The 6,11-dihydro-5H-benzo[5,6]cyclohepta[1,2-b]pyridine moiety has the following structure:

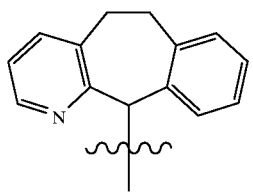

Preferably, "heterocyclic" is a monocyclic or bicyclic moiety.

As used herein, "heteroaryl" is intended to mean any stable monocyclic, bicyclic or tricyclic carbon ring of up to 7 members in each ring, wherein at least one ring is aromatic and wherein from one to four carbon atoms are replaced by heteroatoms selected from the group consisting of N, O, and S. Examples of monocyclic and bicyclic heteroaryl elements include, but are not limited to, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolyl, indolinyl, indolyl, isochromanyl, isoindolinyl, isoquinolinyl, isothiazolyl, naphthyridinyl, oxadiazolyl, pyridyl, pyrazinyl, pyrazolyl, pyridazinyl, pyrimidinyl, pyrrolyl, quinazolinyl, quinolinyl, quinoxalinyl, tetrahydroisoquinolinyl, tetrahydroquinolinyl, thiazolyl, thienofuryl, thienothienyl, and thienyl. Examples of tricyclic heteroaryl elements include, but are not limited to, 6,11-dihydro-5H-benzo[5,6]cyclohepta[1,2-b]pyridine. Preferably, "heteroaryl" is a monocyclic or bicyclic moiety.

As used herein, the terms "substituted aryl", "substituted heterocycle", "substituted pyridinone" and "substituted cycloalkyl" are intended to include the cyclic group containing from 1 to 3 substitutents in addition to the point of attachment to the rest of the compound. Such substitutents are preferably selected from the group which includes but is not limited to F, Cl, Br, $CF_3$, $NH_2$, $N(C_1-C_6$ alkyl$)_2$, $NO_2$, CN, $(C_1-C_6$ alkyl$)O$—, —OH, $(C_1-C_6$ alkyl$)S(O)_m$—, $(C_1-C_6$ alkyl$)C(O)NH$—, $H_2N$—C(NH)—, $(C_1-C_6$ alkyl$)C(O)$—, $(C_1-C_6$ alkyl$)OC(O)$—, $N_3$,$(C_1-C_6$ alkyl$)OC(O)NH$— and $C_1-C_{20}$ alkyl.

When $R^6$ and $R^7$ or $R^7$ and $R^{7a}$ are combined to form a ring, cyclic amine moieties are formed. Examples of such cyclic moieties include, but are not limited to:

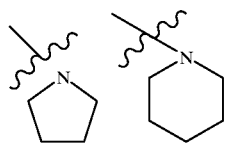

In addition, such cyclic moieties may optionally include another heteroatom(s). Examples of such heteroatom-containing cyclic amine moieties include, but are not limited to:

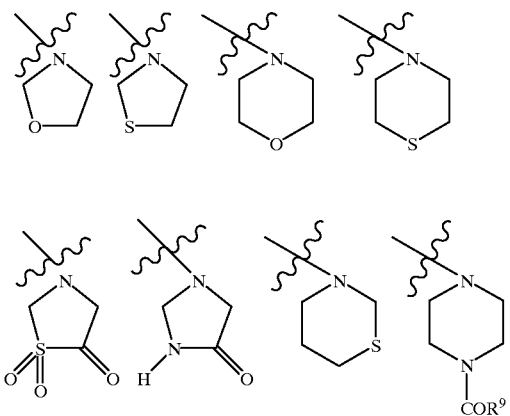

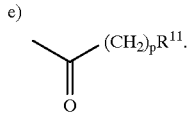

-continued e)
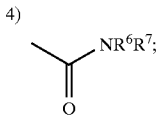
$(CH_2)_p R^{11}$.

Lines drawn into the ring systems from substituents (such as from $R^2$, $R^3$, $R^4$ etc.) indicate that the indicated bond may be attached to any of the substitutable ring carbon atoms.

Preferably, $R^{1a}$ and $R^{1b}$ are independently selected from: hydrogen, —$N(R^8)_2$, $R^8C(O)NR^8$— or $C_1$–$C_6$ alkyl which is unsubstituted or substituted by —$N(R^8)_2$, $R^8O$— or $R^8C(O)NR^8$—.

Preferably, $R^2$ is selected from:

a) $C_{1-8}$ alkyl, unsubstituted or substituted with one or more of:
  1) aryl or heterocycle, unsubstituted or substituted with:
    i) $C_{1-4}$ alkyl,
    ii) $(CH_2)_p OR^6$,
    iii) $(CH_2)_p NR^6R^7$,
    iv) halogen,
    v) $C_{1-4}$ perfluoroalkyl,
  2) $OR^6$,
  3) $SR^6$, $SO_2R^6$, or 4)
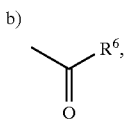
$NR^6R^7$;

b)
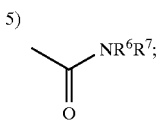
$R^6$, c) aryl, unsubstituted or substituted with one or more of:
  1) $C_{1-8}$ alkyl,
  2) $C_{1-8}$ perfluoroalkyl,
  3) $OR^6$,
  4) $SR^6$, $SO_2R^6$, or 5)
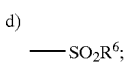
$NR^6R^7$;

d)
—$SO_2R^6$;

Preferably, $R^2$ comprises at least one unsubstituted or substituted phenyl.

Preferably, $R^{3a}$ and $R^{3b}$ are independently selected from: hydrogen, $C_1$–$C_6$ perfluoroalkyl, F, Cl, Br, $R^8O$—, $R^9S(O)_m$—, CN, $R^8C(O)$—, —$N(R^8)_2$ and $C_1$–$C_6$ alkyl.

Preferably, $R^4$ is selected from: hydrogen, $C_1$–$C_6$ perfluoroalkyl, F, Cl, Br, $R^8O$—, $R^9S(O)_m$—, CN, $NO_2$, $R^8_2N$—$C(NR^8)$—, $R^8C(O)$—, $N_3$, —$N(R^8)_2$, $R^9OC(O)NR^8$— and $C_1$–$C_6$ alkyl.

Preferably, $R^5$ is hydrogen.

Preferably, $R^{7b}$ is $C_1$–$C_6$ alkyl substituted with hydrogen or an unsubstituted or substituted aryl group.

Preferably, $R^8$ is selected from H, $C_1$–$C_6$ alkyl and benzyl.

Preferably, $A^1$ and $A^2$ are independently selected from: a bond, —$C(O)NR^8$—, —$NR^8C(O)$—, O, —$N(R^8)$—, —$S(O)_2N(R^8)$— and —$N(R^8)S(O)_2$—.

Preferably, V is selected from hydrogen, heterocycle and aryl.

Preferably, W is imidazolyl.

Preferably, X is a bond, —$C(=O)NR^{10}$—, —$NR^{10}C(=O)$— or —$NR^{10}$—.

Preferably, n, p and r are independently 0, 1, or 2. More preferably, r is 1.

Preferably t is 1.

The pharmaceutically acceptable salts of the compounds of this invention include the conventional non-toxic salts of the compounds of this invention as formed, e.g., from non-toxic inorganic or organic acids. For example, such conventional non-toxic salts include those derived from inorganic acids such as hydrochloric, hydrobromic, sulfuric, sulfamic, phosphoric, nitric and the like: and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like.

It is intended that the definition of any substituent or variable (e.g., $R^{1a}$, Z, n, etc.) at a particular location in a molecule be independent of its definitions elsewhere in that molecule. Thus, —$N(R8)_2$ represents —$NH_2$, —$NHCH_3$, —$NHC_2H_5$, etc. It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials.

The pharmaceutically acceptable salts of the compounds of this invention can be synthesized from the compounds of this invention which contain a basic moiety by conventional chemical methods. Generally, the salts are prepared either by ion exchange chromatography or by reacting the free base with stoichiometric amounts or with an excess of the desired salt-forming inorganic or organic acid in a suitable solvent or various combinations of solvents.

Abbreviations used in the description of the chemistry and in the Examples that follow are:

| | |
|---|---|
| Ac₂O | Acetic anhydride; |
| Boc | t-Butoxycarbonyl; |
| CBz | Carbobenzyloxy; |
| DBU | 1,8-diazabicyclo[5.4.0]undec-7-ene; |
| DMAP | 4-Dimethylaminopyridine; |
| DME | 1,2-Dimethoxyethane; |
| DMF | Dimethylformamide; |
| EDC | 1-(3-dimethylaminopropyl)-3-ethyl-carbodiimide-hydrochloride; |
| Et₃N | Triethylamine; |
| EtOAc | Ethyl acetate; |
| FAB | Fast atom bombardment; |
| HOBT | 1-Hydroxybenzotriazole hydrate; |
| HOOBT | 3-Hydroxy-1,2,2-benzotriazin-4(3H)-one; |
| HPLC | High-performance liquid chromatography; |
| MCPBA | m-Chloroperoxybenzoic acid; |
| MsCl | Methanesulfonyl chloride; |
| NaHMDS | Sodium bis(trimethylsilyl)amide; |
| Py | Pyridine; |
| TFA | Trifluoroacetic acid; |
| THF | Tetrahydrofuran. |

The compounds of this invention are prepared by employing reactions as shown in the Schemes 1–20, in addition to other standard manipulations such as ester hydrolysis, cleavage of protecting groups, etc., as may be known in the literature or exemplified in the experimental procedures. While stereochemistry is shown in the Schemes, a person of ordinary skill in the art would understand that the illustrated compounds represent racemic mixtures or specific enantiomers depending on the starting materials employed.

These reactions may be employed in a linear sequence to provide the compounds of the invention or they may be used to synthesize fragments which are subsequently joined by the reductive alkylation or acylation reactions described in the Schemes.

Synopsis of Schemes 1–6:

The requisite intermediates are in some cases commercially available, or can be prepared according to literature procedures, for the most part. In Schemes 1–2, for example, the syntheses of racemic 2,3-disubstituted 1,2,3,4-tetrahydroisoquinolines are outlined. It is well understood by one of ordinary skill in the art that such chemical manipulations can also be applied to enantiomerically pure isomers (ie. the (S) isomer or the (R) isomer).

The protected 3-carboxylic acid 1,2,3,4-tetrahydroisoquinoline 1 can be treated with an appropriately substituted amine in the presence of a suitable coupling reagent, such as EDC/HOBT, and the like, to provide the amide 2. The intermediate 2 is then deprotected and the ring nitrogen can then be reductively alkylated to provide the instant compound 3.

As shown in Scheme 2, the protected 3-carboxylic acid 1,2,3,4-tetrahydroisoquinoline 1 can be reduced and the alcohol converted to the azide by Mitsunobu chemistry. The aminomethyltetrahydroisoquinoline 4 is obtained after LAH reduction. Subsequent amide formation provides intermediate 5, which is then subjected to the reactions illustrated in Scheme 1 to provide compound 6 of the instant invention.

Schemes 3–5 illustrate the syntheses of 2,3-disubstituted 1,2,3,4-tetrahydroisoquinolines of the instant invention wherein the "X" moiety is other than an amido moiety.

Scheme 3 illustrates the syntheses of compounds of the instant invention wherein "X" is —S— or —SO₂—. Commerically available chiral 1,2,3,4-tetrahydroisoquinoline 7 can be esterified and is then reductively alkylated to provide the ester 8. Intermediate 8 is reduced to the alcohol 9, activated and treated with a suitable thioacetate to provide the thioester 10. The thiol is then generated and may be alkylated and optionally oxidized to provide compounds 11 and 12 of the instant invention.

The intermediate 9 may be selectively oxidized back to an aldehyde, which can then be utilized to reductively alkylate a suitably substituted amine to provide the instant compound 13. The secondary amine of 13 can be further functionalized as illustrated in Scheme 4.

The intermediate alcohol from Scheme 2 can be deprotected then either reductively alkylated, alkylated, or alkylated under Michael conditions to provide intermediate 9. The activated alcohol can also be reacted with a suitably substituted imidazolyl to provide compounds of the instant invention wherein "X" is a bond, as shown in Scheme 5.

Scheme 6 illustrates the syntheses of compounds of the instant invention wherein $R^2$ is an aryl moiety.

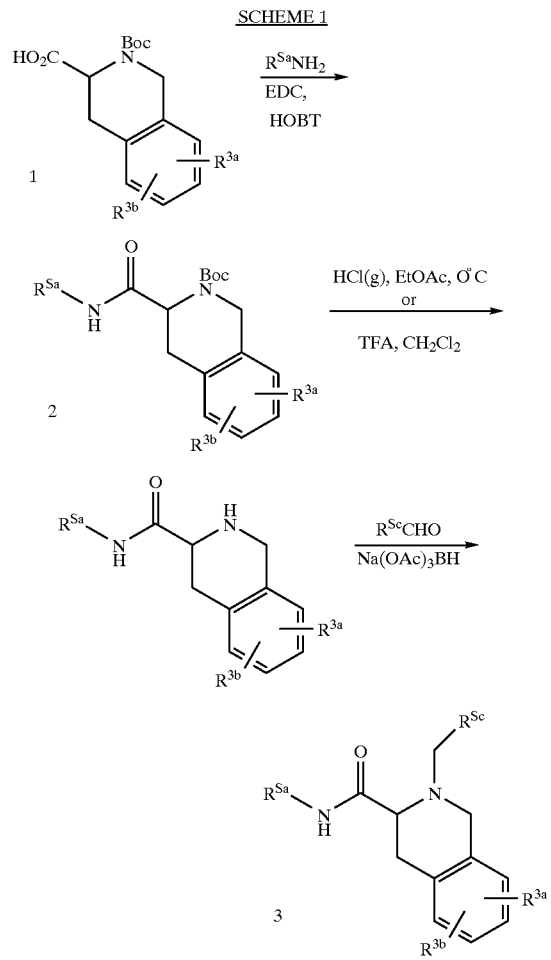

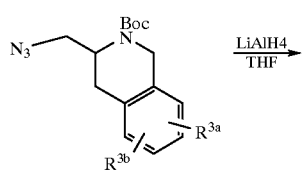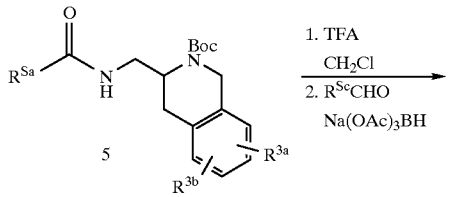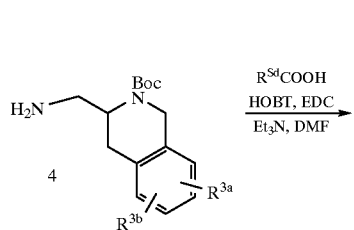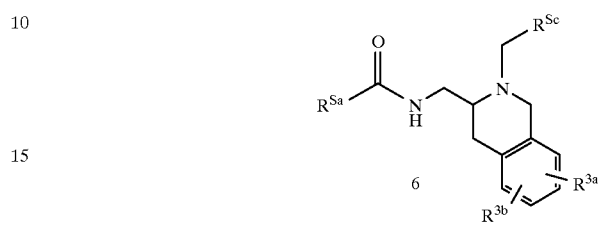
SCHEME 3
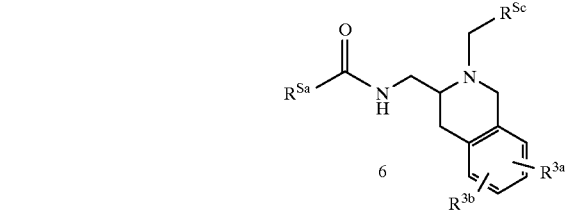

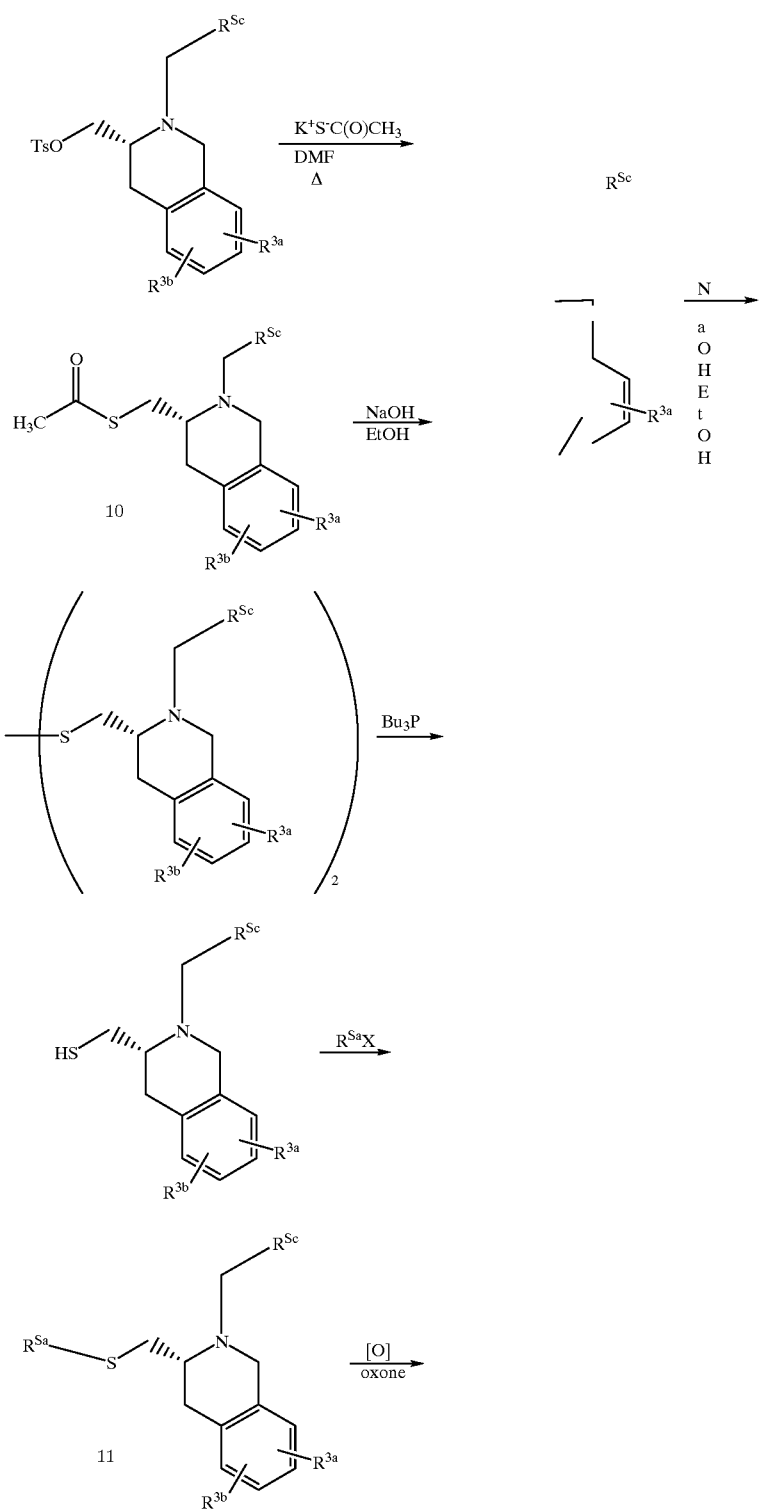

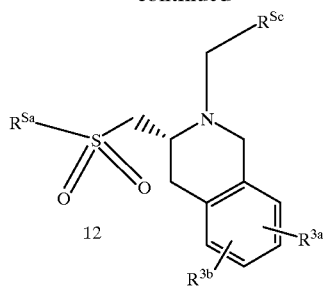
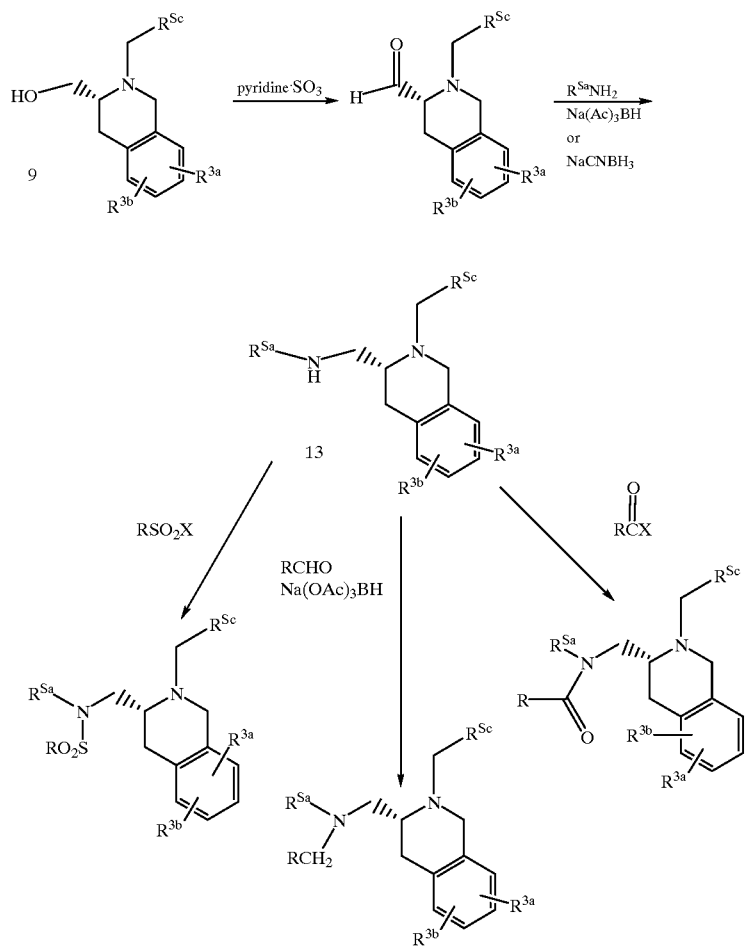
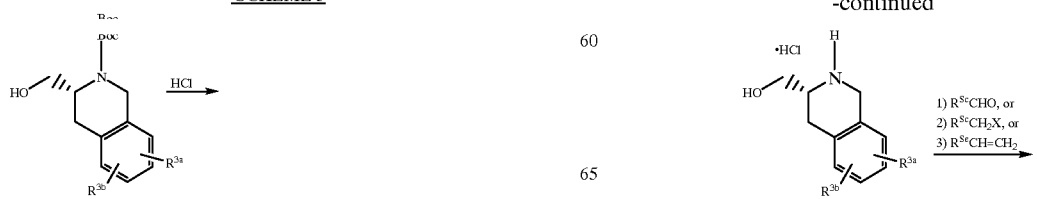

-continued

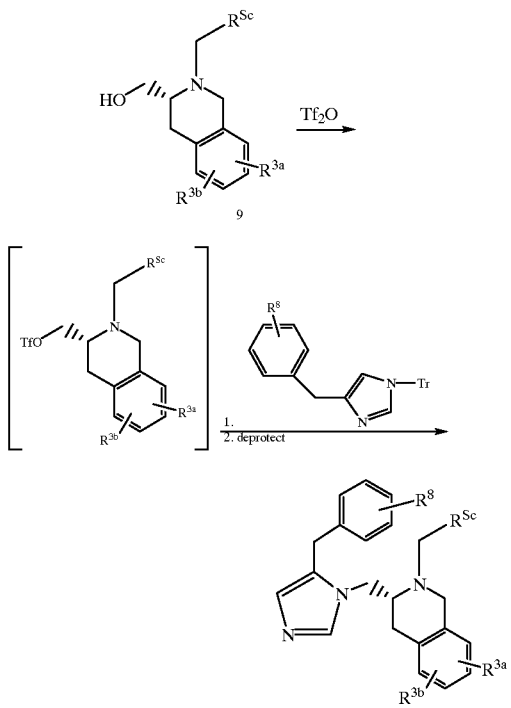

SCHEME 6

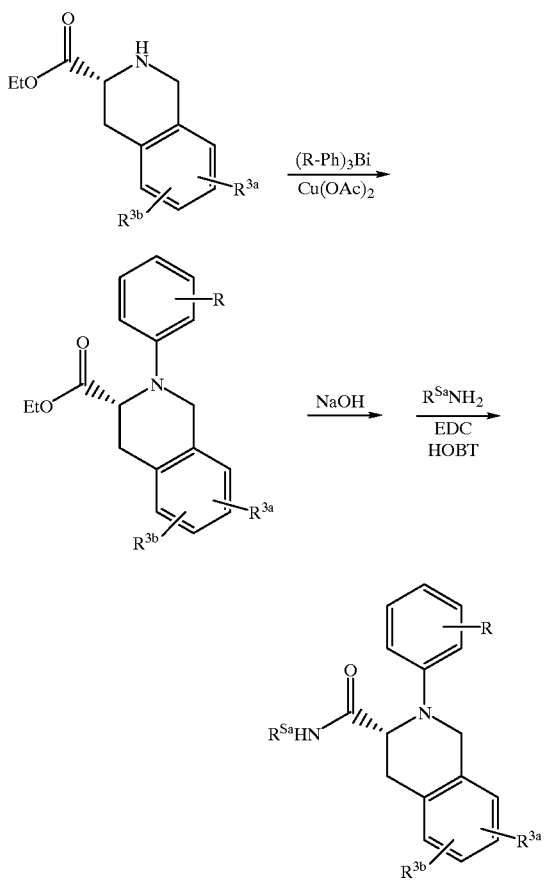

In the above Schemes it is understood that $R^{Sa}$ and $R^{Sd}$ are

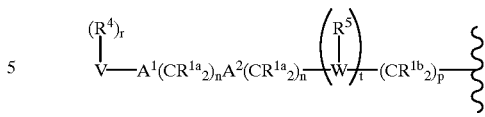

or a protected precursor thereof;
$R^{Sc}CH_2$— is $R^2$ or a protected precursor thereof; and
$R^{Se}CH_2CH_2$— is $R^2$ or a protected precursor thereof: and
$R^{Sb}$— is $R^6$ or a protected precursor thereof; and
R— is a "substituent" or a protected precusor thereof.

It is understood that a variety of amines and acids, either commercially available or readily synthesized by reactions well known in the art, which contain the side-chain moieties $R^{Sa}$ and $R^{Sd}$(C=O) may be utilized in the reactions described hereinabove. Schemes 7–20 illustrate specific reactions wherein such intermediates containing the side-chain moieties $R^{Sa}$ and $R^{Sd}$(C=O) may be prepared. It is understood that while Schemes 7–20 illustrate preparation of both unprotected and unprotected intermediates, a person of ordinary skill would appreciate that subsequent reactions which utilize those intermediates, such as those described in Schemes 1–6, may require protection and eventual deprotection of certain intermediate moieties.

The selectively protected intermediate 14 utilized in the synthesis illustrated in Scheme 7 can be reductively alkylated with a variety of aldehydes, such as 15. The aldehydes can be prepared by standard procedures, such as that described by O. P. Goel, U. Krolls, M. Stier and S. Kesten in *Organic Syntheses*, 1988, 67, 69–75. The reductive alkylation can be accomplished at pH 5–7 with a variety of reducing agents, such as sodium triacetoxyborohydride or sodium cyanoborohydride in a solvent such as dichloroethane, methanol or dimethylformamide. The ester product 16 can be deprotected with trifluoroacetic acid in methylene chloride to give the substituted diamine 17. That diamine is isolated in the salt form, for example, as a trifluoroacetate, hydrochloride or acetate salt, among others. The product diamine 17 can be further selectively protected and reductively alkylated with a second aldehyde to obtain an analogous tertiary amine. Alternatively, the diamine 17 can be cyclized to obtain intermediates such as the dihydroimidazole 18 by procedures known in the literature. The ester 18 can then be utilized in a reaction such as illustrated in Scheme 3 hereinabove or can be converted to the amine 20, via the azido intermediate 19. That amine can then be utilized in reactions such as illustrated in Scheme 1.

Scheme 8 illustrates preparation of aralkyl imidazolyl intermediates 25 that can be utilized in reactions such as illustrated in Scheme 2. Thus imidazole acetic acid 21 can be converted to the protected acetate 23 by standard procedures, and 23 can be first reacted with an alkyl halide, then treated with refluxing methanol to provide the regiospecifically alkylated imidazole acetic acid ester 24. Hydrolysis provides the acetic acid 25.

Alternatively, intermediate 25 can be converted into the homologous amine 28 via the azido intermediate 27, as shown in Scheme 9. This amine can then be utilized in reactions such as illustrated in Scheme 1.

Preparation of amine intermediates having mixed heteroatom substitution is illustrated in Schemes 10 and 11. Thus the protected serine 29 can be reduced to the alcohol 30, which can then undergo a Mitsunobu reaction to provide the phthalimidyl intermediate 31. Deprotection and selective reprotection give the alcohol 33, which can be oxidized to the aldehyde 34. The aldehyde 34 can be subsequently alkylated and finally deprotected to provide the amine intermediate 35.

The Boc protected phthalimidyl alcohol 33 can also be utilized to synthesize 2-aziridinylmethylamines such as 36 (Scheme 11). Treating 33 with 1,1'-sulfonyldiimidazole and sodium hydride in a solvent such as dimethylformamide led to the formation of aziridine 36. The aziridine may then be reacted in the presence of a nucleophile, such as a thiol, in the presence of base to yield, after deprotection, the ring-opened intermediate amine 37.

In addition, amines such as 42 derived from amino acids such as O-alkylated tyrosines can be prepared according to standard procedures as shown in Scheme 12. Illustrated is a procedure where the amine moiety is derived from the azide of an intermediate such as 41.

Schemes 13–16 illustrate syntheses of suitably substituted alkanols useful in the syntheses of the instant compounds wherein the variable W is present as a pyridyl moiety. The hydroxyl moiety of such intermediates may be converted into the corresponding amine, as illustrated in Scheme 13 or may be converted to a suitable leaving group, as illustrated in Scheme 15. Similar synthetic strategies for preparing alkanols that incorporate other heterocyclic moieties for variable W are also well known in the art.

Compounds of the instant invention wherein the $A^1(CR^{1a}2)_nA^2(CR^{1a}2)_n$ linker is a substituted methylene may be synthesized by the methods shown in Scheme 19. Thus, the N-protected imidazolyl iodide 43 is reacted, under Grignard conditions with a suitably protected benzaldehyde to provide the alcohol 44. Acylation, followed by the alkylation procedure illustrated in the Schemes above (in particular, Scheme 5) provides the instant compound 45. If other $R^1$ substituents are desired, the acetyl moiety can be manipulated as illustrated in the Scheme.

Scheme 18 illustrates synthesis of an instant compound wherein a non-hydrogen $R^{5b}$ is incorporated in the instant compound. Thus, a readily available 4-substituted imidazole 46 may be selectively iodinated to provide the 5-iodoimidazole 47. That imidazole may then be protected and coupled to a suitably substituted benzyl moiety to provide intermediate 48. Intermediate 48 can then undergo the alkylation reactions that were described hereinabove.

Compounds of the instant invention wherein the $A^1(CR^1_2)_nA^2(CR^1_2)_n$ linker is oxygen may be synthesized by methods known in the art, for example as shown in Scheme 19. The suitably substituted phenol 49 may be reacted with methyl N-(cyano)methanimidate to provide the 4-phenoxyimidazole 50. After selective protection of one of the imidazolyl nitrogens, the intermediate 51 can undergo alkylation reactions as described for the benzylimidazoles hereinabove.

Scheme 20 illustrates an alternative route to prepare compounds of the instant invention wherein "X" is a bond and $R^2$ is $R^{5c}C(O)$.

SCHEME 7

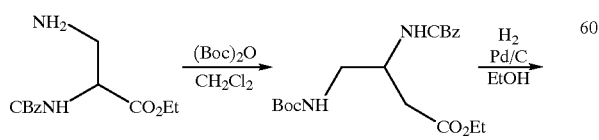

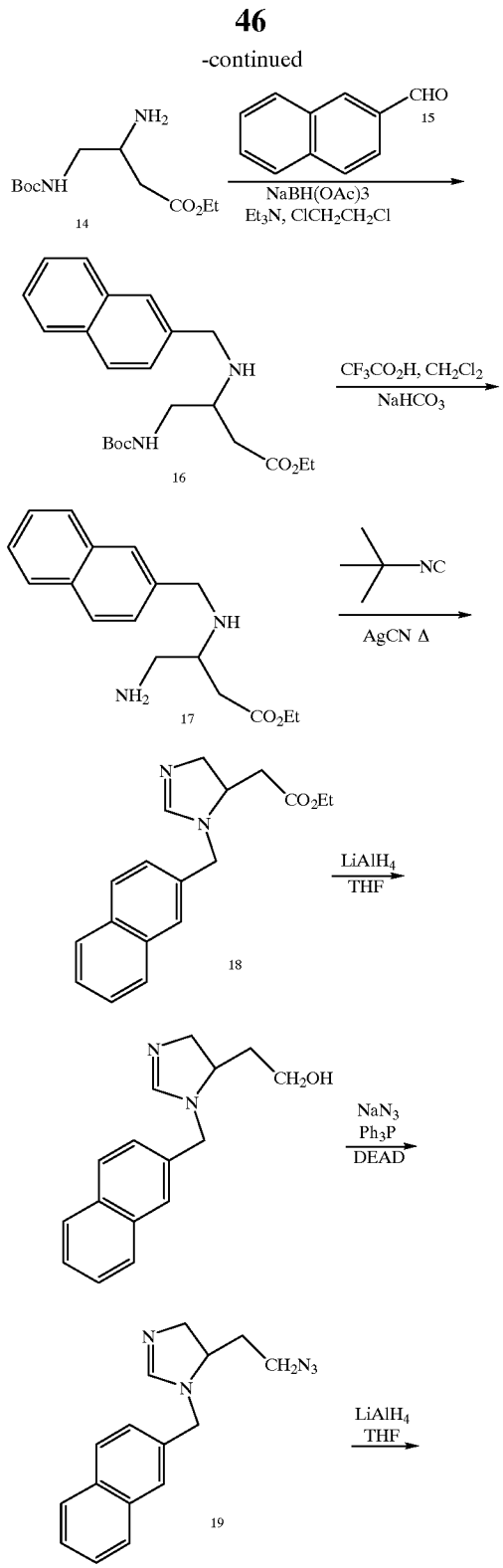

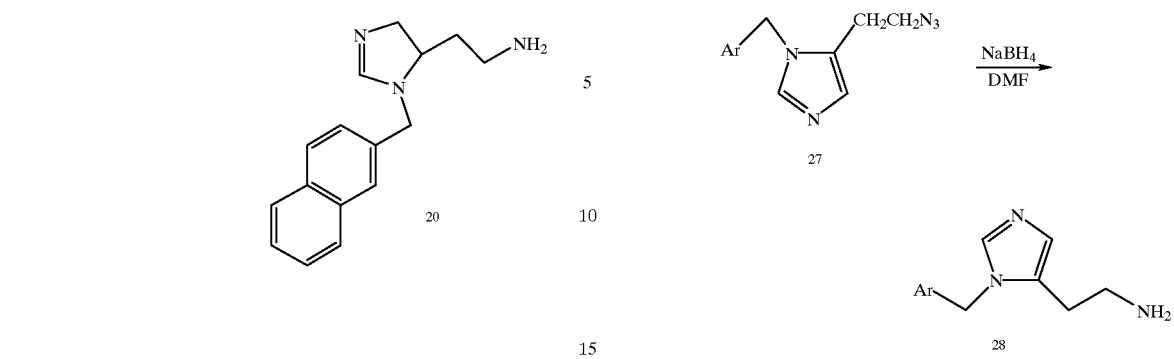
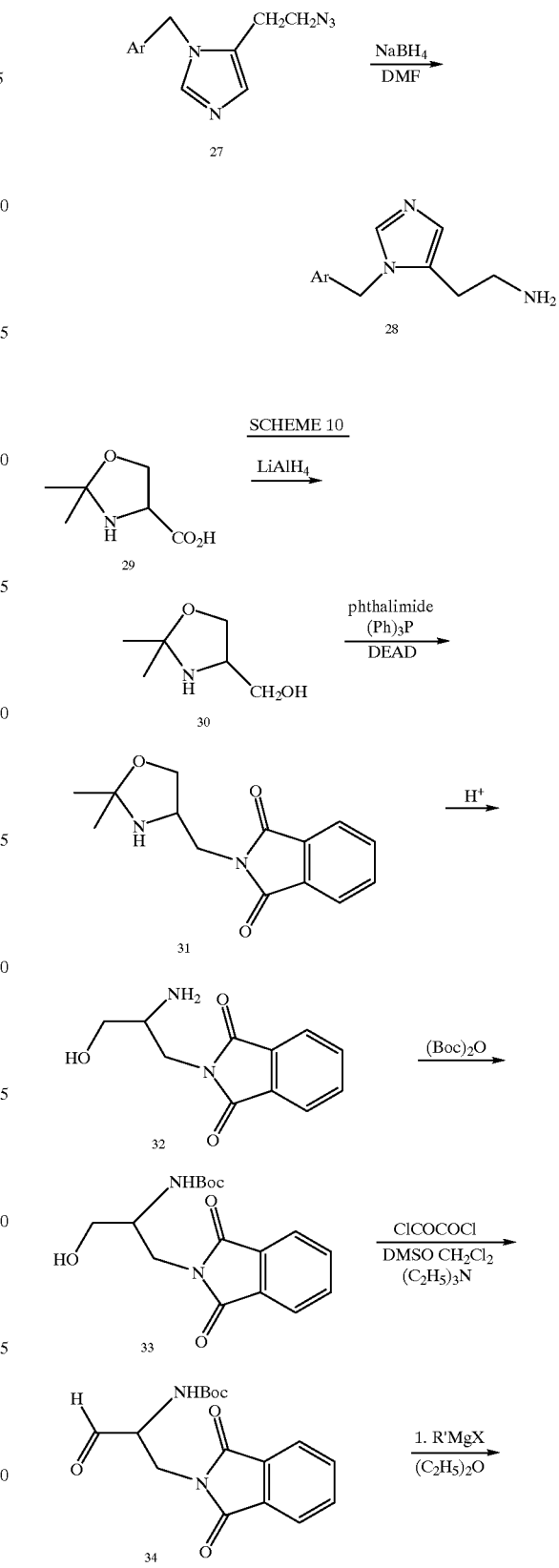

49

-continued

[Structure: R'-CH(OH)-CH(NHBoc)-CH2-N(phthalimide)] →(H2N-NH2 / EtOH)→ [Structure 35: R'-CH(OH)-CH(NHBoc)-CH2-NH2]

wherein R' is $R^{1a}$ or a protected precursor thereof

SCHEME 11

[Structure 33: HO-CH2-CH(NHBoc)-CH2-N(phthalimide)] →(1,1'-sulfonyldiimidazole, NaH, DMF 0°C)→ [Structure 36: aziridine-CH2-N(phthalimide)] →(R'SH, (C2H5)3N, CH3OH, Δ)→ [Structure: R'S-CH2-CH(NH2)-CH2-N(phthalimide)] →(1. Boc2O, 2. H2N-NH2)→ [Structure 37: R'S-CH2-CH(NHBoc)-CH2-NH2]

wherein R' is $(R^4)_r$—V— or a protected precursor thereof

SCHEME 12

[Structure 38: 2-HO-C6H4-CH2-CH(NH2)-CO2H] →(1) Boc2O, K2CO3, THF-H2O; 2) CH2N2, EtOAc)→

50

-continued

[Structure: 2-HO-C6H4-CH2-CH(NHBoc)-CO2CH3] →(LiAlH4, THF, 0–20°C)→ [Structure 39: 2-HO-C6H4-CH2-CH(NHBoc)-CH2OH] →(R'CH2X, Cs2CO3, DMF)→ [Structure 40: 2-R'CH2O-C6H4-CH2-CH(NHBoc)-CH2OH] →(NaN3, (Ph)3P, DEAD)→ [Structure 41: 2-R'CH2O-C6H4-CH2-CH(NHBoc)-CH2N3] →(H2, Pd/C, CH3OH)→ [Structure 42: 2-R'CH2O-C6H4-CH2-CH(NHBoc)-CH2NH2]

wherein R'CH2— is $R^8$ or a protected precursor thereof

SCHEME 13

[Structure: 2-amino-5-methylpyridine] →(1) HNO2, Br2; 2) KMnO4; 3) MeOH, H+)→ [Structure: 2-bromo-5-methoxycarbonylpyridine] →(R4-C6H4-CH2-MgCl, ZnCl2, NiCl2(Ph3P)2)→ [Structure: 2-(R4-benzyl)-5-methoxycarbonylpyridine] →(NaBH4 (excess))→

-continued
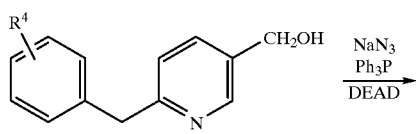
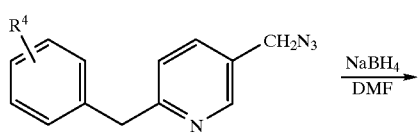
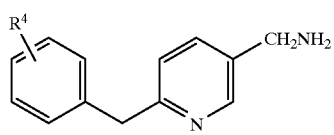
SCHEME 14
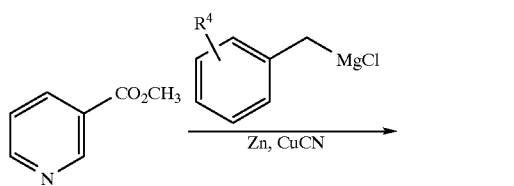
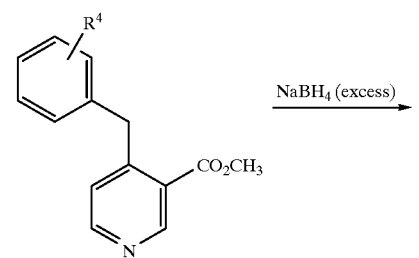
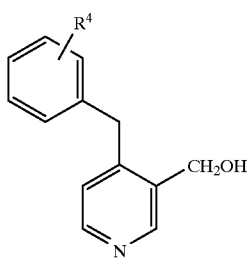
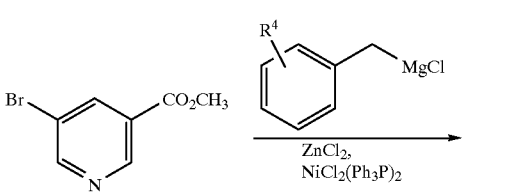
-continued
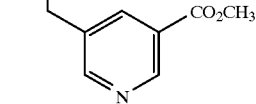
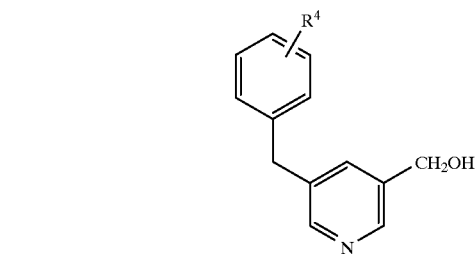
SCHEME 15
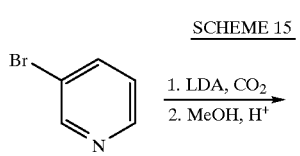
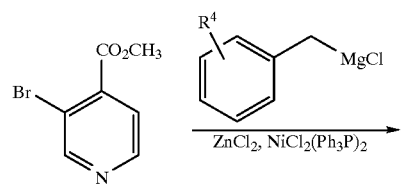
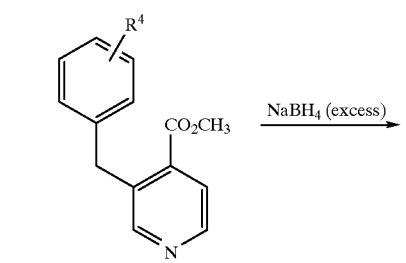
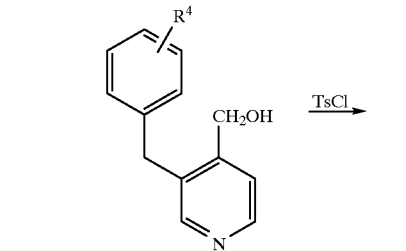

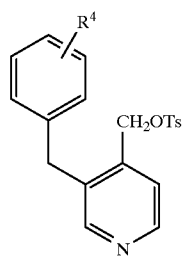
SCHEME 16
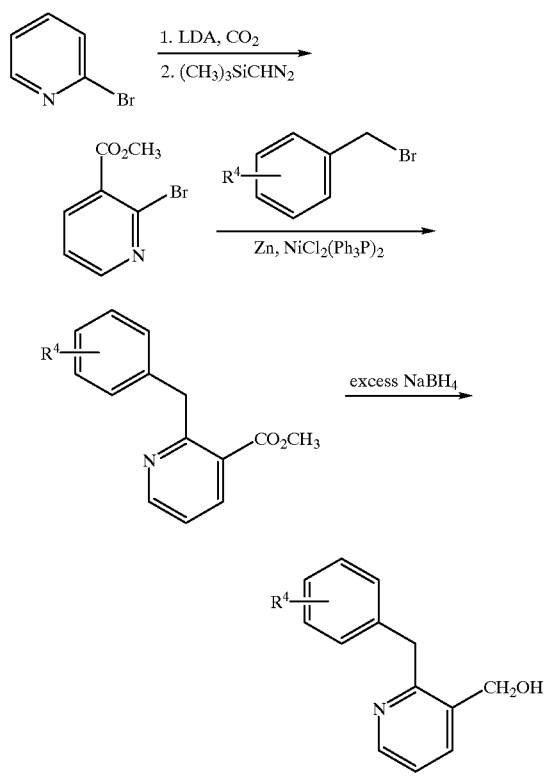
SCHEME 17
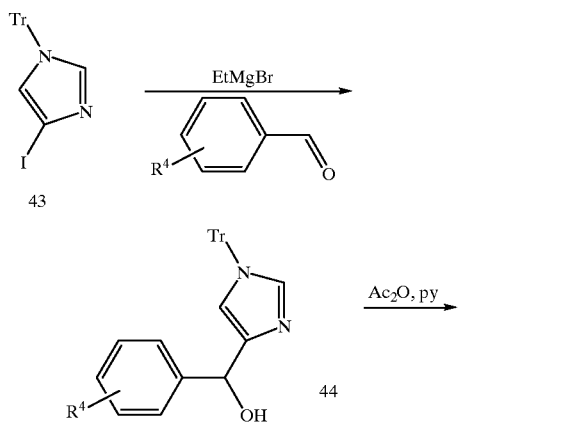
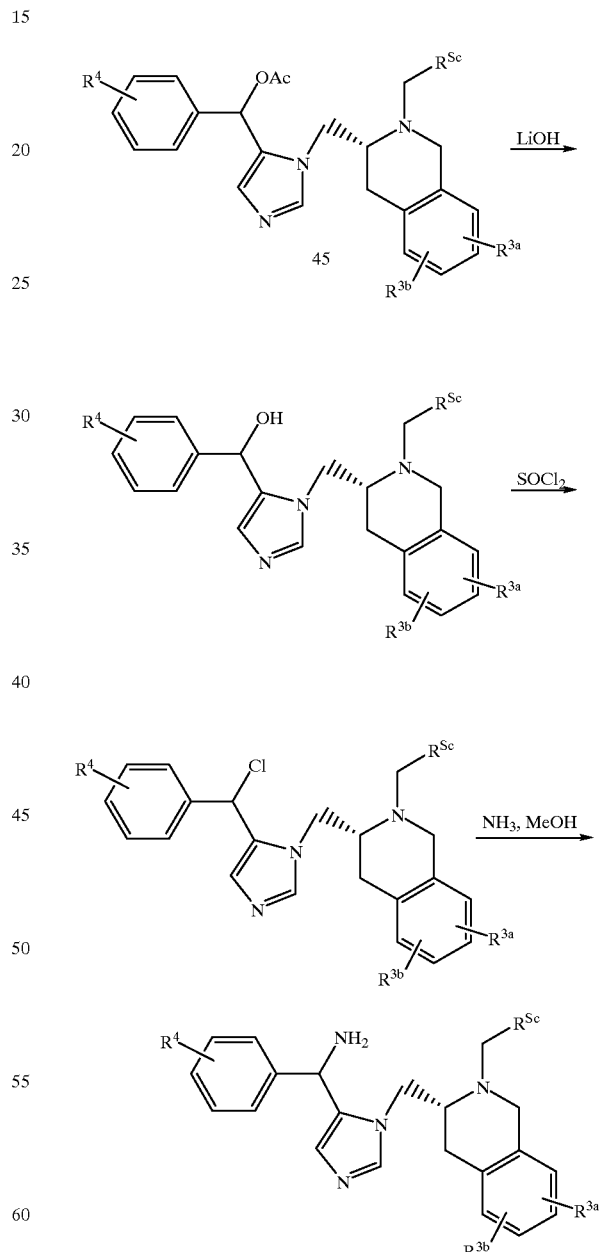

-continued
+
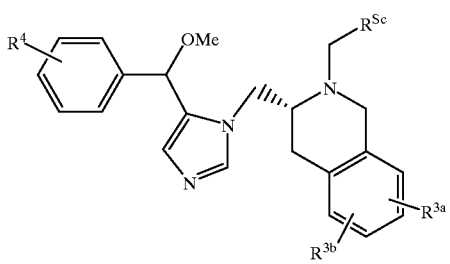
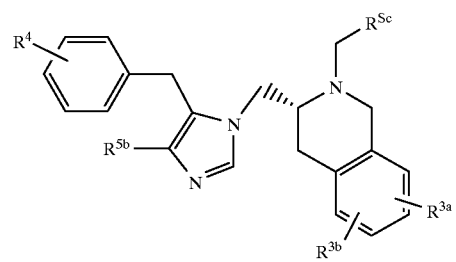
SCHEME 18
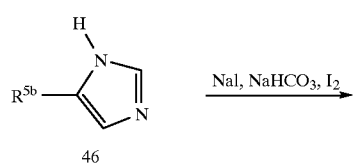
46
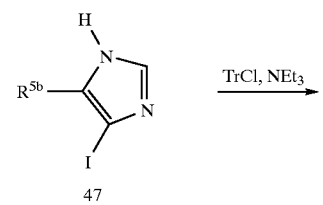
47
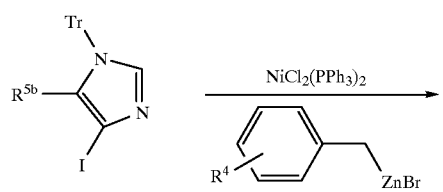
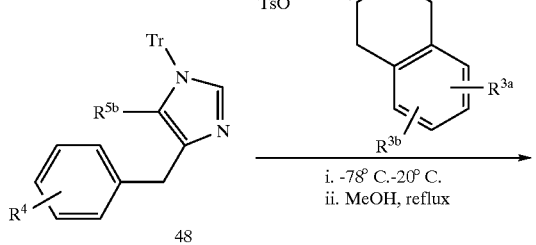
48
SCHEME 19
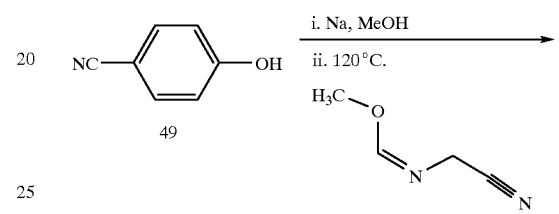
49
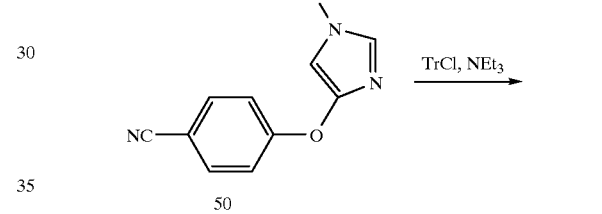
50
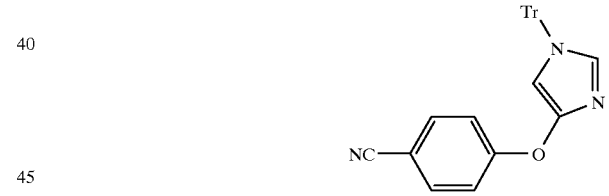
51
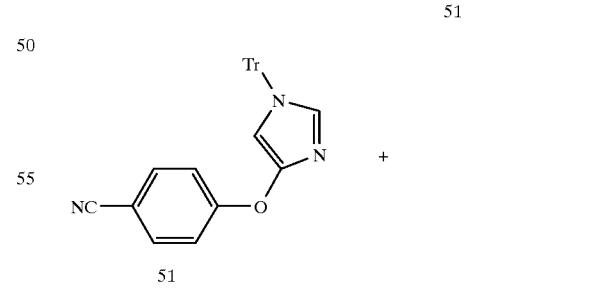
51

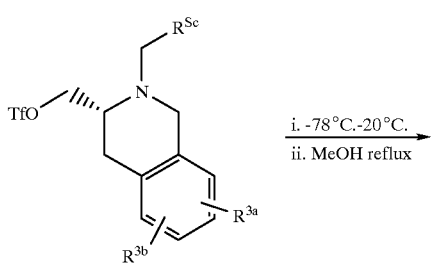

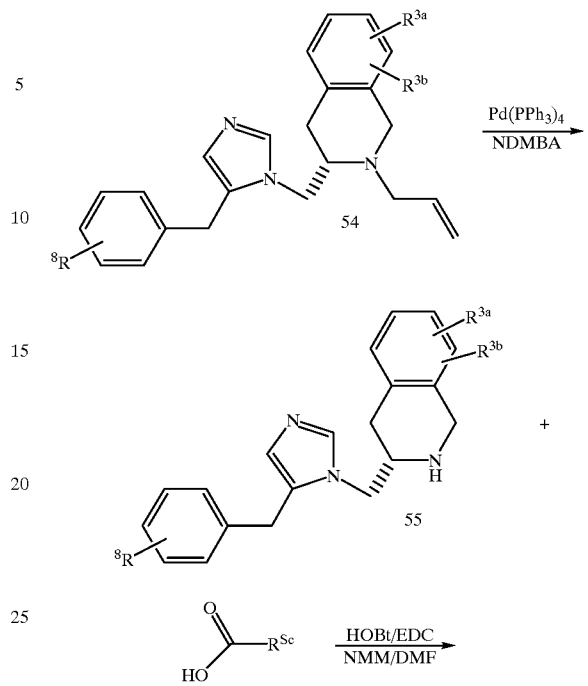

SCHEME 20

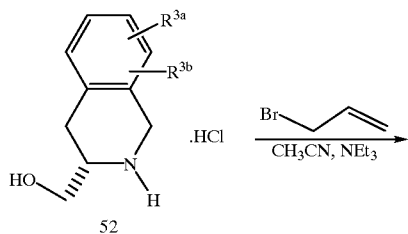

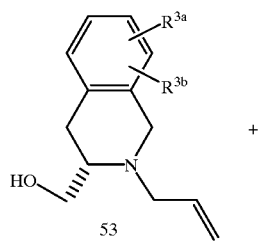

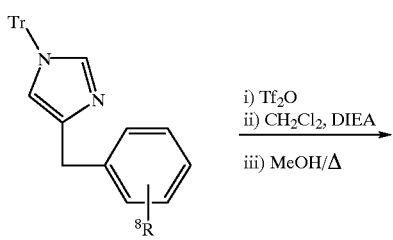

The instant compounds are useful as pharmaceutical agents for mammals, especially for humans. These compounds may be administered to patients for use in the treatment of cancer. Examples of the type of cancer which may be treated with the compounds of this invention include, but are not limited to, colorectal carcinoma, exocrine pancreatic carcinoma, myeloid leukemias and neurological tumors. Such tumors may arise by mutations in the ras genes themselves, mutations in the proteins that can regulate Ras activity (i.e., neurofibromin (NF-1), neu, scr, abl, lck, fyn) or by other mechanisms.

The compounds of the instant invention inhibit farnesyl-protein transferase and the farnesylation of the oncogene protein Ras. The instant compounds may also inhibit tumor angiogenesis, thereby affecting the growth of tumors (J. Rak et al. *Cancer Research,* 55:4575–4580 (1995)). Such anti-angiogenesis properties of the instant compounds may also be useful in the treatment of certain forms of blindness related to retinal vascularization.

The compounds of this invention are also useful for inhibiting other proliferative diseases, both benign and malignant, wherein Ras proteins are aberrantly activated as a result of oncogenic mutation in other genes (i.e., the Ras gene itself is not activated by mutation to an oncogenic form) with said inhibition being accomplished by the administration of an effective amount of the compounds of the invention to a mammal in need of such treatment. For example, the compounds are useful in the treatment of neurofibromatosis, which is a benign proliferative disorder.

The instant compounds may also be useful in the treatment of certain viral infections, in particular in the treatment of hepatitis delta and related viruses (J. S. Glenn et al. *Science,* 256:1331–1333(1992).

The compounds of the instant invention are also useful in the prevention of restenosis after percutaneous transluminal coronary angioplasty by inhibiting neointimal formation (C. Indolfi et al. *Nature medicine,* 1:541–545(1995).

The instant compounds may also be useful in the treatment and prevention of polycystic kidney disease (D. L. Schaffner et al. *American Journal of Pathology,* 142:1051–1060 (1993) and B. Cowley, Jr. et al.*FASEB Journal,* 2:A3160 (1988)).

The instant compounds may also be useful for the treatment of fungal infections.

In a preferred embodiment of the instant invention the compounds of this instant invention are selective inhibitors of farnesyl-protein transferase. A compound is considered a selective inhibitor of farnesyl-protein transferase, for example, when its in vitro farnesyl-protein transferase inhibitory activity, as assessed by the assay described in Example 12, is at least 100 times greater than the in vitro activity of the same compound against geranylgeranyl-protein transferase-type I in the assay described in Example 13. Preferably, a selective compound exhibits at least 1000 times greater activity against one of the enzymatic activities when comparing geranylgeranyl-protein transferase-type I inhibition and farnesyl-protein transferase inhibition.

In another preferred embodiment of the instant invention the compounds of this instant invention are dual inhibitors of farnesyl-protein transferase and geranylgeranyl-protein transferase type I. Such a dual inhibitor will exhibit certain characteristics when assessed in in vitro assays, which are dependent on the type of assay employed.

In a SEAP assay, such as described in Example 16, it is preferred that the dual inhibitor compound has an in vitro inhibitory activity (IC$_{50}$) that is less than about 12 $\mu$M against K4B-Ras dependent activation of MAP kinases in cells. More preferably, the dual inhibitor compound has an in vitro inhibitory activity (IC$_{50}$) against K4B-Ras dependent activation of MAP kinases in cells which is more than about 5 times lower than the inhibitory activity (IC$_{50}$) against Myr-Ras dependent activation of MAP kinases in cells. Also more preferably, in a SEAP assay, the dual inhibitor compound has an inhibitory activity (IC$_{50}$) that is less than about 10 nM against H-Ras dependent activation of MAP kinases in cells.

In a GGTase plus anion assay, such as described in Example 13, it is preferred that the dual inhibitor compound has an in vitro inhibitory activity (IC$_{50}$) that is less than about 5 $\mu$M against transfer of a geranylgeranyl residue to a protein or peptide substrate comprising a CAAX$^G$ motif by geranylgeranyl-protein transferase type I in the presence of a modulating anion. More preferably, the dual inhibitor compound has an in vitro inhibitory activity (IC$_{50}$) that is less than about 1 $\mu$M against transfer of a geranylgeranyl residue to a protein or peptide substrate comprising a CAAX$^G$ motif by geranylgeranyl-protein transferase type I in the presence of a modulating anion. Preferably, the dual inhibitor compound has an in vitro inhibitory activity (IC$_{50}$) in the in vitro assay as described in Example 12 that is less than about 1 $\mu$M against transfer of a farnesyl residue to a protein or peptide substrate, comprising a CAAX$^F$ motif, by farnesyl-protein transferase. more preferably, the dual inhibitor compound has an in vitro inhibitory activity (IC$_{50}$) that is less than about 100 nM against transfer of a farnesyl residue to a protein or peptide substrate, comprising a CAAX$^F$ motif, by farnesyl-protein transferase. Also preferably, the dual inhibitor compound has an in vitro inhibitory activity (IC$_{50}$) in the in vitro assay as described in Example 15, that is less than about 100 nM against the anchorage independent growth of H-ras-transformed mammalian fibroblasts.

The protein or peptide substrate utilized in the instant assay may incorporate any CAAX motif that is geranylgeranylated by GGTase-I. The term "CAAX$^G$" will refer to such motifs that may be geranylgeranylated by GGTase-I. It is understood that some of the "CAAX$^B$" containing protein or peptide substrates may also be farnesylated by farnesyl-protein transferase. In particular such "CAAX$^G$" motifs include (the corresponding human protein is in parentheses): CVIM (K4B-Ras), CVLL (mutated H-Ras), CVVM (N-Ras), CIIM (K4A-Ras), CLLL (Rap-IA), CQLL (Rap-IB), CSIM, CAIM, CKVL and CLIM (PFX). Preferably, the CAAX motif is CVIM.

As used herein, the term "CAAX$^F$" is used to designate a protein or peptide substrate that incorporates four amino acid C-terminus motif that is farnesylated by farnesyl-protein transferase. It is understood that certain of the "CAAX$^F$" containing protein or peptide substrates may also be geranylgeranylated by GGTase-I. In particular such "CAAX$^F$" motifs include (the corresponding human protein is in parentheses): CVLS (H-ras), CVIM (K4B-Ras) and CVVM (N-Ras).

The compounds of this invention may be administered to mammals, preferably humans, either alone or, preferably, in combination with pharmaceutically acceptable carriers or diluents, optionally with known adjuvants, such as alum, in a pharmaceutical composition, according to standard pharmaceutical practice. The compounds can be administered orally or parenterally, including the intravenous, intramuscular, intraperitoneal, subcutaneous, rectal and topical routes of administration.

For oral use of a chemotherapeutic compound according to this invention, the selected compound may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The present invention also encompasses a pharmaceutical composition useful in the treatment of cancer, comprising the administration of a therapeutically effective amount of the compounds of this invention, with or without pharmaceutically acceptable carriers or diluents. Suitable compositions of this invention include aqueous solutions comprising compounds of this invention and pharmacologically acceptable carriers, e.g., saline, at a pH level, e.g., 7.4. The solutions may be introduced into a patient's intramuscular blood-stream by local bolus injection.

As used herein, the term "composition" is intended to encompass a product comprising the specified ingredients in the specific amounts, as well as any product which results, directly or indirectly, from combination of the specific ingredients in the specified amounts.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a mammal undergoing treatment for cancer. Administration occurs in an amount between about 0.1 mg/kg of body weight to about 60 mg/kg of body weight per day, preferably of between 0.5 mg/kg of body weight to about 40 mg/kg of body weight per day.

The compounds of the instant invention are also useful as a component in an assay to rapidly determine the presence and quantity of farnesyl-protein transferase (FPTase) in a composition. Thus the composition to be tested may be divided and the two portions contacted with mixtures which comprise a known substrate of FPTase (for example a tetrapeptide having a cysteine at the amine terminus) and farnesyl pyrophosphate and, in one of the mixtures, a compound of the instant invention. After the assay mixtures are incubated for an sufficient period of time, well known in the art, to allow the FPTase to farnesylate the substrate, the chemical content of the assay mixtures may be determined by well known immunological, radiochemical or chromatographic techniques. Because the compounds of the instant invention are selective inhibitors of FPTase, absence or quantitative reduction of the amount of substrate in the assay mixture without the compound of the instant invention relative to the presence of the unchanged substrate in the assay containing the instant compound is indicative of the presence of FPTase in the composition to be tested.

It would be readily apparent to one of ordinary skill in the art that such an assay as described above would be useful in identifying tissue samples which contain farnesyl-protein transferase and quantitating the enzyme. Thus, potent inhibitor compounds of the instant invention may be used in an active site titration assay to determine the quantity of enzyme in the sample. A series of samples composed of aliquots of a tissue extract containing an unknown amount of farnesyl-protein transferase, an excess amount of a known substrate of FPTase (for example a tetrapeptide having a cysteine at the amine terminus) and farnesyl pyrophosphate are incubated for an appropriate period of time in the presence of varying concentrations of a compound of the instant invention. The concentration of a sufficiently potent inhibitor (i.e., one that has a Ki substantially smaller than the concentration of enzyme in the assay vessel) required to inhibit the enzymatic activity of the sample by 50% is approximately equal to half of the concentration of the enzyme in that particular sample.

EXAMPLES

Examples provided are intended to assist in a further understanding of the invention. Particular materials employed, species and conditions are intended to be further illustrative of the invention and not limitative of the reasonable scope thereof. Purification by HPLC was utilized for Example 1 as set forth below.

Example 1

Preparation of 2-Benzyl-1,2,3,4-tetrahydro-isoquinoline-3 (S)-carboxylic acid {2-[3-(4-cyanobenzyl)-3H-imidazol-4-yl]-ethyl}-amide Step A:

Preparation of 3-(4-cyanobenzyl) histamine

N$\gamma$-Pivaloyloxymethyl-N$^\alpha$-phthaloylhistamine (4.55 g, 12.8 mmol) was prepared as previously described (J. C. Emmett, F. H. Holloway, and J. L. Turner, *J. Chem. Soc., Perkin Trans.* 1, 1341, (1979)). $\alpha$-Bromo-p-tolunitrile (3.77 g, 19.2 mmol) was dissolved in acetonitrile (70 mL). The solution was heated at 55° C. for 4 h, cooled to room temperature, and filtered to remove the white solid. The acetonitrile (30 mL) was concentrated to ½ its volume under reduced pressure and the solution was heated at 55° C. overnight. The solution was cooled and filtered to give a white solid. The volume of the filtrate was reduced to 10 mL, the solution was heated at 55° C. for 1 hr, then cooled to room temperature, diluted with EtOAc (25 mL) and filtered to obtain additional white solid. The solids were combined, dried, and used without further purification.

1-Pivaloyloxymethyl-3-(4-cyanobenzyl)-4-(2-phthalimidoethyl)imidazolium bromide (6.13 g, 11.1 mmol) in methanol (100 mL) was saturated with ammonia gas while the temperature was maintained below 30° C. The solution was stirred for 1 hr, concentrated to dryness, and extracted with CH$_2$Cl$_2$ (3×200 mL), dried (MgSO$_4$), concentrated, and chromatographed (silica gel, 10:90:1 MeOH/CH$_2$Cl$_2$/NH$_4$OH) to give 4-cyanobenzyl-N$^\alpha$-phthaloylhistamine.

3-(4-Cyanobenzyl)-N$^\alpha$-phthaloylhistamine (1.64 g, 4.61 mmol), and hydrazine (1.46 mL, 46.1 mmol) were dissolved in absolute EtOH (70 mL). The solution was concentrated after 1 hr and filtered to remove a white precipitate which was washed several times with EtOH. The filtrate was concentrated and the residue was chromatographed (silica gel, 10:90:1 MeOH/CH$_2$Cl$_2$/NH$_4$OH) to give the title compound.

Step B:

Preparation of 2-(t-Butyloxycarbonyl)-1,2,3,4-tetrahydro-isoquinoline-3(S)-carboxylic acid {2-[3-(4-cyanobenzyl)-3H-imidazol-4-yl]-ethyl}-amide To a solution of 2-(t-butyloxycarbonyl)-1,2,3,4-tetrahydro-isoquinoline-3(S)-carboxylic acid (0.15 g, 0.54 mmol) and 3-(4-cyanobenzyl) histamine (0.122 g, 0.54 mmol) in DMF (5 mL) was added 1-hydroxybenzotriazole (0.083 g, 0.54 mmol), EDC (0.104 g, 0.54 mmol), and N-methylmorpholine (0.24 mL, 2.16 mmol). After stirring for 18 hr. the mixture was evaporated in vacuo and the residue was partitioned with EtOAc (50 mL) and saturated NaHCO$_3$ (30 mL). The organic layer was washed with saturated NaCl solution (30 mL) and dried (MgSO$_4$). Filtration was done which gave the title compound.

$^1$H NMR (400 MHz, CDCl$_3$) $\delta$7.60 (2H, d, J=8 Hz), 7.46 (1H,s), 7.24–7.06 (4H, b), 7.18 (1H,s), 7.07 (2H, d, J=8 Hz), 6.76 (1H, b), 5.08 (2H, s), 1.46 (9H, s).

Step C:

Preparation of 1,2,3,4-Tetrahydro-isoquinoline-3(S)-carboxylic acid {2-[3-(4-cyanobenzyl)-3H-imidazol-4-yl]-ethyl}-amide hydrochloride A solution of 2-(t-butyloxycarbonyl)-1,2,3,4-tetrahydroisoquinoline-3(S)-carboxylic acid {2-[3-(4-cyanobenzyl)-3H-imidazol-4-yl]-ethyl}-amide (0.25 g, 0.52 mmol) in EtOAc (15 mL) was cooled to −20° C. The solution was saturated with HCl gas and stirred at 0° C. for 0.5 hr and 25° C. for an additional 0.5 hr. The reaction was evaporated in vacuo to obtain the title compound which was used without further purification.

Step D:
Preparation of 2-Benzyl-1,2,3,4-tetrahydro-isoquinoline-3 (S)-carboxylic acid {2-[3-(4-cyanobenzyl)-3H-imidazol-4-yl]-ethyl}-amide 1,2,3,4-Tetrahydro-isoquinoline-3(S)-carboxylic acid {2-[3-(4-cyanobenzyl)-3H-imidazol-4-yl]-ethyl}-amide hydrochloride (0.15 g, 0.33 mmol) was dissolved in MeOH (7 mL). $Et_3N$ was added to this solution dropwise until the pH=5. To the solution was added benzaldehyde (0.069 mL, 0.65 mmol) and sodium cyanoborohydride (0.041 g, 0.65 mmol). After stirring for 18 hr. the mixture was evaporated in vacuo and the residue was partitioned between EtOAc (50 mL) and saturated $NaHCO_3$ (30 mL). The organic layer was washed with saturated NaCl solution (30 mL) and dried ($MgSO_4$). Filtration and concentration to dryness gave the title compound after purification on silica gel eluting with $CH_2Cl_2$:
MeOH: $NH_4OH$, 98:2:0.2.
$^1H$ NMR (400 MHz, $CD_3OD$) δ7.70 (1H, s), 7.62 (2H, d, J=8 Hz), 7.30 (5H, m), 7.19 (2H, d, J=8 Hz), 7.12 (3H, m), 6.99 (1H, m), 6.79 (1H, s), 5.27 (2H, s), 3.42 (1H, t, J=6 Hz), 3.02 (2H, d, J=6 Hz), 2.50 (2H, m).
Anal. calculated for $C_{30}H_{29}N_5O.0.80$ $H_2O$: C, 73.54; H, 6.29; N, 14.29; Found C, 73.52; H, 6.13; N, 14.38.

Using the methods described above but using the appropriate commercially available aldehydes in place of benzaldehyde in Step D, the following compounds were prepared:

2-(2-Chlorobenzyl)-1,2,3,4-tetrahydro-isoquinoline-3(S)-carboxylic acid {2-[3-(4-cyanobenzyl)-3H-imidazol-4-yl]-ethyl}-amide
Anal. calculated for $C_{30}H_{28}N_5OCl.1.00$ $H_2O$: C, 68.24; H, 5.73; N, 13.26; Found C, 68.29; H, 5.80; N, 13.53.

2-(3-Chlorobenzyl)-1,2,3,4-tetrahydro-isoquinoline-3(R)-carboxylic acid {2-[3-(4-cyanobenzyl)-3H-imidazol-4-yl]-ethyl}-amide
Anal. calculated for $C_{30}H_{28}N5OCl.1.10$ $H_2O$: C, 68.01; H, 5.75; N, 13.22; Found C, 67.97; H, 5.56; N, 12.97.

2-(3-Chlorobenzyl)-1,2,3,4-tetrahydro-isoquinoline-3(S)-carboxylic acid {2-[3-(4-cyanobenzyl)-3H-imidazol-4-yl]-ethyl}-amide trifluoroacetate
Anal. calculated for $C_3OH_{28}N_5OCl.2.90$ $CF3CO2H.0.90$ $H_2O$: C, 50.18; H, 3.85; N, 8.17; Found C, 50.22; H, 3.85; N, 8.24.

2-(4-Chlorobenzyl)-1,2,3,4-tetrahydro-isoquinoline-3(S)-carboxylic acid {2-[3-(4-cyanobenzyl)-3H-imidazol-4-yl]-ethyl}-amide
Anal. calculated for $C_{30}H_{28}N_5OCl.0.80$ $H_2O$: C, 68.71; H, 5.69; N, 13.35; Found C, 68.70; H, 5.62; N, 13.58.

2-(2-Phenylethyl)-1,2,3,4-tetrahydro-isoquinoline-3(S)-carboxylic acid {2-[3-(4-cyanobenzyl)-3H-imidazol-4-yl]-ethyl}-amide
Anal. calculated for $C_{31}H31N_5O.0.90$ $H_2O$: C, 73.61; H, 6.54; N, 13.85; Found C, 73.55; H, 6.31; N, 14.16.

2-(2,2-Diphenylethyl)-1,2,3,4-tetrahydro-isoquinoline-3(S)-carboxylic acid {2-[3-(4-cyanobenzyl)-3H-imidazol-4-yl]-ethyl}-amide
Anal. calculated for $C_{37}H35N_5O.1.00$ $H_2O$: C, 76.13; H, 6.39; N, 12.00; Found C, 76.01; H, 6.12; N, 12.02.

2-(3-Trifluoromethoxybenzyl)-1,2,3,4-tetrahydro-isoquinoline-3(S)-carboxylic acid {2-[3-(4-cyanobenzyl)-3H-imidazol-4-yl]-ethyl}-amide
Anal. calculated for $C_{31}H_{28}N_5O_2F_3.0.80$ $H_2O$: C, 64.87; H, 5.20; N, 12.20; Found C, 64.78; H, 5.04; N, 12.15.

2-(n-Butyl)-1,2,3,4-tetrahydro-isoquinoline-3(S)-carboxylic acid {2-[3-(4-cyanobenzyl)-3H-imidazol-4-yl]-ethyl}-amide trifluoroacetate
Anal. calculated for $C_{27}H31N_5O.2.3$ $CF_3CO_2H.0.60$ $H_2O$: C, 53.11; H, 4.87; N, 9.80; Found C, 53.06; H, 4.87; N, 10.08.

2-(3-Pyridylmethyl)-1,2,3,4-tetrahydro-isoquinoline-3(S)-carboxylic acid {2-[3-(4-cyanobenzyl)-3H-imidazol-4-yl]-ethyl}-amide trifluoroacetate
Anal. calculated for $C_{29}H_{28}N_6O.3.5$ $CF_3CO_2H.0.40$ $H_2O$: C, 48.98; H, 3.69; N, 9.52; Found C, 48.95; H, 3.68; N, 9.44.

2-(3-Trifluoromethoxybenzyl)-1,2,3,4-tetrahydro-isoquinoline-3(R)-carboxylic acid {2-[3-(4-cyanobenzyl)-3H-imidazol-4-yl]-ethyl}-amide trifluoroacetate
Anal. calculated for $C_{31}H_{28}N_5O_2F_3.2.8$ $CF_3CO_2H.0.50$ $H_2O$: C, 49.51; H, 3.61; N, 7.89; Found C, 49.48; H, 3.63; N, 7.84.
FAB MS (M+1) 560

2-(3-Methoxyphenyl)-1,2,3,4-tetrahydro-isoquinoline-3(R)-carboxylic acid {2-[3-(4-cyanobenzyl)-3H-imidazol-4-yl]-ethyl}-amide trifluoroacetate
Anal. calculated for $C_{31}H_{31}N_5O_2.2.9$ $CF3CO2H.0.20$ $H_2O$: C, 52.63; H, 4.12; N, 8.34; Found C, 52.66; H, 4.19; N, 8.17.

Using the methods described above but substituting 2-(t-butyloxycarbonyl)-7-hydroxy-1,2,3,4-tetrahydro-isoquinoline-3(S)-carboxylic acid for 2-(t-butyloxycarbonyl)-1,2,3,4-tetrahydro-isoquinoline-3(S)-carboxylic acid in Step B, the following compound was prepared:

2-(3-Chlorobenzyl)-7-hydroxy-1,2,3,4-tetrahydro-isoquinoline-3 (S)-carboxylic acid {2-[3-(4-cyanobenzyl)-3H-imidazol-4-yl]-ethyl}-amide
Anal. calculated for $C_{30}H_{28}N_5O_2Cl.0.30$ $H_2O$: C, 67.80; H, 5.42; N, 13.18; Found C, 67.78; H, 5.45; N, 12.95.

Using the methods described above but substituting 2-methylhistamine for histamine in Step A, the following compounds were prepared:

2-(3-Chlorobenzyl)-1,2,3,4-tetrahydro-isoquinoline-3 (S)-carboxylic acid {2-[3-(4-cyanobenzyl)-2-methyl-3H-imidazol-4-yl]-ethyl}-amide trifluoroacetate
Anal. calculated for $C_{31}H_{30}N_5OCl.2.50$ $CF3CO2H.1.30$ $H_2O$: C, 51.94; H, 4.25; N, 8.41; Found C, 51.98; H, 4.26; N, 8.25.

2-(3-Trifluoromethoxybenzyl)-1,2,3,4-tetrahydro-isoquinoline-3 (S)-carboxylic acid {2-[3-(4-cyanobenzyl)-2-methyl-3H-imidazol-4-yl]-ethyl}-amide
Anal. calculated for $C_{32}H30N_5O_2F_3.0.80$ $H_2O$: C, 65.36; H, 5.42; N, 11.91; Found C, 65.35; H, 5.33; N, 11.85.

Example 2
Preparation of 2-(2,3-Dimethylbenzoyl)-1,2,3,4-tetrahydro-isoquinoline-3(S)-carboxylic acid {2-[3-(4-cyanobenzyl)-3H-imidazol-4-yl]-ethyl}-amide To a solution of 1,2,3,4-Tetrahydro-isoquinoline-3(S)-carboxylic acid {2-[3-(4-cyanobenzyl)-3H-imidazol-4-yl]-ethyl}-amide hydrochloride (Example 1, Step C) (0.23 g, 0.52 mmol) in DMF (5 mL) was added 1-hydroxybenzotriazole (0.079 g, 0.52 mmol), EDC (0.099 g, 0.52 mmol), 2,3-dimethylbenzoic acid (0.077 g, 0.52 mmol) and N-methylmorpholine (0.23 mL, 2.08 mmol). After stiffing for 18 hr. the mixture was evaporated in vacuo and the residue was partitioned betweem EtOAc (50 mL) and saturated $NaHCO_3$ solution (30 mL). The organic layer was washed with saturated NaCl solution (30 mL) and dried ($MgSO_4$). Filtration and concentration gave the title compound after purification by preparative HPLC on a Delta-pak C-18 column eluting with 0.1%TFA/$H_2O$: 0.1%TFA/$CH_4CN$, 95:5 to 5:95.
Anal. calculated for $C_{32}H_{31}N_5O_2.1.7$ $CF_3CO_2H.0.50$ $H_2O$: C, 59.02; H, 4.71; N, 9.72; Found C, 58.96; H, 4.69; N, 9.64.

Example 3
Preparation of 2-(3-Chlorophenylsulfonyl)-1,2,3,4-tetrahydro-isoquinoline-3(S)-carboxylic acid {2-[3-(4-cyanobenzyl)-3H-imidazol-4-yl]-ethyl}-amide Step A:
Preparation of 1,2,3,4-Tetrahydro-isoquinoline-3(S)-carboxylic acid {2-[3-(4-cyanobenzyl)-3H-imidazol-4-yl]-ethyl}-amide trifluoroacetate To a solution of 2-(t-butyloxycarbonyl)-1,2,3,4-tetrahydro-isoquinoline-3(S)-carboxylic acid {2-[3-(4-cyanobenzyl)-3H-imidazol-4-yl]-ethyl}-amide (1.18 g, 2.4 mmol) in $CH_2Cl_2$ (6 mL) was added $CF_3CO_2H$ (4 mL). The reaction was stirred for 0.75 hr at 25° C. Evaporation in vacuo yielded the title compound.

Step B:
Preparation of 2-(3-Chlorophenylsulfonyl)-1,2,3,4-tetrahydro-isoquinoline-3(S)-carboxylic acid {2-[3-(4-cyanobenzyl)-3H-imidazol-4-yl]-ethyl}-amide To a solution of 1,2,3,4-Tetrahydro-isoquinoline-3(S)-carboxylic acid {2-[3-(4-cyanobenzyl)-3H-imidazol-4-yl]-ethyl}-amide-trifluoroacetate (1.0 g, 1.63 mmol) in $CH_2Cl_2$ (15 mL) was added $Et_3N$ (0.82 mL, 6.52 mmol). The solution was cooled to 0° C. and 3-chlorophenylsulfonyl chloride (0.413 mL, 1.96 mmol) was added dropwise. The reaction was stirred for 18 hr at 25° C. under a nitrogen atmosphere. The mixture was partitioned between $CH_2Cl_2$ (50 mL) and saturated $NaHCO_3$ solution (30 mL). The organic layer was washed with saturated NaCl solution (30 mL) and dried ($MgSO_4$). Filtration and concentration in vacuo the title compound after purification by preparative HPLC on a Delta-pak C-1 8 column eluting with 0.1%TFA/$H_2O$: 0.1%TFA/$CH_3CN$, 95:5 to 5:95 and conversion to the free base.

Anal. calculated for $C_{29}H_{26}N_5O_3S.1.30 H_2O$: C, 59.70; H, 4.94; N, 12.00; Found C, 59.78; H, 4.80; N, 11.56.

Example 4
Preparation of 2-(3-Chlorobenzyl)-7-methoxy-1,2,3,4-tetrahydro-isoquinoline-3(S)-carboxylic acid {2-[3-(4-cyanobenzyl)-3H-imidazol-4-yl]-ethyl}-amide Step A:
Preparation of Methyl 2-(t-butyloxycarbonyl)-7-hydroxy-1,2,3,4-tetrahydroisoquinoline-3(S)-carboxylate 2-(t-Butyloxycarbonyl)-7-hydroxy-tetrahydro-isoquinoline-3-carboxylic acid (0.5 g, 1.71 mmol) was dissolved in 10% MeOH/$CHCl_3$ (70 mL). The solution was cooled to 0° C. and trimethylsilyldiazomethane (2 M in hexane) (1.88 mL, 3.76 mmol) was added dropwise via syringe. A yellow color persisted after addittion of 1.2 mL of this reagent. The cooling bath was removed and the solution was stirred at 25° C. for 0.75 hr. The reaction was cooled to 0° C. and acetic acid was added dropwise until the yellow color disappeared. The solvent was evaporated in vacuo and the residue was partitioned between EtOAc (50 mL) and saturated $NaHCO_3$ solution (30 mL). The organic layer was washed with saturated NaCl solution (30 mL) and dried ($MgSO_4$). Filtration and evaporation in the title compound which was used without further purification.

Step B:
Preparation of Methyl 2-(t-butyloxycarbonyl)-7-methoxy-1,2,3,4-tetrahydroisoquinoline-3(S)-carboxylate To a solution of Methyl 2-(t-butyloxycarbonyl)-7-hydroxy-1,2,3,4-tetrahydroisoquinoline-3(S)-carboxylate (0.615 g, 2.0 mmol) in DMF (7 mL) was added $K_2CO_3$ (0.304 g, 2.2 mmol) and iodomethane (0.137 mL, 2.2 mmol). The mixture was stirred for 18 hr at 25° C. Approximately 14% of the starting material remained. An additional amount of iodomethane (0.050 mL) was added and stirring continued for 18 hr. The DMF was evaporated in vacuo and the residue was partitioned between EtOAc (50 mL) and saturated $NaHCO_3$ (30 mL). The ethyl acetate layer was washed with saturated NaCl solution (30 mL) and dried ($MgSO_4$). Filtration and evaporation in vacuo gave the title compound.

Step C:
Preparation of 2-(t-Butyloxycarbonyl)-7-methoxy-1,2,3,4-tetrahydroisoquinoline-3(S)-carboxylic acid To a solution of Methyl 2-(t-butyloxycarbonyl)-7-methoxy-1,2,3,4-tetrahydroisoquinoline-3(S)-carboxylate (0.58 g, 1.81 mmol) in MeOH:$H_2O$ 1:1 (20 mL) was added 1 N NaOH (2.7 mL, 2.72 mmol) and the resulting solution was stirred at 25° C. for 18 hr. The methanol was evaporated in vacuo and the remaining aqueous portion was acidified to pH=3 with 1 N HCl and then extracted two times with EtOAc. The organic layers were washed with saturated NaCl (30 mL) and dried ($MgSO_4$). Filtration and evaporation in vacuo gave the title compound.

$^1H$ NMR (400 MHz, $CD_3OD$) δ7.07 (1H, t, J=7 Hz), 6.74 (2H, m), 3.75 (3H, s), 1.5 (9H, d).

Step D:
Preparation of 2-(3-Chlorobenzyl)-7-methoxy-1,2,3,4-tetrahydro-isoquinoline-3(S)-carboxylic acid {2-[3-(4-cyanobenzyl)-3H-imidazol-4-yl]-ethyl}-amide Following the procedures outlined in Example 1, Steps B, C and D, but substituting the compound described in Step C above for 2-(t-butyloxycarbonyl)-1,2,3,4-tetrahydro-isoquinoline-3(S)-carboxylic acid, the title compound was prepared.

Anal. calculated for $C_{31}H_{30}N_5O_2Cl.2.5$ HCl.0.25 $H_2O$: C, 58.56; H, 5.23; N, 11.02; Found C, 58.53; H, 5.23; N, 10.20. FAB MS (M+1) 540

Using the methods described in Examples 1 and 4, the following compound was prepared:

2-n-Butyl-7-methoxy- 1,2,3,4-tetrahydro-isoquinoline-3 (S)-carboxylic acid {2-[3-(4-cyanobenzyl)-3H-imidazol-4-yl]-ethyl}-amide Anal. calculated for $C_{28}H33N_5O_2.0.65 H_2O$: C, 69.58; H, 7.15; N, 14.49; Found C, 69.61; H, 7.21; N, 14.29.

Example 5
Preparation of 4-{3-[2-(3-chlorobenzyl)-(S)-1,2,3,4-tetrahydro-isoguinolin-3-yl-methyl]-3H-imidazol-4-yl-methyl}-benzonitrile Step A:
Preparation of Boc-(S)-(3-hydroxy methyl)-1,2,3,4-tetrahydroisoquinoline To a solution of Boc-(S)-1,2,3,4-tetrahydroisoquinoline-3-carboxylic acid (10 g, 36.1 mmol) dissolved in 250 ml THF at 0° C. was added 72.2 ml of a 1 M $BH_3$.THF (72.2 mmol) solution dropwise. The mixture was stirred for 2 hr. at 0° C. and then for 18 hr at 25° C. The solvents were removed in vacuo and the residue was partitioned between ethyl acetate and saturated sodium bicarbonate. The ethyl acetate layer was dried with saturated sodium chloride and magnesium sulfate. Evaporation in vacuo of the ethyl acetate layer yielded the title compound as an oil, which was used in the next step without further purification.

NMR (400 MHz, $CDCl_3$) d 7.24–7.09 (4H, m), 4.72 (1H, s, b), 4.5 (1H, s, b), 4.32 (1H, d, b, J=16 Hz), 3.52 (2H, s, b), 3.05 (1H, dd, J=10, 6 Hz), 2.80 (1H, d, b, J=16 Hz), 1.49 (9H, s).

Step B:
Preparation of (S)-3-(hydroxymethyl)-1,2,3,4-tetrahydroisoquinoline hydrochloride A solution of Boc-(S)- (3-hydroxy methyl)-1,2,3,4-tetrahydroisoquinoline (4g, 17.2 mmol) in 75 ml ethyl acetate was cooled to −20° C. The solution was saturated with hydrogen chloride gas. The reaction was allowed to warm to 25° C. and stirred for 1 hr. The solvent was removed in vacuo to obtain the title compound as a solid, which was used in the next step without further purification.

Step C:
Preparation of (S)-[2-(3-chloro-benzyl)-3-(hydroxymethyl)]-1,2,3,4-tetrahydro-isoquinoline A solution of (S)-3-(hydroxymethyl)-1,2,3,4-tetrahydroisoquinoline hydrochloride (0.3 g,1.5 mmol) in 7 ml of methanol was adjusted to a pH=4 with triethylamine. To this solution was added 3-chlorobenzaldehyde (0.34 ml, 3.0 mmol) and sodium cyanoborohydride (0.28 g, 4.5 mmol). The mixture was stirred for 18 hr at 25° C. The reaction was quenched with 2 ml water and the solvent was removed in vacuo. The residue was partitioned between ethyl acetate and saturated sodium bicarbonate. The ethyl acetate layer was dried with saturated sodium chloride and magnesium sulfate. Evaporation in vacuo of the ethyl acetate layer yielded the crude product. Purification was done on silica gel using methylene chloride:methanol:amonia hydroxide 98:2:0.2 yielded the title compound.

Step D:
Preparation of 4-{3-[2-(3-chlorobenzyl)-(S)-1,2,3,4-tetrahydro-isoquinolin-3-yl-methyl]-3H-imidazol-4-yl-methyl}-benzonitrile To a solution of (S)-[2-(3-chloro-benzyl)-3-(hydroxymethyl)]-1,2,3,4-tetrahydro-isoquinoline (0.21 g, 0.73 mmol) and 1-trityl-4-(4-cyanobenzyl) imidazole (0.31 g, 0.73 mmol) and di-isopropylethylamine (0.508 ml, 2.92 mmol) in 7 ml methylene chloride at −78° C. was added triflic anhydride (0.125 ml, 0.73 mmol). The reaction was allowed to warm to 25° C. and stirred for 18 hr. The solvent was removed in vacuo and the residue was dissolved in 20 ml of methanol and refluxed for 1 hr. The solvent was removed in vacuo and the residue was partitioned between ethyl acetate and saturated sodium bicarbonate. The ethyl acetate layer was dried with saturated sodium chloride and magnesium sulfate. Evaporation in vacuo of the ethyl acetate layer yielded the crude product. Purification was done on silica gel using methylene chloride:methanol:amonia hydroxide 98:2:0.2 yielded the title compound as a solid. FAB mas spectrum m/e 453 (m+1). Analysis calculated for $C_{28}H_{25}N_4O_1 \cdot 0.3\, H_2O$: C, 73.37; H, 5.63; N, 12.22. Found: C, 73.54; H, 5.83; N, 11.98.

Example 6
Preparation of 4-{3-[2-(1-(5-chloro-pyridin-2-one)ethyl)-(S)-1,2,3,4-tetrahydro-isoquinolin-3-yl-methyl]-3H-imidazol-4-yl-methyl}-benzonitrile di-trifluoro acetate salt Step A:
Preparation of Ethyl 5-chloropyridin-2-one -1-acetate To a solution of 5-chloropyridin-2-one (2 g, 15.4 mmol) and potassium hydroxide (0.86 g, 15.4 mmol) in 70 ml ethanol was added Ethyl bromoacetate (1.88 ml, 16.98 mmol). The mixture was heated to reflux for 4 hr. A precipitate was removed by filtration and the solvent was removed from the filtrate in vacuo to yield the crude product. Purification on silica gel using hexane:ethyl acetate 6:4 yielded the title compound as a solid.

Step B:
Preparation of 1-hydroxyethyl-5-chloropyridin-2-one

To a solution of ethyl 5-chloropyridin-2-one -1-acetate (2.3 g, 10.67 mmol) in 50 ml THF at 0° C. was added 10.67 ml lithium borohydride (1 M in THF, 21.34 mmol). The reaction was allowed to warm to 25° C. and stirred for 2 hr. The solution was cooled to 0° C. and quenched with methanol. The solvents were removed in vacuo and the residue was dissolved in 75 ml methanol and refluxed for 1 hr. The methanol was removed in vacuo to give the crude product. Purification was done on silica gel using hexane:ethyl acetate 95:5 yielded the title compound as a solid.
NMR (400 MHz, CD$_3$OD) d 7.75 (1H, d, J=3 Hz), 7.52 (1H, dd, J=7,3 Hz), 6.54 (1H, d, J=10 Hz), 4.07 (2H, t, J=5 Hz), 3.81 (2H, t, J=5 Hz).

Step C:
Preparation of (S)-{2-[1-(5-chloro-pyridin-2-one)ethyl]-3-(hydroxymethyl)}-1,2,3,4-tetrahydroisoquinoline To a solution of 1-hydroxyethyl-5-chloropyridin-2-one (0.26 g, 1.5 mmol) and triethylamine (0.278 ml, 2.0 mmol) in 5 ml methylene chloride at 0° C. was added methane sulfonyl chloride (0.116 ml, 1.5 mmol). The mixture was stirred for 10 minutes and a solution of (S)-3-(hydroxymethyl)-1,2,3,4-tetrahydroisoquinoline hydrochloride (0.2 g, 1.0 mmol) and triethylamine (0.139 ml, 1.0 mmol) in 3 ml of acetonitrile was added. The reaction was stirred at 25° C. for 18 hr. The solvents were removed in vacuo to obtain the crude product which was chromatographed on silica gel using methylene chloride:methanol:amonia hydroxide 98:2:0.2 yielded the title compound.

Step D:
Preparation of 4-{3-[2-(1-(5-chloro-pyridin-2-one)ethyl)-(S)-1,2,3,4-tetrahydro-isoquinolin-3-yl-methyl]-3H-imidazol-4-yl-methyl}-benzonitrile di-trifluoro acetate salt The same procedure as described in Step D of Example 5 above was used to mix (S)-{2-[1-(5-chloro-pyridin-2-one)ethyl]-3-(hydroxymethyl)}-1,2,3,4-tetrahydroisoquinoline (0.07 g, 0.22 mmol), 1-trityl-4-(4-cyanobenzyl)imidazole (0.094 g, 0.22 mmol), diisopropylethylamine (0.153 ml, 0.88 mmol), and triflic anhydride (0.037 ml, 0.22 mmol) in 4 ml methylene chloride. The crude product was obtained which was purified by preparative HPLC to obtain the title compound as a solid.
FAB mas spectrum m/e 484 (m+1).

Example 7
Preparation of 4-{3-[2-(methylsulfonylethyl)-(S)-1,2,3,4-tetrahydro-isoquinolin-3-yl-methyl]-3H-imidazol-4-yl-methyl}-benzonitrile Step A:
Preparation of (S)-[2-(methylsulfonylethyl)-3-(hydroxymethyl)]-1,2,3,4-tetrahydroisoquinoline To a solution of (S)-3-(hydroxymethyl)-1,2,3,4-tetrahydroisoquinoline hydrochloride (0.25 g, 1.25 mmol) and triethylamine (0.348 ml, 2.5 mmol) in 10 ml acetonitrile was added methylvinyl sulfone (0.264 ml, 3.0 mmol). The mixture was stirred 18 hr at 25° C. The solvents were removed in vacuo to obtain the crude product which was chromatographed on silica gel using methylene chloride:methanol:amonia hydroxide 98:2:0.2 yielded the title compound.

Step B:
Preparation of 4-{3-[2-(methylsulfonylethyl)-(S)-1,2,3,4-tetrahydro-isoquinolin-3-yl-methyl]-3H-imidazol-4-yl-methyl}-benzonitrile The same procedure as described in step D of Example 5 above was used to mix (S)-[2-(methylsulfonylethyl)-3-(hydroxymethyl)]-1,2,3,4-tetrahydroisoquinoline (0.12 g, 0.445 mmol), 1-trityl-4-(4-cyanobenzyl)imidazole (0.19 g, 0.445 mmol), diisopropylethylamine (0.31 ml, 1.78 mmol), and triflic anhydride (0.075 ml, 0.445 mmol) in 5 ml methylene chloride. The crude product was obtained which was chromatographed on silica gel using methylene chloride:methanol:amonia hydroxide 98:2:0.2 and yielded the title compound.
FAB mas spectrum m/e 433 (m+1). Analysis calculated for $C_{24}H_{26}N_4O_2 S \cdot 1.0\, H_2O$: C, 63.70; H, 6.24; N, 12.38. Found: C, 63.72; H, 6.06; N, 11.99.

Example 8
Preparation of 4-{3-[2-(3-methoxybenzoyl)-(S)-1,2,3,4-tetrahydro-isoquinolin-3-yl-methyl]-3H-imidazol-4-yl-methyl}-benzonitrile Step A:
Preparation of (S)-[2-(allyl)-3-(hydroxymethyl)]-1,2,3,4-tetrahydroisoquinoline To a solution of (S)-3-(hydroxymethyl)-1,2,3,4-tetrahydroisoquinoline hydrochloride (1.34 g, 6.71 mmol) and triethylamine (3.73 ml, 26.8 mmol) in 25 ml acetonitrile was added allyl bromide (1.16 ml, 13.4 mmol). The mixture was stirred for 2 hr at 25° C. The solvent was removed in vacuo and the residue was partitioned between ethyl acetate and saturated sodium bicarbonate. The ethyl acetate layer was dried with saturated sodium chloride and magnesium sulfate. Evaporation in vacuo of the ethyl acetate layer yielded the crude product. Purification was done on silica gel using methylene chloride:methanol:amonia hydroxide 98:2:0.2 and yielded the title compound.
NMR (400 MHz, $CDCl_3$) d 7.20–7.00 (4H, m), 5.89 (1H, m), 5.17 (2H, m), 3.85 (2H, dd, J=76, 16 Hz), 3.58 (2H, m), 3.2 (3H, m), 2.88 (1H, dd, J=11, 6Hz), 2.53 (1H, dd, J=11, 6 Hz).

Step B:
Preparation of 4-{3-[2-(allyl)-(S)-1,2,3,4-tetrahydro-isoquinolin-3-yl-methyl]-3H-imidazol-4-yl-methyl}-benzonitrile Proceedure same as step 4 above using (S)-[2-(allyl)-3-(hydroxymethyl)]-1,2,3,4-tetrahydroisoquinoline (0.5 g, 2.46 mmol), 1-trityl-4-(4-cyanobenzyl)imidazole (1.05 g, 2.46 mmol), diisopropylethylamine (1.71 ml, 9.84), and triflic anhydride (0.414 ml, 2.46 mmol) in 7 ml methylene chloride. The crude product was obtained which was chromatographed on silica gel using methylene chloride:methanol:amonia hydroxide 98:2:0.2 and yielded the title compound.
NMR (400 MHz, $CDCl_3$) d 7.53 (2H, d, J=8 Hz), 7.43 (1H, s), 7.24–7.20 (2H, m), 7.12–7.05 (4H, m), 6.83 (1H, s), 5.79 (1H, m), 5.17 (2H, m), 3.88 (2H, dd, J=30, 16 Hz), 3.76 (2H, m), 3.53 (1H, m), 3.25–3.10 (3H, m), 2.85 (1H, dd), 2.40 (1H, dd).

Step C:
Preparation of 4-{3-[(S)-1,2,3,4-tetrahydro-isoquinolin-3-yl-methyl]-3H-imidazol-4-yl-methyl}-benzonitrile A solution of 4-{3-[2-(allyl)-(S)-1,2,3,4-tetrahydro-isoquinolin-3-yl-methyl]-3H-imidazol-4-yl-methyl}-benzonitrile (0.56 g, 1.52 mmol) in 7 ml degassed methylene chloride was added to palladium tetrakistriphenylphosphine (0.045 g, 0.04 mmol) and 1,3-dimethylbarbituric acid (0.712 g, 4.56 mmol) under argon atmosphere. The resulting solution was heated at 35° C. for 3 hr. The mixture was partitioned with methylene chloride, saturated sodium carbonate and water. The methylene chloride layer was dried with saturated sodium chloride and magnesium sulfate. The methylene chloride was removed in vacuo to obtain the title compound as an oil which was used in the next step without further purification.

Step D:
Preparation of 4-{3-[2-(3-methoxybenzoyl)-(S)-1,2,3,4-tetrahydro-isoquinolin-3-yl-methyl]-3H-imidazol-4-yl-methyl}-benzonitrile A mixture of 4-{3-[(S)-1,2,3,4-tetrahydro-isoquinolin-3-yl-methyl]-3H-imidazol-4-yl-methyl}-benzonitrile (0.16 g, 0.487 mmol), 3-methoxybenzoic acid (0.074 g, 0.487 mmol), 1-hydroxybenzotriazole (0.075 g, 0.487 mmol), EDC (0.093 g, 0.487 mmol) and N-methylmorpholine (0.2 ml, 1.95 mmol) in 5 ml DMF was stirred for 18 hr at 25° C. The solvent was removed in vacuo. The residue was partitioned between ethyl acetate and saturated sodium bicarbonate. The ethyl acetate layer was dried with saturated sodium chloride and magnesium sulfate. Evaporation in vacuo of the ethyl acetate layer yielded the crude product. Purification was done on silica gel using methylene chloride:methanol:amonia hydroxide 98:2:0.2 and yielded the title compound.
FAB mas spectrum m/e 463 (m+1). Analysis calculated for $C_{29}H_{26}N_4O_2 \cdot 1.4 H_2O$: C, 71.41; H, 5.95; N, 11.49. Found: C, 71.50; H, 5.67; N, 10.96.

Example 9
Preparation of 4-{3-[2-(3-methoxyphenylacetyl)-(S)-1,2,3,4-tetrahydro-isoquinolin-3-yl-methyl]-3H-imidazol-4-yl-methyl}-benzonitrile The same proceedure as described in step D of Example 8 above was used to mix 4-{3-[(S)-1,2,3,4-tetrahydro-isoquinolin-3-yl-methyl]-3H-imidazol-4-yl-methyl}-benzonitrile (0.16 g, 0.487 mmol), 3-methoxyphenylacetic acid (0.081 g, 0.487 mmol), 1-hydroxybenzotriazole (0.075 g, 0.487 mmol), EDC (0.093 g, 0.487 mmol) and N-methylmorpholine (0.2 ml, 1.95 mmol) in 5 ml DMF. The title compound was obtained.
FAB mas spectrum m/e 477 (m+1). Analysis calculated for $C_{30}H_{28}N_4O_2 \cdot 0.8 H_2O$: C, 73.39; H, 6.08; N, 11.41. Found: C, 73.36; H, 5.81; N, 10.91.

Example 10
Preparation of 4-{3-[2-(1-(5-chloro-pyridin-2-one)acetyl)-(S)-1,2,3,4-tetrahydro-isoquinolin-3-yl-methyl]-3H-imidazol-4-yl-methyl}-benzonitrile Step A:
Preparation of 5-chloropyridin-2-one -1-acetic acid To a solution of ethyl 5-chloropyridin-2-one -1-acetate (0.5 g, 2.32 mmol) in 5 ml ethanol was added 1 N sodium hydroxide (4.6 ml, 4.6 mmol). After stirring for 1 hr at 25° C. 1 N HCl (4.8 ml, 4.8 mmol) was added. The solvents were removed in vacuo and the resulting solid was dried for 18 hr in vacuo, which obtained the title compound.

Step B:
Preparation of 4-{3-[2-(1-(5-chloro-pyridin-2-one)acetyl)-(S)-1,2,3,4-tetrahydro-isoquinolin-3-yl-methyl]-3H-imidazol-4-yl-methyl}-benzonitrile The same proceedure as described in step D of Example 8 above was used to mix 4-{3-[(S)-1,2,3,4-tetrahydro-isoquinolin-3-yl-methyl]-3H-imidazol-4-yl-methyl}-benzonitrile (0.16 g, 0.487 mmol), 5-chloropyridin-2-one -1-acetic acid (0.12 g, 0.487 mmol), 1-hydroxybenzotriazole (0.075 g, 0.487 mmol), EDC (0.093 g, 0.487 mmol) and N-methylmorpholine (0.2 ml, 1.95 mmol) in 5 ml DMF. The title compound was obtained
FAB mas spectrum m/e 499 (m+1). Analysis calculated for $C_{28}H_{24}ClN_5O_2 \cdot 1.70 H_2O$: C, 63.62; H, 5.22; N, 13.25. Found: C, 63.72; H, 5.16; N, 13.01.

Example 11
Preparation of 2-[1-(5-Chloro-pyridin-2-one)ethyl]-7-methoxy -1,2,3,4-tetrahydro-isoquinoline-3(S)-carboxylic acid {2-[3-(4-cyanobenzyl)-3H-imidazol-4-yl]-ethyl}-amide Following the procedures outlined in Examples 1, 4, and 6 above, the title compound was prepared and obtained as a solid.
FAB mas spectrum m/e 571 (m+1). Analysis calculated for $C_{31}H_{31}ClN_6O_3 \cdot 0.1 H_2O \cdot 1.6 CH_2Cl_2$: C, 59.56; H, 5.03; N, 12.19. Found: C, 59.61; H, 5.38; N, 11.89.

Example 12
In vitro inhibition of ras farnesyl transferase

Assays of farnesyl-protein transferase. Partially purified bovine FPTase and Ras peptides (Ras-CVLS, Ras-CVIM and Ras-CAIL) were prepared as described by Schaber et al., *J. Biol. Chem.* 265:14701–14704 (1990), Pompliano, et al., *Biochemistry* 31:3800 (1992) and Gibbs et al., *PNAS U.S.A.* 86:6630–6634 (1989), respectively. Bovine FPTase was assayed in a volume of 100 ml containing 100 mM N-(2-hydroxy ethyl) piperazine-N'-(2-ethane sulfonic acid) (HEPES), pH 7.4, 5 mM $MgCl_2$, 5 mM dithiothreitol (DTT), 100 mM [$^3$H]-farnesyl diphosphate ([$^3$H]-FPP; 740 CBq/mmol, New England Nuclear), 650 nM Ras-CVLS and 10 mg/ml FPTase at 31° C. for 60 min. Reactions were initiated with FPTase and stopped with 1 ml of 1.0 M HCL in ethanol. Precipitates were collected onto filter-mats using a TomTec Mach II cell harvestor, washed with 100% ethanol, dried and counted in an LKB b-plate counter. The assay was linear with respect to both substrates, FPTase levels and time; less than 10% of the [$^3$H]-FPP was utilized during the reaction period. Purified compounds were dissolved in 100% dimethyl sulfoxide (DMSO) and were diluted 20-fold into the assay. Percentage inhibition is measured by the amount of incorporation of radioactivity in the presence of the test compound when compared to the amount of incorporation in the absence of the test compound.

Human FPTase was prepared as described by Omer et al., *Biochemistry* 32:5167–5176 (1993). Human FPTase activity was assayed as described above with the exception that 0.1% (w/v) polyethylene glycol 20,000, 10 mM $ZnCl_2$ and 100 nM Ras-CVIM were added to the reaction mixture. Reactions were performed for 30 min., stopped with 100 ml of 30% (v/v) trichloroacetic acid (TCA) in ethanol and processed as described above for the bovine enzyme.

The compounds of the instant invention described in the above Examples were tested for inhibitory activity against human FPTase by the assay described above and were found to have $IC_{50}$ of <50 µM.

Example 13

Modified In vitro GGTase inhibition asssay

The modified geranylgeranyl-protein transferase inhibition assay is carried out at room temperature. A typical reaction contains (in a final volume of 50 mL): [$^3$H] geranylgeranyl diphosphate, biotinylated Ras peptide, 50 mM HEPES, pH 7.5, a modulating anion (for example 10 mM glycerophosphate or 5 mM ATP), 5 mM $MgCl_2$, 10 mM $ZnCl_2$, 0.1% PEG (15–20,000), 2 mM dithiothreitol, and geranylgeranyl-protein transferase type I(GGTase). The GGTase-type I enzyme employed in the assay is prepared as described in U.S. Pat. No. 5,470,832, incorporated by reference. The Ras peptide is derived from the K4B-Ras protein and has the following sequence: biotinyl-GKKKKKKSKTKCVIM (single amino acid code) (SEQ.ID.NO.: 1). Reactions are initiated by the addition of GGTase and stopped at timed intervals (typically 15 min) by the addition of 200 mL of a 3 mg/mL suspension of streptavidin SPA beads (Scintillation Proximity Assay beads, Amersham) in 0.2 M sodium phosphate, pH 4, containing 50 mM EDTA, and 0.5% BSA. The quenched reactions are allowed to stand for 2 hours before analysis on a Packard TopCount scintillation counter.

For inhibition studies, assays are run as described above, except inhibitors are prepared as concentrated solutions in 100% dimethyl sulfoxide and then diluted 25-fold into the enzyme assay mixture. $IC_{50}$ values are determined with Ras peptide near KM concentrations. Enzyme and nonsaturating substrate conditions for inhibitor $IC_{50}$ determinations are as follows: 75 pM GGTase-I, 1.6 mM Ras peptide, 100 nM geranylgeranyl diphosphate.

Example 14

Cell-based in vitro ras prenylation assay

The cell lines used in this assay consist of either Rat1 or NIH3T3 cells transformed by either viral H-ras; an N-ras chimeric gene in which the C-terminal hypervariable region of viral-H-ras was substituted with the corresponding region from the N-ras gene; or ras-CVLL, a viral-H-ras mutant in which the C-terminal exon encodes leucine instead of serine, making the encoded protein a substrate for geranylgeranylation by GGTase-I. The assay can also be performed using cell lines transformed with human H-ras, N-ras or K4B-ras. The assay is performed essentially as described in DeClue, J. E. et al., Cancer Research 51:712–717, (1991). Cells in 10 cm dishes at 50–75% confluency are treated with the test compound(s) (final concentration of solvent, methanol or dimethyl sulfoxide, is 0.1%). After 4 hours at 37° C., the cells are labelled in 3 ml methionine-free DMEM supplemented with 10% regular DMEM, 2% fetal bovine serum, 400 mCi[$^{35}$S]methionine (1000 Ci/mmol) and test compound(s). Cells treated with lovastatin, a compound that blocks Ras processing in cells by inhibiting the rate-limiting step in the isoprenoid biosynthetic pathway (Hancock, J. F. et al. *Cell,* 57:1167 (1989); DeClue, J. E. et al. *Cancer Res.,* 51:712 (1991); Sinensky, M. et al. *J. Biol. Chem.,* 265:19937 (1990)), serve as a positive control in this assay. After an additional 20 hours, the cells are lysed in 1 ml lysis buffer (1% NP40/20 mM HEPES, pH 7.5/5 mM $MgCl_2$/1 mM DTT/10 mg/ml aprotinen/2 mg/ml leupeptin/2 mg/ml antipain/0.5 mM PMSF) and the lysates cleared by centrifugation at 100,000×g for 45 min. Alternatively, four hours after the additon of the labelling media, the media is removed, the cells washed, and 3 ml of media containing the same or a different test compound added. Following an additional 16 hour incubation, the lysis is carried out as above. Aliquots of lysates containing equal numbers of acid-precipitable counts are bought to 1 ml with IP buffer (lysis buffer lacking DTT) and immunoprecipitated with the ras-specific monoclonal antibody Y13-259 (Furth, M. E. et al., *J. Virol.* 43:294–304, (1982)). Following a 2 hour antibody incubation at 4° C., 200 ml of a 25% suspension of protein A-Sepharose coated with rabbit anti rat IgG is added for 45 min. The immunoprecipitates are washed four times with IP buffer (20 nM HEPES, pH 7.5/1 mM EDTA/l% Triton X-100.0.5% deoxycholate/0.1%/SDS/0.1 M NaCl) boiled in SDS-PAGE sample buffer and loaded on 13% acrylamide gels. When the dye front reached the bottom, the gel is fixed, soaked in Enlightening, dried and autoradiographed. The intensities of the bands corresponding to prenylated and nonprenylated Ras proteins are compared to determine the percent inhibition of prenyl transfer to protein.

Example 15

Cell-based in vitro anchorage independent growth assay (SALSA)

SALSA (Soft Agar-Like Surrogate Assay) measures the inhibition of anchorage-independent growth by prenyltransferase inhibitors. Only transformed cells are able to grow anchorage-independently in the SALSA format. Additionally, cells growing in the SALSA format grow in clumps, resembling the colonies formed in soft agar. SALSA may been used to measure the growth inhibition by prenyltransferase inhibitors in a variety of transformed cell lines, including Rat1 fibroblasts transformed with viral-H-ras (H-ras/rat1), as well as a panel of human tumor cell lines (HTL's).

SALSA is performed in 96-well plates that are coated with a thin film of the polymer, PolyHEMA (Poly(2-hydroxyethyl methacrylate)), which prevents cells from attaching to the plate. Rat1 fibroblast cells transformed with v-Ha-ras (this cell line has been deposited in the ATCC on Aug. 19, 1997 under the terms of the Budapest convention and has been given a designation of ATCC) CRL 12387 are seeded at 5000 cells/well, grown for 4 hr, then vehicle or half-log dilutions of test compound (in either an 8 or 12 point titration) are added. The cells are then grown for 6 days at 37 degrees, without changing the growth media or adding fresh compound. At day 6, cell growth is assessed via a colorimetric assay that measures the cleavage of the tetrazolium dye, MTT, to an insoluble purple formazan, a reaction dependent upon mitochondrial dehydrogenases. At day 6, the cells are incubated for 4 hr with 0.5 mg/ml MTT, and then SDS is added to 9% w/v to lyse the cells and solubilize the insoluble MTT-formazan. The amount of MTT metabolism is quantitated via spectrophotometric detection at 570 nM. Dose-inhibition curves and $IC_{50}$'s are determined.

Example 16
Construction of SEAP reporter plasmid pDSE100

The SEAP reporter plasmid, pDSE100 was constructed by ligating a restriction fragment containing the SEAP coding sequence into the plasmid pCMV-RE-AKI. The SEAP gene is derived from the plasmid pSEAP2-Basic (Clontech, Palo Alto, Calif.). The plasmid pCMV-RE-AKI was constructed by Deborah Jones (Merck) and contains 5 sequential copies of the 'dyad symmetry response element' cloned upstream of a 'CAT-TATA' sequence derived from the cytomegalovirus immediate early promoter. The plasmid also contains a bovine growth hormone poly-A sequence.

The plasmid, pDSE100 was constructed as follows. A restriction fragment encoding the SEAP coding sequence was cut out of the plasmid pSEAP2-Basic using the restriction enzymes EcoR 1 and HpaI. The ends of the linear DNA fragments were filled in with the Klenow fragment of *E. coli* DNA Polymerase I. The 'blunt ended' DNA containing the SEAP gene was isolated by electrophoresing the digest in an agarose gel and cutting out the 1694 base pair fragment. The vector plasmid pCMV-RE-AKI was linearized with the restriction enzyme Bgl-II and the ends filled in with Klenow DNA Polymerase I. The SEAP DNA fragment was blunt end ligated into the pCMV-RE-AKI vector and the ligation products were transformed into DH5-alpha *E. coli* cells (Gibco-BRL). Transformants were screened for the proper insert and then mapped for restriction fragment orientation. Properly oriented recombinant constructs were sequenced across the cloning junctions to verify the correct sequence. The resulting plasmid contains the SEAP coding sequence downstream of the DSE and CAT-TATA promoter elements and upstream of the BGH poly-A sequence.

Cloning of a Myristylated viral-H-ras expression plasmid
A DNA fragment containing viral-H-ras can be PCRed from plasmid "H-1" (Ellis R. et al. *J. Virol.* 36, 408, 1980) using the following oligos.

Sense strand:
5'TCTCCTCGAGGCCACCATGGGGAGTAGCAAGAGCAAGCCTAA
GGACCCCAGCCAGCGCCGGATGACAGAATACAAGCTTGTGGTG
G 3'. (SEQ. ID. NO.: 2)
Antisense: 5'CACATCTAGATCAGGACAGCACAGACTTGCAGC 3'.
(SEQ. ID. NO.: 3)

A sequence encoding the first 15 aminoacids of the v-src gene, containing a myristylation site, is incorporated into the sense strand oligo. The sense strand oligo also optimizes the 'Kozak' translation initiation sequence immediately 5' to the ATG start site. To prevent prenylation at the viral-ras C-terminus, cysteine 186 would be mutated to a serine by substituting a G residue for a C residue in the C-terminal antisense oligo. The PCR primer oligos introduce an XhoI site at the 5' end and a XbaI site at the 3'end. The XhoI-XbaI fragment can be ligated into the mammalian expression plasmid pCI (Promega) cut with XhoI and XbaI. This results in a plasmid in which the recombinant myr-viral-H-ras gene is constitutively transcribed from the CMV promoter of the pCI vector.

Cloning of a viral-H-ras-CVLL expression plasmid
A viral-H-ras clone with a C-terminal sequence encoding the amino acids CVLL can be cloned from the plasmid "H- I" (Ellis R. et al. J. Virol. 36, 408, 1980) by PCR using the following oligos.

Sense strand:
5'TCTCCTCGAGGCCACCATGACAGAATACAAGCTTGTGGTGG-
3' (SEQ. ID. NO.: 4)
Antisense strand:
5'CACTCTAGACTGGTGTCAGAGCAGCACACACTTGCAGC-3'
(SEQ. ID. NO.: 5)

The sense strand oligo optimizes the 'Kozak' sequence and adds an XhoI site. The antisense strand mutates serine 189 to leucine and adds an XbaI site. The PCR fragment can be trimmed with XhoI and XbaI and ligated into the XhoI-XbaI cut vector pCI (Promega). This results in a plasmid in which the mutated viral-H-ras-CVLL gene is constitutively transcribed from the CMV promoter of the pCI vector.

Cloning of c-H-ras-Leu61 expression plasmid
The human c-H-ras gene can be PCRed from a human cerebral cortex cDNA library (Clontech) using the following oligonucleotide primers.

Sense strand:
5'-GAGAGAATTCGCCACCATGACGGAATATAAGCTGGTGG-3'
(SEQ. ID. NO.: 6)
Antisense strand:
5'-GAGAGTCGACGCGTCAGGAGAGCACACACTTGC-3'
(SEQ. ID. NO.: 7)

The primers will amplify a c-H-ras encoding DNA fragment with the primers contributing an optimized 'Kozak' translation start sequence, an EcoRI site at the N-terminus and a Sal I stite at the C-terminal end. After trimming the ends of the PCR product with EcoRI and Sal I, the c-H-ras fragment can be ligated ligated into an EcoRI -Sal I cut mutagenesis vector pAlter-1 (Promega). Mutation of glutamine-61 to a leucine can be accomplished using the manufacturer's protocols and the following oligonucleotide:

5'-CCGCCGGCCTGGAGGAGTACAG-3' (SEQ.ID.NO.: 8)

After selection and sequencing for the correct nucleotide substitution, the mutated c-H-ras-Leu61 can be excised from the pAlter-1 vector, using EcoRI and Sal I, and be directly ligated into the vector pCI (Promega) which has been digested with EcoRI and Sal I. The new recombinant plasmid will constitutively transcribe c-H-ras-Leu61 from the CMV promoter of the pCI vector.

Cloning of a c-N-ras-Val-12 expression plasmid
The human c-N-ras gene can be PCRed from a human cerebral cortex cDNA library (Clontech) using the following oligonucleotide primers.

Sense strand:
5'-GAGAGAATTCGCCACCATGACTGAGTACAAACTGGTGG-3'
(SEQ. ID. NO.: 9)
Antisense strand:
5'-GAGAGTCGACTTGTTACATCACCACACATGGC-3'
(SEQ. ID. NO.: 10)

The primers will amplify a c-N-ras encoding DNA fragment with the primers contributing an optimized 'Kozak' translation start sequence, an EcoRI site at the N-terminus and a Sal I stite at the C-terminal end. After trimming the ends of the PCR product with EcoRI and Sal I, the c-N-ras fragment can be ligated into an EcoRI -Sal I cut mutagenesis vector pAlter-1 (Promega). Mutation of glycine-12 to a valine can be accomplished using the manufacturer's protocols and the following oligonucleotide:
5'-GTTGGAGCAGTTGGTGTTGGG-3' (SEQ.ID.NO.: 11)
After selection and sequencing for the correct nucleotide substitution, the mutated c-N-ras-Val-12 can be excised from the pAlter-1 vector, using EcoRI and Sal I, and be directly ligated into the vector pCI (Promega) which has been digested with EcoRI and Sal I. The new recombinant plasmid will constitutively transcribe c-N-ras-Val-12 from the CMV promoter of the pCI vector.

Cloning of a c-K-ras-Val-12 expression plasmid

The human c-K-ras gene can be PCRed from a human cerebral cortex cDNA library (Clontech) using the following oligonucleotide primers.

Sense strand:
5'-GAGAGGTACCGCCACCATGACTGAATATAAACTTGTGG-3'
(SEQ. ID. NO.: 12)
Antisense strand:
5'-CTCTGTCGACGTATTTACATAATTACACACTTTGTC-3'
(SEQ. ID. NO.: 13)

The primers will amplify a c-K-ras encoding DNA fragment with the primers contributing an optimized 'Kozak' translation start sequence, a KpnI site at the N-terminus and a Sal I stite at the C-terminal end. After trimming the ends of the PCR product with Kpn I and Sal I, the c-K-ras fragment can be ligated into a KpnI -Sal I cut mutagenesis vector pAlter-1 (Promega). Mutation of cysteine-12 to a valine can be accomplished using the manufacturer's protocols and the following oligonucleotide:
5'-GTAGTTGGAGCTGTTGGCGTAGGC-3' (SEQ.ID.NO.: 14)

After selection and sequencing for the correct nucleotide substitution, the mutated c-K-ras-Val-12 can be excised from the pAlter-1 vector, using KpnI and Sal I, and be directly ligated into the vector pCI (Promega) which has been digested with KpnI and Sal I. The new recombinant plasmid will constitutively transcribe c-K-ras-Val-12 from the CMV promoter of the pCI vector.

SEAP assay

Human C33A cells (human epitheial carcenoma—ATTC collection) are seeded in 10 cm tissue culture plates in DMEM+10% fetal calf serum+1X Pen/Strep+1X glutamine+1X NEAA. Cells are grown at 37° C. in a 5% $CO_2$ atmosphere until they reach 50–80% of confluency.

The transient transfection is performed by the CaPO4 method (Sambrook et al., 1989). Thus, expression plasmids for H-ras, N-ras, K-ras, Myr-ras or H-ras-CVLL are co-precipitated with the DSE-SEAP reporter construct. For 10 cm plates 600 ml of $CaCl_2$ -DNA solution is added dropwise while vortexing to 600 ml of 2X HBS buffer to give 1.2 ml of precipitate solution (see recipes below). This is allowed to sit at room temperature for 20 to 30 minutes. While the precipitate is forming, the media on the C33A cells is replaced with DMEM (minus phenol red; Gibco cat. #31053-028)+0.5% charcoal stripped calf serum+1X (Pen/Strep, Glutamine and nonessential aminoacids). The $CaPO_4$-DNA precipitate is added dropwise to the cells and the plate rocked gently to distribute. DNA uptake is allowed to proceed for 5–6 hrs at 37° C. under a 5% $CO_2$ atmosphere.

Following the DNA incubation period, the cells are washed with PBS and trypsinized with 1 ml of 0.05% trypsin. The 1 ml of trypsinized cells is diluted into 10 ml of phenol red free DMEM+0.2% charcoal stripped calf serum+ 1X (Pen/Strep, Glutamine and NEAA). Transfected cells are plated in a 96 well microtiter plate (100 ml/well) to which drug, diluted in media, has already been added in a volume of 100 ml. The final volume per well is 200 ml with each drug concentration repeated in triplicate over a range of half-log steps.

Incubation of cells and drugs is for 36 hrs at 37° under $CO_2$. At the end of the incubation period, cells are examined microscopically for evidence of cell distress. Next, 100 ml of media containing the secreted alkaline phosphatase is removed from each well and transferred to a microtube array for heat treatment at 65° C. for 1 hr to inactivate endogenous alkaline phosphatases (but not the heat stable secreted phosphatase).

The heat treated media is assayed for alkaline phosphatase by a luminescence assay using the luminescence reagent CSPD® (Tropix, Bedford, Mass.). A volume of 50 ml media is combinRased with 200 ml of CSPD cocktail and incubated for 60 minutes at room temperature. Luminesence is monitored using an ML2200 microplate luminometer (Dynatech). Luminescence reflects the level of activation of the fos reporter construct stimulated by the transiently expressed protein.

DNA-$CaPO_4$ precipitate for 10 cm. plate of cells

| | |
|---|---|
| Ras expression plasmid (1 mg/ml) | 10 ml |
| DSE-SEAP Plasmid (1 mg/ml) | 2 ml |
| Sheared Calf Thymus DNA (1 mg/ml) | 8 ml |
| 2M $CaCl_2$ | 74 ml |
| $dH_2O$ | 506 ml |

2X HBS Buffer
280 mM NaCl
10 mM KCl
1.5 mM $Na_2HPO_4$ $2H_2O$
12 mM dextrose
50 mM HEPES
Final pH=7.05
Luminesence Buffer (26 ml)

| | |
|---|---|
| Assay Buffer | 20 ml |
| Emerald Reagent ™ (Tropix) | 2.5 ml |
| 100 mM homoarginine | 2.5 ml |
| CSPD Reagent ® (Tropix) | 1.0 ml |

Assay Buffer 20 ml
Emerald Reagent™ (Tropix) 2.5 ml
Assay Buffer
Add 0.05 M $Na_2CO_3$ to 0.05 M $NaHCO_3$ to obtain pH 9.5.
Make 1 mM in $MgCl_2$ Example 17

In vivo tumor growth inhibition assay (nude mouse)

In vivo efficacy as an inhibitor of the growth of cancer cells may be confirmed by several protocols well known in the art. Examples of such in vivo efficacy studies are described by N. E. Kohl et al. (*Nature Medicine,* 1:792–797 (1995)) and N. E. Kohl et al. (*Proc. Nat. Acad. Sci. U.S.A.,* 91:9141–9145 (1994)).

Rodent fibroblasts transformed with oncogenically mutated human Ha-ras or Ki-ras ($10^6$ cells/animal in 1 ml of DMEM salts) are injected subcutaneously into the left flank of 8–12 week old female nude mice (Harlan) on day 0. The mice in each oncogene group are randomly assigned to a vehicle, compound or combination treatment group. Animals are dosed subcutaneously starting on day 1 and daily for the duration of the experiment. Alternatively, the farnesyl-protein transferase inhibitor may be administered by a continuous infusion pump. Compound, compound combination or vehicle is delivered in a total volume of 0.1 ml. Tumors are excised and weighed when all of the vehicle-treated animals exhibited lesions of 0.5–1.0 cm in diameter, typically 11–15 days after the cells were injected. The average weight of the tumors in each treatment group for each cell line is calculated.

What is claimed is:

1. A compound which inhibits farnesyl-protein transferase of the formula A:

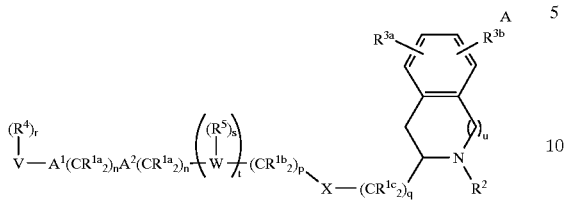

wherein:

$R^{1a}$, $R^{1b}$ and $R^{1c}$ are independently selected from:
  a) hydrogen,
  b) unsubstituted or substituted aryl, unsubstituted or substituted heterocycle, $C_3-C_{10}$ cycloalkyl, $C_2-C_6$ alkenyl, $C_2-C_6$ alkynyl, $R^8O-$, $R^9S(O)_m-$, $R^8C(O)NR^8-$, CN, $NO_2$, $(R^8)_2N-C(NR^8)-$, $R^8C(O)-$, $R^8OC(O)-$, $N_3$, $-N(R^8)_2$, or $R^9OC(O)NR^8-$,
  c) $C_1-C_6$ alkyl unsubstituted or substituted by unsubstituted or substituted aryl, heterocyclic, $C_3-C_{10}$ cycloalkyl, $C_2-C_6$ alkenyl, $C_2-C_6$ alkynyl, $R^8O-$, $R^9S(O)_m-$, $R^8C(O)NR^8-$, CN, $(R^8)_2N-C(NR^8)-$, $R^8C(O)-$, $R^8OC(O)-$, $N_3$, $-N(R^8)_2$, or $R^9OC(O)-NR^8-$;

$R^2$ is selected from: H; unsubstituted or substituted $C_{1-8}$ alkyl, unsubstituted or substituted $C_{2-8}$ alkenyl, unsubstituted or substituted aryl, unsubstituted or substituted heterocycle, $(CH_2)_pR^{11}$,

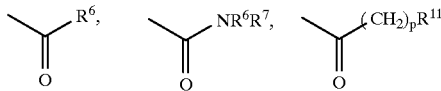

and $-S(O)_2R^6$, wherein the substituted group is substituted with one or more of:
  1) aryl or heterocycle, unsubstituted or substituted with one or two groups selected from:
    a) $C_{1-4}$ alkyl,
    b) $(CH_2)_pOR^6$,
    c) $(CH_2)_pNR^6R^7$,
    d) halogen,
    e) $C_{1-4}$ perfluoroalkyl,
  2) $C_{3-6}$ cycloalkyl,
  3) $OR^6$,
  4) $SR^6$, $S(O)R^6$, $SO_2R^6$,

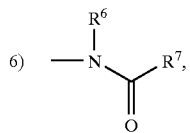

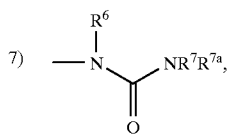

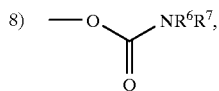

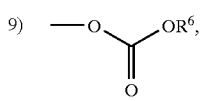

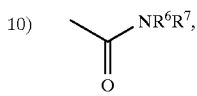

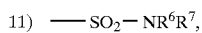

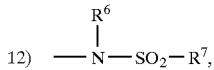

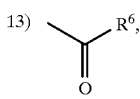

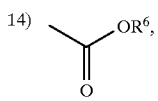

15) $C_{1-8}$ alkyl, or
  16) $C_{1-8}$ perfluoroalkyl;

$R^{3a}$ and $R^{3b}$ are independently selected from:
  a) hydrogen,
  b) unsubstituted or substituted aryl, unsubstituted or substituted heterocycle, unsubstituted or substituted $C_3-C_{10}$ cycloalkyl, unsubstituted or substituted $C_2-C_6$ alkenyl, $C_2-C_6$ alkynyl, halogen, $C_1-C_6$ perfluoroalkyl, $R^8O-$, $R^9S(O)_m-$, $R^8C(O)NR^8-$, $(R^8)_2NC(O)-$, $R^9C(O)O-$, $R^8_2N-C(NR^8)-$, CN, $NO_2$, $R^8C(O)-$, $N_3$, $-N(R^8)_2$, or $R^9OC(O)NR^8-$,
  c) unsubstituted $C_1-C_6$ alkyl,
  d) substituted $C_1-C_6$ alkyl wherein the substituent on the substituted $C_1-C_6$ alkyl is selected from unsubstituted or substituted aryl, unsubstituted or substituted heterocyclic, $C_3-C_{10}$ cycloalkyl, $C_2-C_6$ alkenyl, $C_2-C_6$ alkynyl, $R^8O-$, $R^9S(O)_m-$, $R^8C(O)NR^8-$, $(R^8)_2NC(O)-$, $R^8_2N-C(NR^8)-$, CN, $R^8C(O)-$, $N_3$, $-N(R^8)_2$, and $R^9OC(O)-NR^8-$;

$R^4$ is independently selected from:
  a) hydrogen,
  b) unsubstituted or substituted aryl, unsubstituted or substituted heterocycle, $C_3-C_{10}$ cycloalkyl, $C_2-C_6$ alkenyl, $C_2-C_6$ alkynyl, perfluoroalkyl, F, Cl, Br, $R^8O-$, $R^9S(O)_m-$, $R^8C(O)NR^8-$, CN, $NO_2$, $R^8_2N-C(NR^8)-$, $R^8C(O)-$, $R^8OC(O)-$, $N_3$, $-N(R^8)_2$, or $R^9OC(O)NR^8-$, and
  c) $C_1-C_6$ alkyl unsubstituted or substituted by aryl, heterocycle, $C_3-C_{10}$ cycloalkyl, $C_2-C_6$ alkenyl, $C_2-C_6$ alkynyl, perfluoroalkyl, F, Cl, Br, $R^8O-$, $R^9S(O)_m-$, $R^8C(O)NH-$, CN, $H_2N-C(NH)-$, $R^8C(O)-$, $R^8OC(O)-$, $N_3$, $-N(R^8)_2$, or $R^8OC(O)NH-$;

$R^5$ is independently selected from:
  a) hydrogen,
  b) $C_2-C_6$ alkenyl, $C_2-C_6$ alkynyl, $C_3-C_6$ cycloalkyl, perfluoroalkyl, F, Cl, Br, $R^8O-$, $R^9S(O)_m-$, $R^8C(O)NR^8-$, CN, $NO_2$, $(R^8)_2N-C-(NR^8)-$, $R^8C(O)-$, $R^8OC(O)-$, $N_3$, $-N(R^8)_2$, or $R^9OC(O)NR^8-$, and
  c) $C_1-C_6$ alkyl, unsubstituted or substituted by perfluoroalkyl, F, Cl, Br, $R^8O-$, $R^9S(O)_m-$, $R^8C(O)NR^8-$, CN, $(R^8)_2N-C(NR^8)-$, $R^8C(O)-$, $R^8OC(O)-$, $N_3$, $-N(R^8)_2$, or $R^9OC(O)NR^8-$; $R^6$, $R^7$ and $R^{7a}$ are independently selected from: H; $C_{1-4}$ alkyl, $C_{3-6}$ cycloalkyl, heterocycle, aryl, $C_{1-4}$ perfluoroalkyl, unsubstituted or substituted with one or two substituents selected from:
    a) $C_{1-4}$ alkoxy,
    b) substituted or unsubstituted aryl or substituted or unsubstituted heterocycle,
    c) halogen,
    d) HO,
    e) 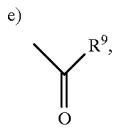
    f) 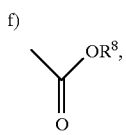
    g) $-S(O)_mR^9$ or
    h) $N(R^8)_2$; or $R^6$ and $R^7$ may be joined in a ring;
$R^7$ and $R^{7a}$ may be joined in a ring;
$R^8$ is independently selected from hydrogen, $C_1-C_6$ alkyl, benzyl, 2,2,2-trifluoroethyl and aryl;
$R^9$ is independently selected from $C_1-C_6$ alkyl and aryl;
$R^{10}$ is selected from: H; $R^8C(O)-$; $R^9S(O)_m-$; unsubstituted or substituted $C_{14}$ alkyl, unsubstituted or substituted $C_{3-6}$ cycloalkyl, unsubstituted or substituted heterocycle, unsubstituted or substituted aryl, substituted aroyl, unsubstituted or substituted heteroaroyl, substituted arylsulfonyl, unsubstituted or substituted heteroarylsulfonyl, wherein the substituted group is substituted with one or two substituents selected from:
    a) $C_{1-4}$ alkoxy,
    b) aryl or heterocycle,
    c) halogen,
    d) HO,
    e) 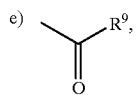
    f) 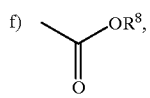
    g) $-S(O)_mR^9$
    h) $N(R^8)_2$, and
    i) $C_{3-6}$ cycloalkyl;

$R^{11}$ is selected from: unsubstituted or substituted aryl, unsubstituted or substituted heterocycle, unsubstituted or substituted pyridinone;

$A^1$ and $A^2$ are independently selected from: a bond, $-CH=CH-$, $-C\equiv C-$, $-C(O)-$, $-C(O)NR^8-$, $-NR^8C(O)-$, O, $-N(R^8)-$, $-S(O)_2N(R^8)-$, $-N(R^8)S(O)_2-$, or $S(O)_m$;

V is selected from:
  a) heterocycle,
  b) aryl,
  c) $C_1-C_{20}$ alkyl wherein from 0 to 4 carbon atoms are replaced with a heteroatom selected from O, S, and N, and
  d) $C_2-C_{20}$ alkenyl, W is a heterocycle;
X is a bond, $-C(=O)NR^{10}-$, $-NR^{10}C(=O)-$, $-S(O)_m-$, $-NR^{10}-$, O or $-C(=O)-$;
m is 0, 1 or 2;
n is 0, 1, 2, 3 or 4;
p is 0, 1, 2, 3 or 4;
q is 0, 1, 2, 3 or 4, provided that q is not 0 when X is $-C(=O)NR^{10}-$, $-S(O)_m-$, $-NR^{10}-$ or O;
r is 0 to 5;
s is 1 or 2;
t is 1; and
u is 1 or 2;

or an optical isomer or a pharmaceutically acceptable salt thereof.

2. The compound according to claim 1 which inhibits farnesyl-protein transferase of the formula A:

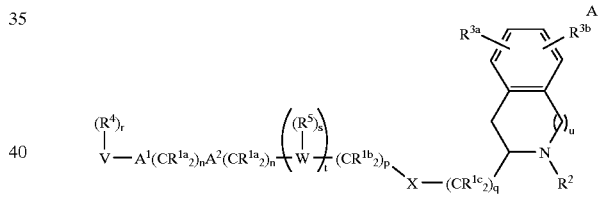

wherein:

$R^{1a}$ and $R^{1c}$ are independently selected from: hydrogen, $C_3-C_{10}$ cycloalkyl, $R^8O-$, $-N(R^8)_2$, F or $C_1-C6$ alkyl;

$R^{1b}$ is independently selected from:
  a) hydrogen,
  b) unsubstituted or substituted aryl, unsubstituted or substituted heterocycle, $C_3-C_6$ cycloalkyl, $R^8O-$, $-N(R^8)_2$ or $C_2-C_6$ alkenyl,
  c) $C_1-C_6$ alkyl unsubstituted or substituted by unsubstituted or substituted aryl, heterocycle, $C_3-C_6$ cycloalkyl, $C_2-C_6$ alkenyl, $R^8O-$, or $-N(R^8)_2$;

$R^2$ is selected from:
  a) $C_{1-8}$ alkyl, unsubstituted or substituted with one or more of:
    1) aryl or heterocycle, unsubstituted or substituted with:
       i) $C_{1-4}$ alkyl,
       ii) $(CH_2)_pOR^6$,
       iii) $(CH_2)_pNR^6R^7$,
       iv) halogen,
       v) $C_{1-4}$ perfluoroalkyl,
    2) $OR^6$, 3) SR$^6$, SO$_2$R$^6$, or 4) 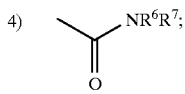

b) 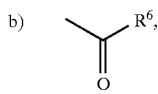

c) aryl, unsubstituted or substituted with one or more of:
1) C$_{1-8}$ alkyl,
2) C$_{1-8}$ perfluoroalkyl,
3) OR$^6$,
4) SR$^6$, SO$_2$R$^6$, or 5) 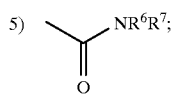

d) 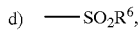—SO$_2$R$^6$, e) 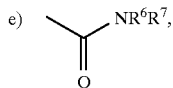

f) (CH$_2$)$_p$R11, and g) 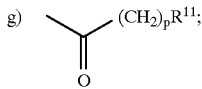

R$^3$a and R3b are independently selected from:
a) hydrogen,
b) unsubstituted or substituted aryl, unsubstituted or substituted heterocycle, unsubstituted or substituted C$_3$–C$_{10}$ cycloalkyl, unsubstituted or substituted C$_2$–C$_6$ alkenyl, C$_2$–C$_6$ alkynyl, halogen, C$_1$–C$_6$ perfluoroalkyl, R$^8$O—, R$^9$S(O)$_m$—, R$^8$C(O)NR$^8$-, (R$^8$)$_2$NC(O)—, R$^9$C(O)O—, R$^8{}_2$N—C(NR$^8$)—, CN, NO$_2$, R$^8$C(O)—, N$_3$, —N(R$^8$)$_2$, or R$^9$OC(O)NR$^8$-,
c) unsubstituted C$_1$–C$_6$ alkyl,
d) substituted C$_1$–C$_6$ alkyl wherein the substituent on the substituted C$_1$–C$_6$ alkyl is selected from unsubstituted or substituted aryl, unsubstituted or substituted heterocyclic, C$_3$–C$_{10}$ cycloalkyl, C$_2$–C$_6$ alkenyl, C$_2$–C$_6$ alkynyl, R$^8$O—, R$^9$S(O)$_m$—, R$^8$C(O)NR$^8$-, (R$^8$)$_2$NC(O)—, R$^8{}_2$N—C(NR$^8$)—, CN, R$^8$C(O)—, N$_3$, —N(R$^8$)$_2$, and R$^9$OC(O)—NR$^8$-;

R$^4$ is independently selected from:
a) hydrogen,
b) C$_1$–C$_6$ alkyl, C$_2$–C$_6$ alkenyl, C$_2$–C$_6$ alkynyl, C$_1$–C$_6$ perfluoroalkyl, F, Cl, R$^8$O—, R$^8$C(O)NR$^8$-, CN, NO$_2$, (R$^8$)$_2$N—C(NR$^8$)—, R$^8$C(O)—, R$^8$OC(O)—, —N(R$^8$)$_2$, or R$^9$OC(O)NR$^8$-, and
c) C$_1$–C$_6$ alkyl substituted by C$_1$–C$_6$ perfluoroalkyl, R$^8$O—, R$^8$C(O)NR$^8$-, (R$^8$)$_2$N—C(NR$^8$)—, R$^8$C(O)—, R$^8$OC(O)—, —N(R$^8$)$_2$, or R$^9$OC(O)NR$^8$-;

R$^5$ is selected from:
a) hydrogen,
b) C$_2$–C$_6$ alkenyl, C$_2$–C$_6$ alkynyl, C$_3$–C$_6$ cycloalkyl, C$_1$–C$_6$ perfluoroalkyl, F, Cl, R$^8$O—, R$^9$S(O)$_m$—, R$^8$C(O)NR$^8$-, CN, NO$_2$, (R$^8$)$_2$N—C(NR$^8$)—, R$^8$C(O)—, R$^8$OC(O)—, —N(R$^8$)$_2$, or R$^9$OC(O)NR$^8$-, and
c) C$_1$–C$_6$ alkyl unsubstituted or substituted by C$_1$–C$_6$ perfluoroalkyl, F, Cl, R$^8$O—, R$^9$S(O)$_m$—, R$^8$C(O)NR$^8$-, CN, (R$^8$)$_2$N—C(NR$^8$)—, R$^8$C(O)—, R$^8$OC(O)—, —N(R$^8$)$_2$, or R$^9$OC(O)NR$^8$-;

R$^6$, R$^7$ and R$^{7a}$ are independently selected from:
H; C$_{1-4}$ alkyl, C$_{3-6}$ cycloalkyl, aryl, heterocycle, unsubstituted or substituted with:
a) C$_{1-4}$ alkoxy,
b) halogen, or
c) substituted or unsubstituted aryl or substituted or unsubstituted heterocycle, R$^8$ is independently selected from hydrogen, C$_1$–C$_6$ alkyl, benzyl, 2,2,2-trifluoroethyl and aryl;

R$^9$ is independently selected from C$_1$–C$_6$ alkyl and aryl;

R$^{10}$ is selected from: H; R$^8$C(O)—; R$^9$S(O)$_m$—; unsubstituted or substituted C$_{1-4}$ alkyl, unsubstituted or substituted C$_{3-6}$ cycloalkyl, unsubstituted or substituted heterocycle, unsubstituted or substituted aryl, substituted aroyl, unsubstituted or substituted heteroaroyl, substituted arylsulfonyl, unsubstituted or substituted heteroarylsulfonyl, wherein the substituted group is substituted with one or two substituents selected from:
a) C$_{1-4}$ alkoxy,
b) aryl or heterocycle,
c) halogen,
d) HO, e) 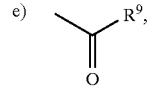

f) 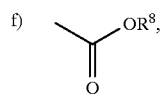

g) —S(O)$_m$R$^9$
h) N(R$^8$)$_2$, and
i) C$_{3-6}$ cycloalkyl;

R$^{11}$ is selected from: unsubstituted or substituted aryl, unsubstituted or substituted heterocycle, unsubstituted or substituted pyridinone;

A$^1$ and A$^2$ are independently selected from: a bond, —CH=CH—, —C≡C—, —C(O)—, —C(O)NR$^8$-, O, —N(R$^8$)—, or S(O)$_m$;

V is selected from:
a) heterocycle selected from pyrrolidinyl, imidazolyl, pyridinyl, thiazolyl, 2-oxopiperidinyl, indolyl, quinolinyl, isoquinolinyl, and thienyl, and
b) aryl;

W is a heterocycle selected from pyrrolidinyl, imidazolyl, pyridinyl, thiazolyl, pyridonyl, 2-oxopiperidinyl, indolyl, quinolinyl, or isoquinolinyl;

X is a bond, —C(=O)NR$^{10}$-, —NR$^{10}$C(=O)—, —S(O)$_m$— or —NR$^{10}$-;

m is 0, 1 or 2;
n is 0, 1, 2, 3 or 4;
p is 1, 2 or 3;
q is 0, 1, 2, 3 or 4, provided that q is not 0 when X is —C(=O)NR$^{10}$-, —S(O)$_m$— or —NR$^{10}$-;
r is 0 to 5, provided that r is 0 when V is hydrogen;
s is 1 or 2;
t is 1; and
u is 1 or 2;

or an optical isomer or a pharmaceutically acceptable salt thereof.

3. The compound according to claim 1 which inhibits farnesyl-protein transferase of the formula B:

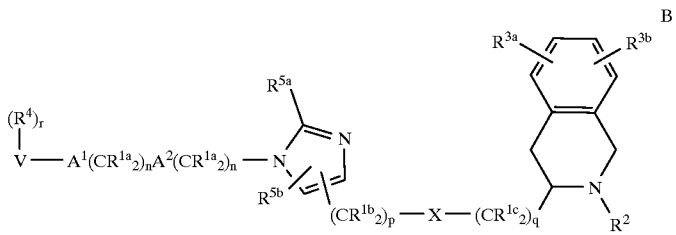

wherein:

$R^{1a}$ and $R^{1c}$ are independently selected from: hydrogen, $C_3$–$C_{10}$ cycloalkyl, $R^8O$—, —$N(R^8)_2$, F or $C_1$–$C_6$ alkyl;

$R^{1b}$ is independently selected from:
a) hydrogen,
b) aryl, heterocycle, $C_3$–$C_{10}$ cycloalkyl, $R^8O$—, —$N(R^8)_2$, F or $C_2$–$C_6$ alkenyl,
c) unsubstituted or substituted $C_1$–$C_6$ alkyl wherein the substituent on the substituted $C_1$–$C_6$ alkyl is selected from unsubstituted or substituted aryl, heterocycle, $C_3$–$C_{10}$ cycloalkyl, $C_2$–$C_6$ alkenyl, $R^8O$— and —$N(R^8)_2$;

$R^2$ is selected from: H; unsubstituted or substituted $C_{1-8}$ alkyl, unsubstituted or substituted $C_{2-8}$ alkenyl, unsubstituted or substituted aryl, unsubstituted or substituted heterocycle, $(CH_2)_p R^{11}$,

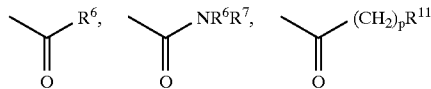

and —$S(O)_2 R^6$, wherein the substituted group is substituted with one or more of:

1) aryl or heterocycle, unsubstituted or substituted with one or two groups selected from:
a) $C_{1-4}$ alkyl,
b) $(CH_2)_p OR^6$,
c) $(CH_2)_p NR^6R^7$,
d) halogen,
e) $C_{1-4}$ perfluoroalkyl,
2) $C_{3-6}$ cycloalkyl,
3) $OR^6$,
4) $SR^6$, $S(O)R^6$, $SO_2R^6$,
5) —$NR^6R^7$, 6) 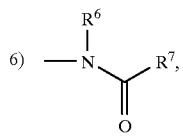

7) 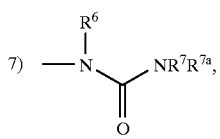

8) 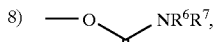

9) 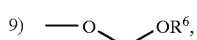

10) 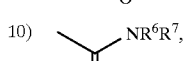

11) —$SO_2$—$NR^6R^7$,

12) 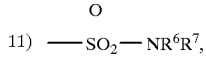

13) 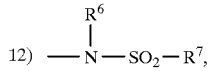

14) 

15) $C_{1-8}$ alkyl, or
16) $C_{1-8}$ perfluoroalkyl;

$R^{3a}$ and $R^{3b}$ are independently selected from:
a) hydrogen,
b) unsubstituted or substituted aryl, unsubstituted or substituted heterocycle, unsubstituted or substituted $C_3$–$C_{10}$ cycloalkyl, unsubstituted or substituted $C_2$–$C_6$ alkenyl, $C_2$–$C_6$ alkynyl, halogen, $C_1$–$C_6$ perfluoroalkyl, $R^8O$—, $R^9S(O)_m$—, $R^8C(O)NR^8$-, $(R^8)_2NC(O)$—, $R^9C(O)O$—, $R^8_2N$—$C(NR^8)$—, CN, NO$_2$, $R^8C(O)$—, N$_3$, —$N(R^8)_2$, or $R^9OC(O)NR^8$-,
c) unsubstituted $C_1$–$C_6$ alkyl,
d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^8O$—, $R^9S(O)_m$—, $R^8C(O)NR^8$-, $(R^8)_2NC(O)$—, $R^8_2N$—$C(NR^8)$—, CN, $R^8C(O)$—, N$_3$, —$N(R^8)_2$, and $R^9OC(O)$—$NR^8$-;

$R^4$ is independently selected from:
a) hydrogen,
b) aryl, substituted aryl, heterocycle, substituted heterocycle, $C_1$–$C_6$ alkyl, $C_2$–$C_6$ alkenyl, $C_2$–$C_6$ alkynyl, $C_1$–$C_6$ perfluoroalkyl, F, Cl, $R^8O$—, $R^8C(O)NR^8$-, CN, NO$_2$, $(R^8)_2N$—$C(NR^8)$—, $R^8C(O)$—, —$N(R^8)_2$, or $R^9OC(O)NR^8$-, and c) $C_1$–$C_6$ alkyl substituted by $C_1$–$C_6$ perfluoroalkyl, $R^8O$—, $R^8C(O)NR^8$-, $(R^8)_2N$—$C(NR^8)$—, $R^8C(O)$—, —$N(R^8)_2$, or $R^9OC(O)NR^8$-;

$R^{5a}$ and $R^{5b}$ are independently hydrogen, $C_1$–$C_6$ alkyl, cyclopropyl, trifluoromethyl and halogen;

$R^6$, $R^7$ and $R^{7a}$ are independently selected from:
 H; $C_{1-4}$ alkyl, $C_{3-6}$ cycloalkyl, aryl, heterocycle, unsubstituted or substituted with:
  a) $C_{1-4}$ alkoxy,
  b) halogen, or
  c) substituted or unsubstituted aryl or substituted or unsubstituted heterocycle, $R^8$ is independently selected from hydrogen, $C_1$–$C_6$ alkyl, 2,2,2-trifluoroethyl, benzyl and aryl;

$R^9$ is independently selected from $C_1$–$C_6$ alkyl and aryl;

$R^{10}$ is selected from: H; $R^8C(O)$—; $R^9S(O)_m$—; unsubstituted or substituted $C_{1-4}$ alkyl, unsubstituted or substituted $C_{3-6}$ cycloalkyl, unsubstituted or substituted heterocycle, unsubstituted or substituted aryl, substituted aroyl, unsubstituted or substituted heteroaroyl, substituted arylsulfonyl, unsubstituted or substituted heteroarylsulfonyl, wherein the substituted group is substituted with one or two substituents selected from:
  a) $C_{1-4}$ alkoxy,
  b) aryl or heterocycle,
  c) halogen,
  d) HO,
  e) 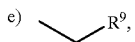
  f) 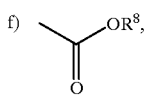
  g) —$S(O)_mR^9$,
  h) $N(R^8)_2$, and
  i) $C_{3-6}$ cycloalkyl;

$R^{11}$ is selected from: unsubstituted or substituted aryl, unsubstituted or substituted heterocycle, unsubstituted or substituted pyridinone, wherein the substituents on the cyclic group are selected from: halogen, —OH, and —O($C_1$–$C_6$ alkyl);

$A^1$ and $A^2$ are independently selected from: a bond, —CH═CH—, —C≡C—, —C(O)—, —C(O)NR$^8$-, O, —N(R$^8$)—, or $S(O)_m$;

V is selected from:
  a) heterocycle selected from pyrrolidinyl, imidazolyl, imidazolinyl, pyridinyl, thiazolyl, 2-oxopiperidinyl, oxazolyl, indolyl, quinolinyl, isoquinolinyl, triazolyl and thienyl,
  b) aryl,
  c) $C_1$–$C_{20}$ alkyl wherein from 0 to 4 carbon atoms are replaced with a heteroatom selected from O, S, and N, and
  d) $C_2$–$C_{20}$ alkenyl, X is a bond, —C(═O)NR$^{10}$-, —NR$^{10}$C(═O)—, —S(O)$_m$— or —NR$^{10}$-;

m is 0, 1 or 2;
n is 0, 1, 2, 3 or 4;
p is 0, 1, 2, 3 or 4;
q is 0, 1, 2, 3 or 4, provided that q is not 0 when X is —C(═O)NR$^{10}$-, —S(O)$_m$— or —NR$^{10}$-; and
r is 0 to 5;

or an optical isomer or pharmaceutically acceptable salt thereof.

4. The compound according to claim 1 which inhibits farnesyl-protein transferase of the formula C:

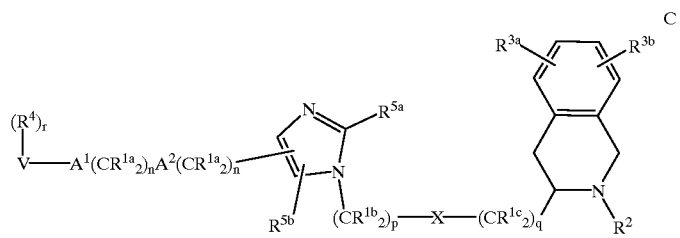

wherein:

$R^{1a}$ and $R^{1c}$ are independently selected from: hydrogen, $C_3$–$C_{10}$ cycloalkyl, $R^8O$—, —$N(R^8)_2$, F or $C_1$–$C_6$ alkyl;

$R^{1b}$ is independently selected from:
 a) hydrogen,
 b) aryl, heterocycle, $C_3$–$C_{10}$ cycloalkyl, $R^8O$—, —$N(R^8)_2$, F or $C_2$–$C_6$ alkenyl,
 c) unsubstituted or substituted $C_1$–$C_6$ alkyl wherein the substituent on the substituted $C_1$–$C_6$ alkyl is selected from unsubstituted or substituted aryl, heterocycle, $C_3$–$C_{10}$ cycloalkyl, $C_2$–$C_6$ alkenyl, $R^8O$— and —$N(R^8)_2$;

$R^2$ is selected from: H; unsubstituted or substituted $C_{1-8}$ alkyl, unsubstituted or substituted $C_{2-8}$ alkenyl, unsubstituted or substituted aryl, unsubstituted or substituted heterocycle, $(CH_2)_pR^{11}$,

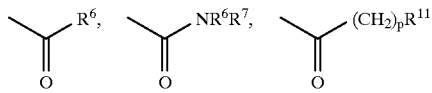

and —$S(O)_2R^6$, wherein the substituted group is substituted with one or more of:
 1) aryl or heterocycle, unsubstituted or substituted with one or two groups selected from:
  a) $C_{1-4}$ alkyl,
  b) $(CH_2)_pOR^6$,
  c) $(CH_2)_pNR^6R^7$,
  d) halogen,
  e) $C_{1-4}$ perfluoroalkyl,
 2) $C_{3-6}$ cycloalkyl,
 3) $OR^6$,
 4) $SR^6$, $S(O)R^6$, $SO_2R^6$,

5) —NR$^6$R$^7$,

6) 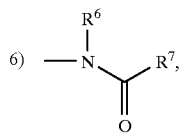

7) 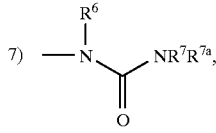

8) 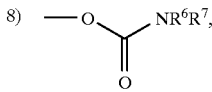

9) 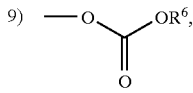

10) 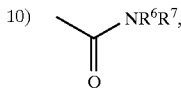

11) —SO$_2$—NR$^6$R$^7$,

12) 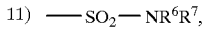

13) 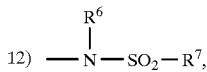

14) 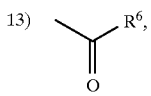

15) C$_{1-8}$ alkyl, or
16) C$_{1-8}$ perfluoroalkyl;

R$^{3a}$ and R$^{3b}$ are independently selected from:
  a) hydrogen,
  b) unsubstituted or substituted aryl, unsubstituted or substituted heterocycle, unsubstituted or substituted C$_3$–C$_{10}$ cycloalkyl, unsubstituted or substituted C$_2$–C$_6$ alkenyl, C$_2$–C$_6$ alkynyl, halogen, C$_1$–C$_6$ perfluoroalkyl, R$^8$O—, R$^9$S(O)$_m$—, R$^8$C(O)NR$^8$-, (R$^8$)$_2$NC(O)—, R$^9$C(O)O—, R$^8_2$N—C(NR$^8$)—, CN, NO$_2$, R$^8$C(O)—, N$_3$, —N(R$^8$)$_2$, or R$^9$OC(O)NR$^8$-,
  c) unsubstituted C$_1$–C$_6$ alkyl,
  d) substituted C$_1$–C$_6$ alkyl wherein the substituent on the substituted C$_1$–C$_6$ alkyl is selected from unsubstituted or substituted aryl, unsubstituted or substituted heterocyclic, C$_3$–C$_{10}$ cycloalkyl, C$_2$–C$_6$ alkenyl, C$_2$–C$_6$ alkynyl, R$^8$O—, R$^9$S(O)$_m$—, R$^8$C(O)NR$^8$-, (R$^8$)$_2$NC(O)—, R$^8_2$N—C(NR$^8$)—, CN, R$^8$C(O)—, N$_3$, —N(R$^8$)$_2$, and R$^9$OC(O)—NR$^8$-;

R$^4$ is independently selected from:
  a) hydrogen,
  b) aryl, substituted aryl, heterocycle, substituted heterocycle, C$_1$–C$_6$ alkyl, C$_2$–C$_6$ alkenyl, C$_2$–C$_6$ alkynyl, C$_1$–C$_6$ perfluoroalkyl, F, Cl, R$^8$O—, R$^8$C(O)NR$^8$-, CN, NO$_2$, (R$^8$)$_2$N—C(NR$^8$)—, R$^8$C(O)—, —N(R$^8$)$_2$, or R$^9$OC(O)NR$^8$-, and
  c) C$_1$–C$_6$ alkyl substituted by C$_1$–C$_6$ perfluoroalkyl, R$^8$O—, R8C(O)NR$^8$-, (R$^8$)$_2$N—C(NR$^8$)—, R$^8$C(O)—, —N(R$^8$)$_2$, or R$^9$OC(O)NR$^8$-;

R$^{5a}$ and R$^{5b}$ are independently hydrogen, C$_1$–C$_6$ alkyl, cyclopropyl, trifluoromethyl and halogen;

R$^6$, R$^7$ and R$^{7a}$ are independently selected from:
  H; C$_{1-4}$ alkyl, C$_{3-6}$ cycloalkyl, aryl, heterocycle, unsubstituted or substituted with:
    a) C$_{1-4}$ alkoxy,
    b) halogen, or
    c) substituted or unsubstituted aryl or substituted or unsubstituted heterocycle, R$^8$ is independently selected from hydrogen, C$_1$–C$_6$ alkyl, 2,2,2-trifluoroethyl, benzyl and aryl;

R$^9$ is independently selected from C$_1$–C$_6$ alkyl and aryl;

R$^{10}$ is selected from: H; R$^8$C(O)—; R$^9$S(O)$_m$—; unsubstituted or substituted C$_{1-4}$ alkyl, unsubstituted or substituted C$_{3-6}$ cycloalkyl, unsubstituted or substituted heterocycle, unsubstituted or substituted aryl, substituted aroyl, unsubstituted or substituted heteroaroyl, substituted arylsulfonyl, unsubstituted or substituted heteroarylsulfonyl, wherein the substituted group is substituted with one or two substituents selected from:
  a) C$_{1-4}$ alkoxy,
  b) aryl or heterocycle,
  c) halogen,
  d) HO,
  e) 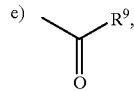
  f) 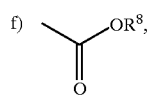
  g) —S(O)$_m$R$^9$
  h) N(R$^8$)$_2$, and
  i) C$_{3-6}$ cycloalkyl;

R$^{11}$ is selected from: unsubstituted or substituted aryl, unsubstituted or substituted heterocycle, unsubstituted or substituted pyridinone, wherein the substituents on the cyclic group are selected from: halogen, —OH and —O(C$_{1-6}$ alkyl);

A$^1$ and A$^2$ are independently selected from: a bond, —CH=CH—, —C≡C—, —C(O)—, —C(O)NR$^8$-, O, —N(R$^8$)—, or S(O)$_m$;

V is selected from:
  a) heterocycle selected from pyrrolidinyl, imidazolyl, imidazolinyl, pyridinyl, thiazolyl, 2-oxopiperidinyl, oxazolyl, indolyl, quinolinyl, isoquinolinyl, triazolyl and thienyl,
  b) aryl,
  c) C$_1$–C$_{20}$ alkyl wherein from 0 to 4 carbon atoms are replaced with a heteroatom selected from O, S, and N, and
  d) C$_2$–C$_{20}$ alkenyl, X is a bond, —C(=O)NR$^{10}$-, —NR$^{10}$C(=O)—, —S(O)$_m$— or —NR$^{10}$-;

m is 0, 1 or 2;
n is 0, 1, 2, 3 or 4;
p is 0, 1, 2, 3 or 4, provided that p is not 0 if X is a bond, —NR$^8$- or O;
q is 0, 1, 2, 3 or 4, provided that q is not 0 when X is —C(=O)NR$^{10}$-, —S(O)$_m$— or —NR$^{10}$-; and
r is 0 to 5;

or an optical isomer or pharmaceutically acceptable salt thereof.

5. The compound according to claim 3 which inhibits farnesyl-protein transferase of the formula D:

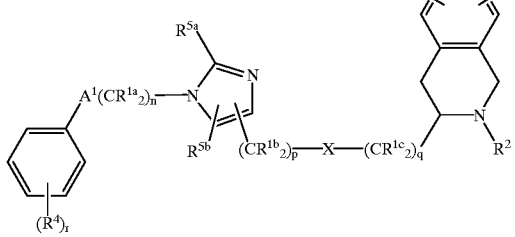

wherein:

$R^{1a}$ and $R^{1c}$ are independently selected from: hydrogen, $C_3$–$C_{10}$ cycloalkyl or $C_1$–$C_6$ alkyl;

$R^{1b}$ is independently selected from:
 a) hydrogen,
 b) aryl, heterocycle, $C_3$–$C_{10}$ cycloalkyl, $R^8O$—, —$N(R^8)_2$, F or $C_2$–$C_6$ alkenyl,
 c) $C_1$–$C_6$ alkyl unsubstituted or substituted by aryl, heterocycle, $C_3$–$C_{10}$ cycloalkyl, $C_2$–$C_6$ alkenyl, $R^8O$—, or —$N(R^8)_2$;

$R^2$ is selected from: H; unsubstituted or substituted $C_{1-8}$ alkyl, unsubstituted or substituted aryl, $(CH_2)_pR^{11}$,

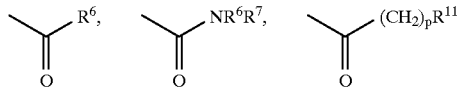

and —$S(O)_2R^6$, wherein the substituted group is substituted with one or more of:
 1) aryl or heterocycle, unsubstituted or substituted with one or two groups selected from:
  a) $C_{1-4}$ alkyl,
  b) $(CH_2)_pOR^6$,
  c) $(CH_2)_pNR^6R^7$,
  d) halogen,
  e) $C_{1-4}$ perfluoroalkyl,
 2) $C_{3-6}$ cycloalkyl,
 3) $OR^6$,
 4) $SR^6$, $S(O)R^6$, $SO_2R^6$,
 5) —N $R^6R^7$ 6) 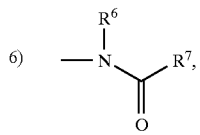

7) 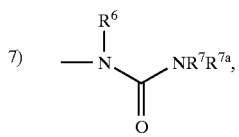

8) 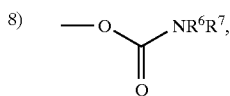

9) 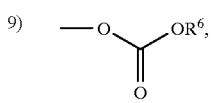

10) 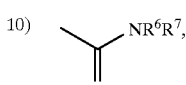

11) —$SO_2$—$NR^6R^7$,

12) 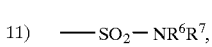

13) 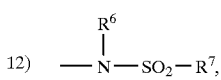

14) 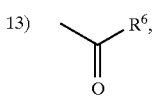

15) $C_{1-8}$ alkyl, or
 16) $C_{1-8}$ perfluoroalkyl;

$R^{3a}$ and $R^{3b}$ are independently selected from:
 a) hydrogen,
 b) unsubstituted or substituted aryl, unsubstituted or substituted heterocycle, unsubstituted or substituted $C_3$–$C_{10}$ cycloalkyl, unsubstituted or substituted $C_2$–$C_6$ alkenyl, $C_2$–$C_6$ alkynyl, halogen, $C_1$–$C_6$ perfluoroalkyl, $R^8O$—, $R^9S(O)_m$—, $R^8C(O)NR^8$-, $(R^8)_2NC(O)$—, $R^9C(O)O$—, $R^8{}_2N$—$C(NR^8)$—, CN, $NO_2$, $R^8C(O)$—, $N_3$, —$N(R^8)_2$, or $R^9OC(O)NR^8$-,
 c) unsubstituted $C_1$–$C_6$ alkyl,
 d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^8O$—, $R^9S(O)_m$—, $R^8C(O)NR^8$-, $(R^8)_2NC(O)$—, $R^8{}_2N$—$C(NR^8)$—, CN, $R^8C(O)$—, $N_3$, —$N(R^8)_2$, and $R^9OC(O)$—$NR^8$-;

$R^4$ is independently selected from:
 a) hydrogen,
 b) aryl, substituted aryl, heterocycle, substituted heterocycle, $C_1$–$C_6$ alkyl, $C_2$–$C_6$ alkenyl, $C_2$–$C_6$ alkynyl, $C_1$–$C_6$ perfluoroalkyl, F, Cl, $R^8O$—, $R^8C(O)NR^8$-, CN, $NO_2$, $(R^8)_2N$—$C(NR^8)$—, $R^8C(O)$—, —$N(R^8)_2$, or $R^9OC(O)NR^8$-, and
 c) $C_1$–$C_6$ alkyl substituted by $C_1$–$C_6$ perfluoroalkyl, $R^8O$—, $R^8C(O)NR^8$-, $(R^8)_2N$—$C(NR^8)$—, $R^8C(O)$—, —$N(R^8)_2$, or $R^9OC(O)NR^8$-;

$R^{5a}$ and $R^{5b}$ are independently hydrogen, ethyl, cyclopropyl or methyl;

$R^6$, $R^7$ and $R^{7a}$ are independently selected from:
 H; $C_{1-4}$ alkyl, $C_{3-6}$ cycloalkyl, aryl, heterocycle, unsubstituted or substituted with:
  a) $C_{1-4}$ alkoxy,
  b) halogen, or
  c) substituted or unsubstituted aryl or substituted or unsubstituted heterocycle, $R^8$ is independently selected from hydrogen, $C_1$–$C_6$ alkyl, 2,2,2-trifluoroethyl, benzyl and aryl;

$R^9$ is independently selected from $C_1$–$C_6$ alkyl and aryl;
$R^{10}$ is selected from: H; $R^8C(O)$—; $R^9S(O)_m$—; unsubstituted or substituted $C_{1-4}$ alkyl, wherein the substituted alkyl group is substituted with one or two substituents selected from:
    a) $C_{1-4}$ alkoxy,
    b) aryl or heterocycle,
    c) halogen,
    d) HO, e) 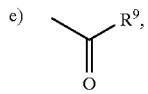

f) 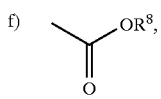

g) —$S(O)_mR^9$
    h) $N(R^8)_2$, and
    i) $C_{3-6}$ cycloalkyl;

$R^{11}$ is selected from: unsubstituted or substituted aryl, unsubstituted or substituted heterocycle, unsubstituted or substituted pyridinone, wherein the substituents on the cyclic group are selected from: halogen, —OH and —O($C_{1-6}$ alkyl);
$A^1$ is selected from: a bond, —C(O)—, O, —N($R^8$)—, or $S(O)_m$;
X is a bond, —C(=O)$NR^{10}$-, —$NR^{10}$C(=O)—, —S(O)$_m$— or —$NR^{10}$-;
n is 0 or 1; provided that n is not 0 if $A^1$ is a bond, O, —N($R^8$)—, or $S(O)_m$;
m is 0, 1 or 2;
p is 0, 1, 2, 3 or 4;
q is 0, 1, 2, 3 or 4, provided that q is not 0 when X is —C(=O)$NR^{10}$-, —$S(O)_m$— or —$NR^{10}$-; and
r is 0, 1 or 2;
or an optical isomer or pharmaceutically acceptable salt thereof.

6. The compound according to claim 4 which inhibits farnesyl-protein transferase of the formula E:

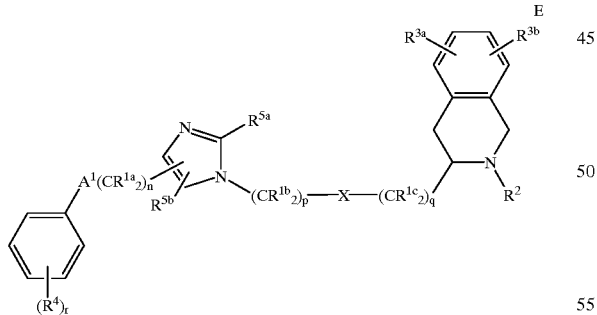

wherein:
$R^{1a}$ and $R^{1c}$ are independently selected from: hydrogen, $R^8O$—, —N($R^8$)$_2$, F, $C_3$–$C_{10}$ cycloalkyl or $C_1$–$C_6$ alkyl;
$R^{1b}$ is independently selected from:
    a) hydrogen,
    b) aryl, heterocycle, $C_3$–$C_{10}$ cycloalkyl, $R^8O$—, —N($R^8$)$_2$, F or $C_2$–$C_6$ alkenyl,
    c) $C_1$–$C_6$ alkyl unsubstituted or substituted by aryl, heterocycle, $C_3$–$C_{10}$ cycloalkyl, $C_2$–$C_6$ alkenyl, $R^8O$—, or —N($R^8$)$_2$;

$R^2$ is selected from: H; unsubstituted or substituted $C_{1-8}$ alkyl, unsubstituted or substituted aryl, $(CH_2)_pR^{11}$,

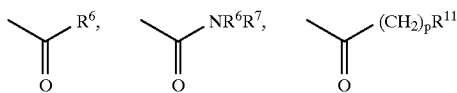

and —$S(O)_2R^6$,
wherein the substituted group is substituted with one or more of:
    1) aryl or heterocycle, unsubstituted or substituted with one or two groups selected from:
        a) $C_{1-4}$ alkyl,
        b) $(CH_2)_pOR^6$,
        c) $(CH_2)_pNR^6R^7$,
        d) halogen,
        e) $C_{1-4}$ perfluoroalkyl,
    2) $C_{3-6}$ cycloalkyl,
    3) $OR^6$,
    4) $SR^6$, $S(O)R^6$, $SO_2R^6$,
    5) —$NR^6R^7$ 6) 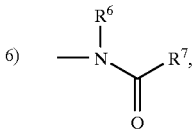

7) 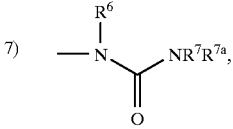

8) 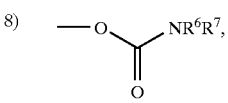

9) 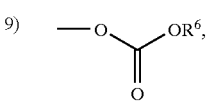

10) 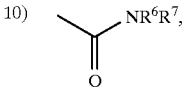

11) —$SO_2$—$NR^6R^7$

12) 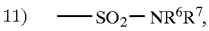

13) 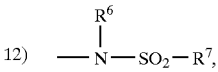

14) 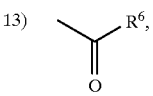

15) $C_{1-8}$ alkyl, or
    16) $C_{1-8}$ perfluoroalkyl;
$R^{3a}$ and $R^{3b}$ are independently selected from:
    a) hydrogen, b) unsubstituted or substituted aryl, unsubstituted or substituted heterocycle, unsubstituted or substituted $C_3$–$C_{10}$ cycloalkyl, unsubstituted or substituted $C_2$–$C_6$ alkenyl, $C_2$–$C_6$ alkynyl, halogen, $C_1$–$C_6$ perfluoroalkyl, $R^8O$—, $R^9S(O)_m$—, $R^8C(O)NR^8$-, $(R^8)_2NC(O)$—, $R^9C(O)O$—, $R^8_2N$—$C(NR^8)$—, CN, $NO_2$, $R^8C(O)$—, $N_3$, —$N(R^8)_2$, or $R^9OC(O)NR^8$-, c) unsubstituted $C_1$–$C_6$ alkyl, d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^8O$—, $R^9S(O)_m$—, $R^8C(O)NR^8$-, $(R^8)_2NC(O)$—, $R^8_2N$—$C(NR^8)$—, CN, $R^8C(O)$—, $N_3$, —$N(R^8)_2$, and $R^9OC(O)$—$NR^8$-;

$R^4$ is independently selected from:

a) hydrogen, b) aryl, substituted aryl, heterocycle, substituted heterocycle, $C_1$–$C_6$ alkyl, $C_2$–$C_6$ alkenyl, $C_2$–$C_6$ alkynyl, $C_1$–$C_6$ perfluoroalkyl, F, Cl, $R^8O$—, $R^8C(O)NR^8$-, CN, $NO_2$, $(R^8)_2N$—$C(NR^8)$—, $R^8C(O)$—, —$N(R^8)_2$, or $R^9OC(O)NR^8$-, and c) $C_1$–$C_6$ alkyl substituted by $C_1$—$C_6$ perfluoroalkyl, $R^8O$—, $R^8C(O)NR^8$-, $(R^8)_2N$—$C(NR^8)$—, $R^8C(O)$—, —N(R8)_2, or $R^9OC(O)NR^8$-;

$R^{5a}$ and $R^{5b}$ are independently hydrogen, ethyl, cyclopropyl or methyl;

$R^6$, $R^7$ and $R^{7a}$ are independently selected from:

H; $C_{1-4}$ alkyl, $C_{3-6}$ cycloalkyl, aryl, heterocycle, unsubstituted or substituted with:
a) $C_{1-4}$ alkoxy,
b) halogen, or
c) substituted or unsubstituted aryl or substituted or unsubstituted heterocycle, $R^8$ is independently selected from hydrogen, $C_1$–$C_6$ alkyl, 2,2,2-trifluoroethyl, benzyl and aryl;

$R^9$ is independently selected from $C_1$–$C_6$ alkyl and aryl;

$R^{10}$ is selected from: H; $R^8C(O)$—; $R^9S(O)_m$—; unsubstituted or substituted $C_{1-4}$ alkyl, wherein the substituted alkyl group is substituted with one or two substituents selected from:
a) $C_{1-4}$ alkoxy,
b) aryl or heterocycle,
c) halogen,
d) HO, e) 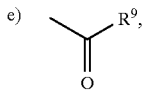

f) 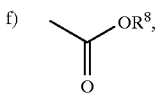

g) —$S(O)_mR^9$
h) $N(R^8)_2$, and
i) $C_{3-6}$ cycloalkyl;

$R^{11}$ is selected from: unsubstituted or substituted aryl, unsubstituted or substituted heterocycle, unsubstituted or substituted pyridinone, wherein the substituents on the cyclic group are selected from: halogen, —OH and —O($C_{1-6}$ alkyl);

X is a bond, —C(=O)NR$^{10}$-, —NR$^{10}$C(=O)—, —S(O)$_m$— or —NR$^{10}$-;

n is 0 or 1;

m is 0, 1 or 2;

p is 0, 1, 2, 3 or 4, provided that p is not 0 if X is a bond, —NR$^8$- or O;

q is 0, 1, 2, 3 or 4, provided that q is not 0 when X is —C(=O)NR$^{10}$-, —S(O)$_m$— or —NR$^{10}$-; and r is 0, 1 or 2;

or an optical isomer or pharmaceutically acceptable salt thereof.

7. The compound according to claim 5 which inhibits farnesyl-protein transferase of the formula F:

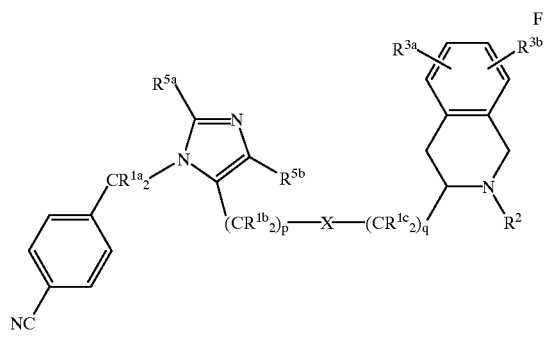

wherein:

$R^{1a}$ and $R^{1c}$ are independently selected from: hydrogen, $C_3$–$C_{10}$ cycloalkyl or $C_1$–$C_6$ alkyl;

$R^{1b}$ is independently selected from:
a) hydrogen,
b) aryl, heterocycle, $C_3$–$C_{10}$ cycloalkyl, $R^8O$—, —$N(R^8)_2$ or F,
c) $C_1$–$C_6$ alkyl unsubstituted or substituted by aryl, heterocycle, $C_3$–$C_{10}$ cycloalkyl, $R^8O$—, or —$N(R^8)_2$;

$R^2$ is selected from: H; unsubstituted or substituted $C_{1-8}$ alkyl, unsubstituted or substituted aryl, $(CH_2)_pR^{11}$,

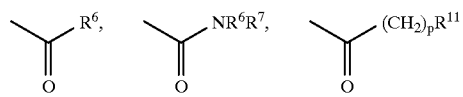

and —$S(O)_2R^6$, wherein the substituted group is substituted with one or more of:

1) aryl or heterocycle, unsubstituted or substituted with one or two groups selected from:
   a) $C_{1-4}$ alkyl,
   b) $(CH_2)_pOR^6$,
   c) $(CH_2)_pNR^6R^7$,
   d) halogen,
   e) $C_{1-4}$ perfluoroalkyl,
2) $C_{3-6}$ cycloalkyl,
3) $OR^6$,
4) $SR^6$, $S(O)R^6$, $SO_2R^6$,

5) —$NR^6R^7$,

6) 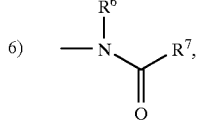

-continued

7) 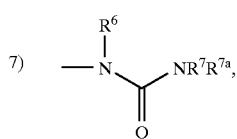

8) 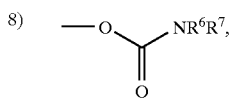

9) 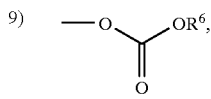

10) 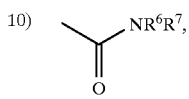

11) —SO$_2$—NR$^6$R$^7$,

12) 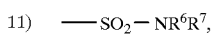

13) 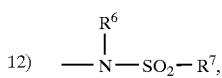

14) 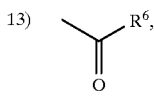

15) C$_{1-8}$ alkyl, or
16) C$_{1-8}$ perfluoroalkyl;

R$^{3a}$ and R$^{3b}$ are independently selected from:
 a) hydrogen,
 b) unsubstituted or substituted aryl, unsubstituted or substituted heterocycle, unsubstituted or substituted C$_3$–C$_{10}$ cycloalkyl, unsubstituted or substituted C$_2$–C$_6$ alkenyl, C$_2$–C$_6$ alkynyl, halogen, C$_1$–C$_6$ perfluoroalkyl, R$^8$O—, R$^9$S(O)$_m$—, R$^8$C(O)NR$^8$-, (R$^8$)$_2$NC(O)—, R$^9$C(O)O—, R$^8{}_2$N—C(NR$^8$)—, CN, NO$_2$, R$^8$C(O)—, N$_3$, —N(R$^8$)$_2$, or R$^9$OC(O)NR$^8$-,
 c) unsubstituted C$_1$–C$_6$ alkyl,
 d) substituted C$_1$–C$_6$ alkyl wherein the substituent on the substituted C$_1$–C$_6$ alkyl is selected from unsubstituted or substituted aryl, unsubstituted or substituted heterocyclic, C$_3$–C$_{10}$ cycloalkyl, C$_2$–C$_6$ alkenyl, C$_2$–C$_6$ alkynyl, R$^8$O—, R$^9$S(O)$_m$—, R$^8$C(O)NR$^8$-, (R$^8$)$_2$NC(O)—, R$^8{}_2$N—C(NR$^8$)—, CN, R$^8$C(O)—, N$_3$, —N(R$^8$)$_2$, and R$^9$OC(O)—NR$^8$-;

R$^{5a}$ and R$^{5b}$ are independently hydrogen, ethyl, cyclopropyl or methyl;

R$^6$, R$^7$ and R$^{7a}$ are independently selected from:
 H; C$_{1-4}$ alkyl, C$_{3-6}$ cycloalkyl, aryl, heterocycle, unsubstituted or substituted with:
  a) C$_{1-4}$ alkoxy,
  b) halogen, or
  c) substituted or unsubstituted aryl or substituted or unsubstituted heterocycle, R$^8$ is independently selected from hydrogen, C$_1$–C$_6$ alkyl, 2,2,2-trifluoroethyl, benzyl and aryl;

R$^9$ is independently selected from C$_1$–C$_6$ alkyl and aryl;

R$^{10}$ is selected from: H; R$^8$C(O)—; R$^9$S(O)$_m$—; unsubstituted or substituted C$_{1-4}$ alkyl, wherein the substituted alkyl group is substituted with one or two substituents selected from:
 a) C$_{1-4}$ alkoxy,
 b) aryl or heterocycle,
 c) halogen,
 d) HO, e) 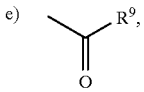

f) 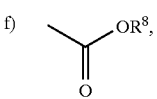

g) —S(O)$_m$R$^9$
h) N(R$^8$)$_2$, and
i) C$_{3-6}$ cycloalkyl;

R$^{11}$ is selected from: unsubstituted or substituted aryl, unsubstituted or substituted heterocycle, unsubstituted or substituted pyridinone, wherein the substituents on the cyclic group are selected from: halogen, —OH and —O(C$_{1-6}$ alkyl);

X is a bond, —C(=O)NR$^{10}$-, —NR$^{10}$C(=O)—, —S(O)$_m$— or —NR$^{10}$-;

m is 0, 1 or 2;
p is 0, 1, 2, 3 or 4; and
q is 0, 1, 2, 3 or 4, provided that q is not 0 when X is —C(=O)NR$^{10}$-, —S(O)$_m$— or —NR$^{10}$-;

or an optical isomer or pharmaceutically acceptable salt thereof.

8. The compound according to claim 6 which inhibits farnesyl-protein transferase of the formula G:

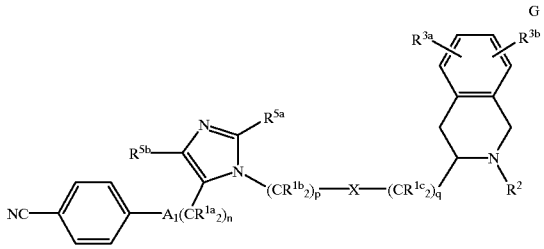

wherein:

R$^{1a}$ and R$^{1c}$ are independently selected from: hydrogen, R$^8$O—, —N(R$^8$)$_2$, F, C$_3$–C$_{10}$ cycloalkyl or C$_1$–C$_6$ alkyl;

R$^{1b}$ is independently selected from:
 a) hydrogen,
 b) aryl, heterocycle or C$_3$–C$_{10}$ cycloalkyl,
 c) C$_1$–C$_6$ alkyl unsubstituted or substituted by aryl, heterocycle, C$_3$–C$_{10}$ cycloalkyl, C$_2$–C$_6$ alkenyl, R$^8$O—, or —N(R$^8$)$_2$;

R$^2$ is selected from: H; unsubstituted or substituted C$_{1-8}$ alkyl, unsubstituted or substituted aryl, (CH$_2$)$_p$R$^{11}$,

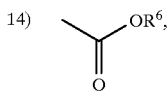

and —S(O)$_2$R$^6$, wherein the substituted group is substituted with one or more of:

1) aryl or heterocycle, unsubstituted or substituted with one or two groups selected from:
   a) $C_{1-4}$ alkyl,
   b) $(CH_2)_pOR^6$,
   c) $(CH_2)_pNR^6R^7$,
   d) halogen,
   e) $C_{1-4}$ perfluoroalkyl,
2) $C_{3-6}$ cycloalkyl,
3) $OR^6$,
4) $SR^6$, $S(O)R^6$, $SO_2R^6$,
5) —$NR^6R^7$ 6) 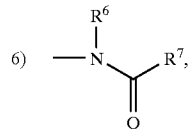

7) 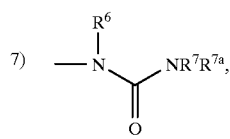

8) 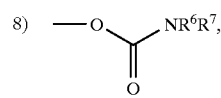

9) 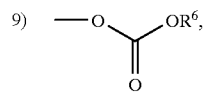

10) 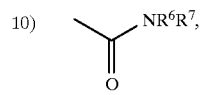

11) —$SO_2$—$NR^6R^7$,

12) 

13) 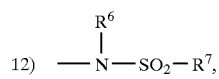

14) 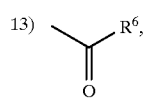

15) $C_{1-8}$ alkyl, or
16) $C_{1-8}$ perfluoroalkyl;

$R^{3a}$ and $R^{3b}$ are independently selected from:
 a) hydrogen,
 b) unsubstituted or substituted aryl, unsubstituted or substituted heterocycle, unsubstituted or substituted $C_3$–$C_{10}$ cycloalkyl, unsubstituted or substituted $C_2$–$C_6$ alkenyl, $C_2$–$C_6$ alkynyl, halogen, $C_1$–$C_6$ perfluoroalkyl, $R^8O$—, $R^9S(O)_m$—, $R^8C(O)NR^8$-, $(R^8)_2NC(O)$—, $R^9C(O)O$—, $R^8{}_2N$—$C(NR^8)$—, CN, $NO_2$, $R^8C(O)$—, $N_3$, —$N(R^8)_2$, or $R^9OC(O)NR^8$-,
 c) unsubstituted $C_1$–$C_6$ alkyl,
 d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^8O$—, $R^9S(O)_m$—, $R^8C(O)NR^8$-, $(R^8)_2NC(O)$—, $R^8{}_2N$—$C(NR^8)$—, CN, $R^8C(O)$—, $N_3$, —$N(R^8)_2$, and $R^9OC(O)$—$NR^8$-;

$R^{5a}$ and $R^{5b}$ are independently hydrogen, ethyl, cyclopropyl or methyl;
$R^6$, $R^7$ and $R^{7a}$ are independently selected from:
  H; $C_{1-4}$ alkyl, $C_{3-6}$ cycloalkyl, aryl, heterocycle, unsubstituted or substituted with:
   a) $C_{1-4}$ alkoxy,
   b) halogen, or
   c) substituted or unsubstituted aryl or substituted or unsubstituted heterocycle,
$R^8$ is independently selected from hydrogen, $C_1$–$C_6$ alkyl, 2,2,2-trifluoroethyl, benzyl and aryl;
$R^9$ is independently selected from $C_1$–$C_6$ alkyl and aryl;
$R^{10}$ is selected from: H; $R^8C(O)$—; $R^9S(O)_m$—; unsubstituted or substituted $C_{1-4}$ alkyl, wherein the substituted alkyl group is substituted with one or two substituents selected from:
   a) $C_{1-4}$ alkoxy,
   b) aryl or heterocycle,
   c) halogen,
   d) HO, e) 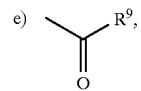

f) 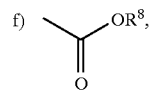

g) —$S(O)_mR^9$
   h) $N(R^8)_2$, and
   i) $C_{3-6}$ cycloalkyl;

$R^{11}$ is selected from: unsubstituted or substituted aryl, unsubstituted or substituted heterocycle, unsubstituted or substituted pyridinone, wherein the substituents on the cyclic group are selected from: halogen, —OH and —$O(C_{1-6}$ alkyl);
$A^1$ is selected from: a bond, —C(O)—, O, —$N(R^8)$—, or $S(O)_m$;
X is a bond, —C(=O)$NR^{10}$-, —$NR^{10}$C(=O)—, —$S(O)_m$— or —$NR^{10}$-;
m is 0, 1 or 2;
n is 0 or 1;
p is 1, 2 or 3; and
q is 0, 1, 2, 3 or 4, provided that q is not 0 when X is —C(=O)$NR^{10}$-, —$S(O)_m$— or —$NR^{10}$-;
or an optical isomer or a pharmaceutically acceptable salt thereof.

9. A compound which inhibits farnesyl-protein transferase which is:

2-Benzyl-1,2,3,4-tetrahydro-isoquinoline-3(S)-carboxylic acid {2-[3-(4-cyanobenzyl)-3H-imidazol-4-yl]-ethyl}-amide 2-(2-Chlorobenzyl)-1,2,3,4-tetrahydro-isoquinoline-3(S)-carboxylic acid {2-[3-(4-cyanobenzyl)-3H-imidazol-4-yl]-ethyl}-amide 2-(3–Chlorobenzyl)-1,2,3,4-tetrahydro-isoquinoline-3(R)-carboxylic acid {2-[3-(4-cyanobenzyl)-3H-imidazol-4-yl]-ethyl}-amide 2-(3-Chlorobenzyl)-1,2,3,4-tetrahydro-isoquinoline-3(S)-carboxylic acid {2-[3-(4-cyanobenzyl)-3H-imidazol-4-yl]-ethyl}-amide 2-(4–Chlorobenzyl)-1,2,3,4-tetrahydro-isoquinoline-3(S)-carboxylic acid {2-[3-(4-cyanobenzyl)-3H-imidazol-4-yl]-ethyl}-amide 2-(2-Phenylethyl)-1,2,3,4-tetrahydro-isoquinoline-3(S)-carboxylic acid {2-[3-(4-cyanobenzyl)-3H-imidazol-4-yl]-ethyl}-amide 2-(2,2-Diphenylethyl)-1,2,3,4-tetrahydro-isoquinoline-3(S)-carboxylic acid {2-[3-(4-cyanobenzyl)-3H-imidazol-4-yl]-ethyl}-amide 2-(3-Trifluoromethoxybenzyl)-1,2,3,4-tetrahydro-isoquinoline-3(S)-carboxylic acid {2-[3-(4-cyanobenzyl)-3H-imidazol-4-yl]-ethyl}-amide 2-(n-Butyl)-1,2,3,4-tetrahydro-isoquinoline-3(S)-carboxylic acid {2-[3-(4-cyanobenzyl)-3H-imidazol-4-yl]-ethyl}-amide 2-(3-Pyridylmethyl)-1,2,3,4-tetrahydro-isoquinoline-3(S)-carboxylic acid {2-[3-(4-cyanobenzyl)-3H-imidazol-4-yl]-ethyl}-amide 2-(3-Trifluoromethoxybenzyl)-1,2,3,4-tetrahydro-isoquinoline-3(R)-carboxylic acid {2-[3-(4-cyanobenzyl)-3H-imidazol-4-yl]-ethyl}-amide 2-(3-Methoxybenzyl)-1,2,3,4-tetrahydro-isoquinoline-3(R)-carboxylic acid {2-[3-(4-cyanobenzyl)-3H-imidazol-4-yl]-ethyl}-amide 2-(3–Chlorobenzyl)-7-hydroxy- 1,2,3,4-tetrahydro-isoquinoline-3(S)-carboxylic acid {2-[3-(4-cyanobenzyl)-3H-imidazol-4-yl]-ethyl}-amide 2-(3-Chlorobenzyl)-1,2,3,4-tetrahydro-isoquinoline-3(S)-carboxylic acid {2-[3-(4-cyanobenzyl)-2-methyl-3H-imidazol-4-yl]-ethyl}-amide 2-(3-Trifluoromethoxybenzyl)-1,2,3,4-tetrahydro-isoquinoline-3(S)-carboxylic acid {2-[3-(4-cyanobenzyl)-2-methyl-3H-imidazol-4-yl]-ethyl}-amide 2-(2,3-Dimethylbenzoyl)-1,2,3,4-tetrahydro-isoquinoline-3(S)-carboxylic acid {2-[3-(4-cyanobenzyl)-3H-imidazol-4-yl]-ethyl}-amide 2-(3-Chlorophenylsulfonyl)-1,2,3,4-tetrahydro-isoquinoline-3(S)-carboxylic acid {2-[3-(4-cyanobenzyl)-3H-imidazol-4-yl]-ethyl}-amide 2-(3-Chlorobenzyl)-7-methoxy- 1,2,3,4-tetrahydro-isoquinoline-3(S)-carboxylic acid {2-[3-(4-cyanobenzyl)-3H-imidazol-4-yl]-ethyl}-amide 2-n-Butyl-7-methoxy-1,2,3,4-tetrahydro-isoquinoline-3(S)-carboxylic acid {2-[3-(4-cyanobenzyl)-3H-imidazol-4-yl]-ethyl}-amide 4-{3-[2-(3-chlorobenzyl)-(S)-1,2,3,4-tetrahydro-isoquinolin-3-yl-methyl]-3H-imidazol-4-yl-methyl}-benzonitrile 4-{3-[2-(1 -(5-chloro-pyridin-2-one)ethyl)-(S)-1,2,3,4-tetrahydro-isoquinolin-3-yl-methyl]-3H-imidazol-4-yl-methyl}-benzonitrile 4-{3-[2-(methylsulfonylethyl)-(S)-1,2,3,4-tetrahydro-isoquinolin-3-yl-methyl]-3H-imidazol-4-yl-methyl}-benzonitrile 4-{3-[2-(3-methoxybenzoyl)-(S)-1,2,3,4-tetrahydro-isoquinolin-3-yl-methyl]-3H-imidazol-4-yl-methyl}-benzonitrile 4-{3-[2-(3-methoxyphenylacetyl)-(S)-1,2,3,4-tetrahydro-isoquinolin-3-yl-methyl]-3H-imidazol-4-yl-methyl}-benzonitrile and 4-{3-[2-(1-(5-chloro-pyridin-2-one)acetyl)-(S)-1,2,3,4-tetrahydro-isoquinolin-3-yl-methyl]-3H-imidazol-4-yl-methyl}-benzonitrile, and 2-[1-(5-Chloro-pyridin-2-one)ethyl]-7-methoxy -1,2,3,4-tetrahydro-isoquinoline-3(S)-carboxylic acid {2-[3-(4-cyanobenzyl)-3H-imidazol-4-yl]-ethyl }-amide or an optical isomer or a pharmaceutically acceptable salt thereof.

10. The compound according to claim 9 which is:

2-(3-Chlorobenzyl)-1,2,3,4-tetrahydro-isoquinoline-3(S)-carboxylic acid {2-[3-(4-cyanobenzyl)-3H-imidazol-4-yl]-ethyl}-amide

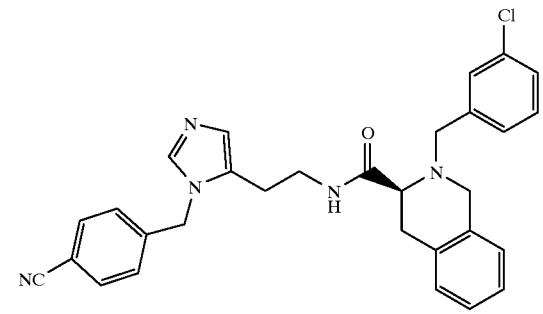

or an optical isomer or a pharmaceutically acceptable salt thereof.

11. The compound according to claim 9 which is:

2-(3-Chlorophenylsulfonyl)-1,2,3,4-tetrahydro-isoquinoline-3(S)-carboxylic acid {2-[3-(4-cyanobenzyl)-2-methyl-3H-imidazol-4-yl]-ethyl}-amide

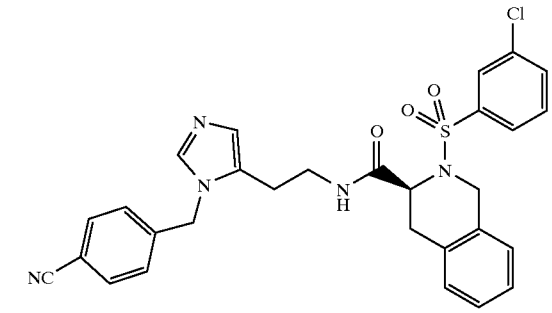

or an optical isomer or a pharmaceutically acceptable salt thereof.

12. The compound according to claim 9 which is:

2-(n-Butyl)-1,2,3,4-tetrahydro-isoquinoline-3(S)-carboxylic acid {2-[3-(4-cyanobenzyl)-3H-imidazol-4-yl]-ethyl}-amide

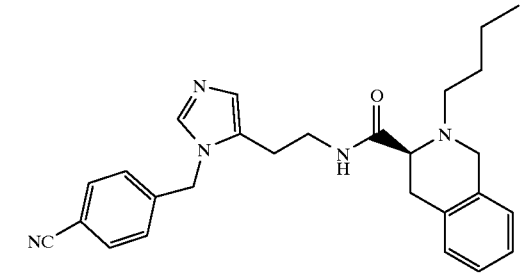

or an optical isomer or a pharmaceutically acceptable salt thereof.

13. The compound according to claim 9 which is:

2-(3-Pyridylmethyl)-1,2,3,4-tetrahydro-isoquinoline-3(S)-carboxylic acid {2-[3-(4-cyanobenzyl)-3H-imidazol-4- yl]-ethyl}-amide

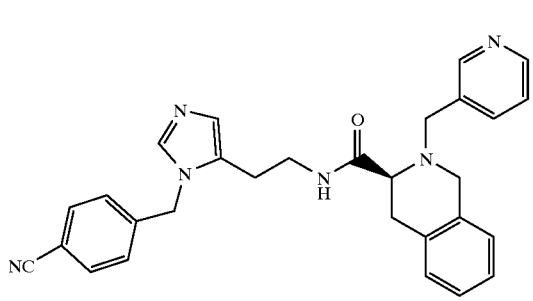

or an optical isomer or a pharmaceutically acceptable salt thereof.

14. The compound according to claim 9 which is:

2-(3-Methoxybenzyl)-1,2,3,4-tetrahydro-isoquinoline-3(R)-carboxylic acid {2-[3-(4-cyanobenzyl)-3H-imidazol-4-yl]-ethyl}-amide

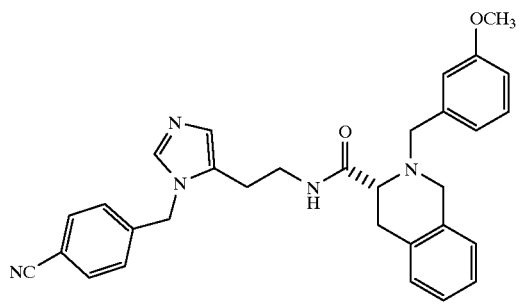

or an optical isomer or a pharmaceutically acceptable salt thereof.

15. The compound according to claim 9 which is:

2-(3-Chlorobenzyl)-7-methoxy-1,2,3,4-tetrahydro-isoquinoline-3(S)-carboxylic acid {2-[3-(4-cyanobenzyl)-3H-imidazol-4-yl]-ethyl}-amide

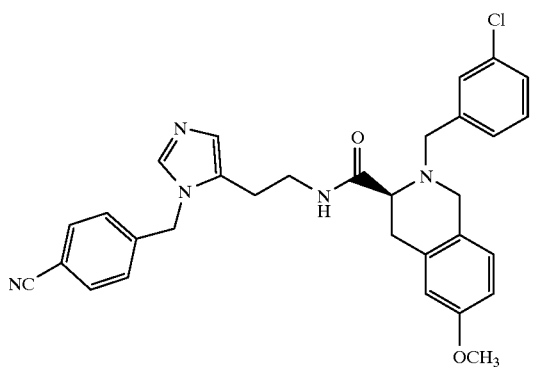

or an optical isomer or a pharmaceutically acceptable salt thereof.

16. The compound according to claim 9 which is:

4-{3-[2-(1-(5-chloro-pyridin-2-one)acetyl)-(S)-1,2,3,4-tetrahydro-isoquinolin-3-yl-methyl]-3H-imidazol-4-yl-methyl}-benzonitrile

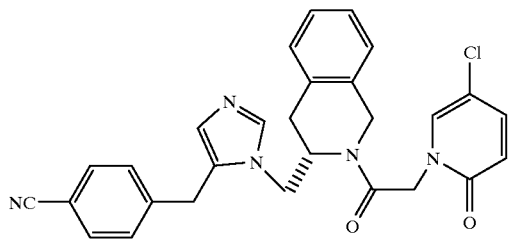

or an optical isomer or a pharmaceutically acceptable salt thereof.

17. The compound according to claim 9 which is:

4-{3-[2-(3-methylsulfonylethyl)-(S)-1,2,3,4-tetrahydro-isoquinolin-3-yl-methyl]-3H-imidazol-4-yl-methyl}-benzonitrile

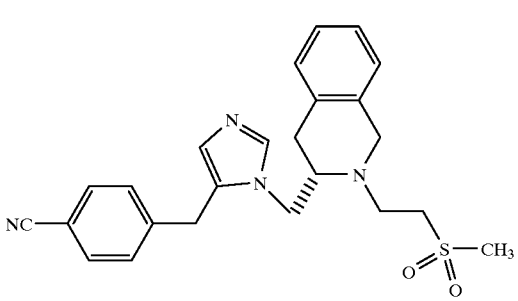

or an optical isomer or a pharmaceutically acceptable salt thereof.

18. The compound according to claim 9 which is:

4-{3-[2-(3-methoxybenzoyl)-(S)-1,2,3,4-tetrahydro-isoquinolin-3-yl-methyl]-3H-imidazol-4-yl-methyl}-benzonitrile

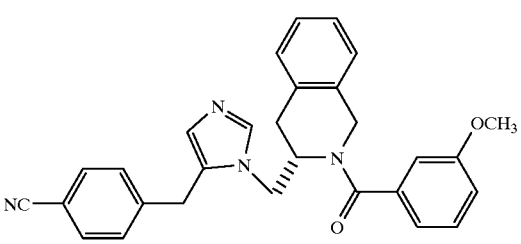

or an optical isomer or a pharmaceutically acceptable salt thereof.

19. The compound according to claim 9 which is:

2-[1-(5-Chloro-pyridin-2-one)ethyl]-7-methoxy-1,2,3,4-tetrahydro-isoquinoline-3(S)-carboxylic acid {2-[3-(4-cyanobenzyl)-3H-imidazol-4-yl]-ethyl}-amide

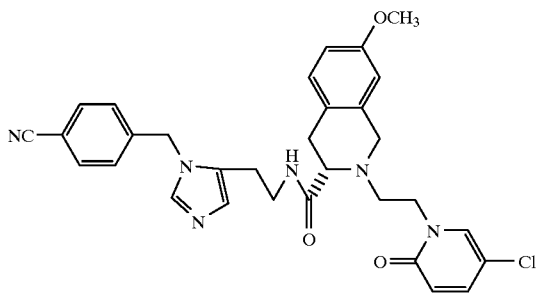

or an optical isomer or a pharmaceutically acceptable salt thereof.

20. A pharmaceutical composition comprising a pharmaceutical carrier, and dispersed therein, a therapeutically effective amount of a compound of claim 1.

21. A pharmaceutical composition comprising a pharmaceutical carrier, and dispersed therein, a therapeutically effective amount of a compound of claim 3.

22. A pharmaceutical composition comprising a pharmaceutical carrier, and dispersed therein, a therapeutically effective amount of a compound of claim 4.

23. A pharmaceutical composition comprising a pharmaceutical carrier, and dispersed therein, a therapeutically effective amount of a compound of claim 9.

24. A method for inhibiting farnesyl-protein transferase which comprises administering to a mammal in need thereof a therapeutically effective amount of a composition of claim 20.

25. A method for inhibiting farnesyl-protein transferase which comprises administering to a mammal in need thereof a therapeutically effective amount of a composition of claim 21.

26. A method for inhibiting farnesyl-protein transferase which comprises administering to a mammal in need thereof a therapeutically effective amount of a composition of claim 22.

27. A method for inhibiting farnesyl-protein transferase which comprises administering to a mammal in need thereof a therapeutically effective amount of a composition of claim 23.

28. A method for treating cancer which comprises administering to a mammal in need thereof a therapeutically effective amount of a composition of claim 20.

29. A method for treating cancer which comprises administering to a mammal in need thereof a therapeutically effective amount of a composition of claim 21.

30. A method for treating cancer which comprises administering to a mammal in need thereof a therapeutically effective amount of a composition of claim 22.

31. A method for treating cancer which comprises administering to a mammal in need thereof a therapeutically effective amount of a composition of claim 23.

32. A method for treating neurofibromin benign proliferative disorder which comprises administering to a mammal in need thereof a therapeutically effective amount of a composition of claim 20.

33. A method for treating blindness related to retinal vascularization which comprises administering to a mammal in need thereof a therapeutically effective amount of a composition of claim 20.

34. A method for treating infections from hepatitis delta and related viruses which comprises administering to a mammal in need thereof a therapeutically effective amount of a composition of claim 20.

35. A method for preventing restenosis which comprises administering to a mammal in need thereof a therapeutically effective amount of a composition of claim 20.

36. A method for treating polycystic kidney disease which comprises administering to a mammal in need thereof a therapeutically effective amount of a composition of claim 20.

37. A pharmaceutical composition made by combining the compound of claim 1 and a pharmaceutically acceptable carrier.

38. A process for making a pharmaceutical composition comprising combining a compound of claim 1 and a pharmaceutically acceptable carrier.

* * * * *

UNITED STATES PATENT AND TRADEMARK OFFICE
CERTIFICATE OF CORRECTION

PATENT NO. : 5,932,590
DATED : August 3, 1999
INVENTOR(S) : Terrence M. Ciccarone and S. Jane deSolms It is certified that error appears in the above-identified patent and that said Letters Patent is hereby corrected as shown below:

In Column 83, line 19 should read as follows:
-- stituted heterocycle, $C_3$-$C_{10}$ cycloalkyl, $C_2$-$C_6$ -- .

In Column 83, between lines 53 and 55, insert the following:
-- 5) -$NR^6R^7$, -- .

In Column 87, line 37 should read as follows:
-- $R^{3a}$ and $R^{3b}$ are independently selected from: -- .

In Column 93, line 66 should read as follows:
-- $R^8O$-, $R^8C(O)NR^8$-, $(R^8)_2N$-$C(NR^8)$-, $R^8C(O)$-, -- .

In Column 99, line 24 should read as follows:
-- c) $C_1$-$C_6$ alkyl substituted by $C_1$-$C_6$ perfluoroalkyl, -- .

In Column 99, line 26 should read as follows:
-- -$N(R^8)_2$, or $R^9OC(O)NR^8$-; -- .

Signed and Sealed this

Twenty-eighth Day of March, 2000

Attest:

Q. TODD DICKINSON

Attesting Officer

Commissioner of Patents and Trademarks

```
                              SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
          (A) LENGTH: 15 amino acids
          (B) TYPE: amino acid
          (C) STRANDEDNESS: single
          (D) TOPOLOGY: linear (ii) MOLECULE TYPE: protein (xi) SEQUENCE DESCRIPTION: SEQ ID NO:1:

Gly Lys Lys Lys Lys Lys Ser Lys Thr Lys Cys Val Ile Met
 1               5                  10                  15

(2) INFORMATION FOR SEQ ID NO:2:

(i) SEQUENCE CHARACTERISTICS:
          (A) LENGTH: 86 base pairs
          (B) TYPE: nucleic acid
          (C) STRANDEDNESS: single
          (D) TOPOLOGY: linear (ii) MOLECULE TYPE: Genomic DNA (xi) SEQUENCE DESCRIPTION: SEQ ID NO:2:

TCTCCTCGAG GCCACCATGG GGAGTAGCAA GAGCAAGCCT AAGGACCCCA GCCAGCGCCG      60

GATGACAGAA TACAAGCTTG TGGTGG                                          86

(2) INFORMATION FOR SEQ ID NO:3:

(i) SEQUENCE CHARACTERISTICS:
          (A) LENGTH: 33 base pairs
          (B) TYPE: nucleic acid
          (C) STRANDEDNESS: single
          (D) TOPOLOGY: linear (ii) MOLECULE TYPE: Genomic DNA (xi) SEQUENCE DESCRIPTION: SEQ ID NO:3:

CACATCTAGA TCAGGACAGC ACAGACTTGC AGC                                  33

(2) INFORMATION FOR SEQ ID NO:4:

(i) SEQUENCE CHARACTERISTICS:
          (A) LENGTH: 41 base pairs
          (B) TYPE: nucleic acid
          (C) STRANDEDNESS: single
          (D) TOPOLOGY: linear (ii) MOLECULE TYPE: Genomic DNA (xi) SEQUENCE DESCRIPTION: SEQ ID NO:4:
```

TCTCCTCGAG GCCACCATGA CAGAATACAA GCTTGTGGTG G                    41

(2) INFORMATION FOR SEQ ID NO:5:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:5:

CACTCTAGAC TGGTGTCAGA GCAGCACACA CTTGCAGC                        38

(2) INFORMATION FOR SEQ ID NO:6:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:6:

GAGAGAATTC GCCACCATGA CGGAATATAA GCTGGTGG                        38

(2) INFORMATION FOR SEQ ID NO:7:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:7:

GAGAGTCGAC GCGTCAGGAG AGCACACACT TGC                             33

(2) INFORMATION FOR SEQ ID NO:8:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:8:

CCGCCGGCCT GGAGGAGTAC AG                                         22

(2) INFORMATION FOR SEQ ID NO:9:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:9:

GAGAGAATTC GCCACCATGA CTGAGTACAA ACTGGTGG                        38

(2) INFORMATION FOR SEQ ID NO:10:

(i) SEQUENCE CHARACTERISTICS:
             (A) LENGTH: 32 base pairs
             (B) TYPE: nucleic acid
             (C) STRANDEDNESS: single
             (D) TOPOLOGY: linear (ii) MOLECULE TYPE: Genomic DNA (xi) SEQUENCE DESCRIPTION: SEQ ID NO:10:

GAGAGTCGAC TTGTTACATC ACCACACATG GC                                             32

(2) INFORMATION FOR SEQ ID NO:11:

(i) SEQUENCE CHARACTERISTICS:
             (A) LENGTH: 21 base pairs
             (B) TYPE: nucleic acid
             (C) STRANDEDNESS: single
             (D) TOPOLOGY: linear (ii) MOLECULE TYPE: Genomic DNA (xi) SEQUENCE DESCRIPTION: SEQ ID NO:11:

GTTGGAGCAG TTGGTGTTGG G                                                         21

(2) INFORMATION FOR SEQ ID NO:12:

(i) SEQUENCE CHARACTERISTICS:
             (A) LENGTH: 38 base pairs
             (B) TYPE: nucleic acid
             (C) STRANDEDNESS: single
             (D) TOPOLOGY: linear (ii) MOLECULE TYPE: Genomic DNA (xi) SEQUENCE DESCRIPTION: SEQ ID NO:12:

GAGAGGTACC GCCACCATGA CTGAATATAA ACTTGTGG                                       38

(2) INFORMATION FOR SEQ ID NO:13:

(i) SEQUENCE CHARACTERISTICS:
             (A) LENGTH: 36 base pairs
             (B) TYPE: nucleic acid
             (C) STRANDEDNESS: single
             (D) TOPOLOGY: linear (ii) MOLECULE TYPE: Genomic DNA (xi) SEQUENCE DESCRIPTION: SEQ ID NO:13:

CTCTGTCGAC GTATTTACAT AATTACACAC TTTGTC                                         36

(2) INFORMATION FOR SEQ ID NO:14:

(i) SEQUENCE CHARACTERISTICS:
             (A) LENGTH: 24 base pairs
             (B) TYPE: nucleic acid
             (C) STRANDEDNESS: single
             (D) TOPOLOGY: linear (ii) MOLECULE TYPE: Genomic DNA (xi) SEQUENCE DESCRIPTION: SEQ ID NO:14:

GTAGTTGGAG CTGTTGGCGT AGGC                                                      24